US008318923B2

(12) United States Patent
Layzer et al.

(10) Patent No.: US 8,318,923 B2
(45) Date of Patent: Nov. 27, 2012

(54) NUCLEIC ACID MODULATORS OF GLYCOPROTEIN VI

(75) Inventors: Juliana M. Layzer, Durham, NC (US); Christopher P. Rusconi, Durham, NC (US); Douglas Brooks, Durham, NC (US); Steven L. Zelenkofske, Center Valley, PA (US)

(73) Assignee: Regado Biosciences, Inc., Durham, NC (US)

( * ) Notice: Subject to any disclaimer, the term of this patent is extended or adjusted under 35 U.S.C. 154(b) by 117 days.

(21) Appl. No.: 12/793,572

(22) Filed: Jun. 3, 2010

(65) Prior Publication Data

US 2010/0311820 A1    Dec. 9, 2010

Related U.S. Application Data

(60) Provisional application No. 61/183,847, filed on Jun. 3, 2009, provisional application No. 61/300,951, filed on Feb. 3, 2010.

(51) Int. Cl.
*C07H 21/04* (2006.01)
(52) U.S. Cl. .................................................. 536/24.5
(58) Field of Classification Search .................. 536/24.5
See application file for complete search history.

(56) References Cited

U.S. PATENT DOCUMENTS

| 6,245,527 | B1 | 6/2001 | Busfield et al. | |
|---|---|---|---|---|
| 7,300,922 | B2 | 11/2007 | Sullenger et al. | |
| 7,312,325 | B2 | 12/2007 | Sullenger et al. | |
| 7,645,592 | B2 | 1/2010 | Takizawa et al. | |
| 7,655,787 | B2* | 2/2010 | Guo et al. | 536/24.5 |
| 2008/0050380 | A1 | 2/2008 | Gill et al. | |
| 2008/0311630 | A1* | 12/2008 | Schroff et al. | 435/91.53 |
| 2009/0048193 | A1 | 2/2009 | Rusconi et al. | |
| 2011/0002892 | A1* | 1/2011 | Galloway et al. | 424/93.7 |

FOREIGN PATENT DOCUMENTS

| WO | WO 02/096926 A1 | 12/2002 |
|---|---|---|
| WO | WO 2005/106042 A2 | 11/2005 |
| WO | WO 2006/061650 A2 | 6/2006 |

OTHER PUBLICATIONS

Cabeza, et al., "Surface expression of collagen receptor Fc receptor-γ/glycoprotein VI is enhanced on platelets in type 2 diabetes and mediates release of CD40 ligand and activation of endothelial cells", Diabetes, vol. 53, pp. 2117-2121, (2004).
Horii, et al., "Structural basis for platelet collagen responses by the immune-type receptor glycoprotein VI", Blood, vol. 108, No. 3, pp. 936-942, (2006).
May, et al., "Platelets: Inflammatory firebugs of vascular walls", Arterioscler. Thromb. Vasc. Biol., vol. 28, pp. s5-s10, (2008).
Nieswandt & Watson, "Platelet-collagen interaction: is GPVI the central receptor?", Blood, vol. 102, No. 2, pp. 449-461, (2003).
Polgar, et al., "Platelet activation and signal transduction by convulxin, a C-type lectin from *Crotalus durissus terrificus* (Tropical Rattlesnake) venom via the p62/GPVI collagen receptor," J. Biol. Chem., vol. 272, No. 21, pp. 13576-13583 (1997).
Rivera, et al., "Platelet receptors and signaling in the dynamics of thrombus formation", Haematologica, vol. 94, pp. 700-711 (2009).
Sarratt, et al., "GPVI and $\alpha_2\beta_1$ play independent critical roles during adhesion and aggregate formation to collagen under flow", Blood, vol. 106, No. 4, pp. 1268-1277 (2005).
Smethurst, et al., "Identification of the primary collagen-binding surface on human glycoprotein VI by site-directed mutagenesis and by a blocking phage antibody," Blood, vol. 103, No. 3, pp. 903-911 (2004).
Smethurst, et al., "Structural basis for the platelet-collagen interaction, the smallest motif within collagen that recognizes and activates platelet glycoprotein VI contains two glycine-proline-hydroxyproline triplets," J. Biol. Chem., vol. 282, No. 2, pp. 1296-1304 (2007).
Von Hundelshausen & Weber, "Platelets as immune cells: Bridging inflammation and cardiovascular disease", Circ. Res., vol. 100, pp. 27-40, (2007).
Zahn, et al., "Hepatitis C virus interacts with human platelet glycoprotein VI", J. Gen. Virol., vol. 87, pp. 2243-2251, (2006).
Bigalke, et al., "Platelet collagen receptor glycoprotein VI as a possible novel indicator for the acute coronary syndrome", American Heart Journal, vol. 156, No. 1, pp. 193-200 (2008).
Kiefer, et al., "Inhibitors of platelet adhesion", Circulation, vol. 120, No. 24, pp. 2488-2495 (2009).
International Search Report from PCT Patent Application No. PCT/US2010/037319 mailed Sep. 29, 2010.

* cited by examiner

*Primary Examiner* — Brian Whiteman
(74) *Attorney, Agent, or Firm* — King & Spalding LLP

(57) ABSTRACT

The present invention relates, in general, to a pharmacologic system to modulate the biology of platelets based upon a nucleic acid ligand that can interact with and modulate the activity of platelet glycoprotein GPVI to regulate platelet function. These nucleic acid ligands are also actively reversible using a modulator that inhibits the activity of the nucleic acid ligand to neutralize this pharmacologic effect and thereby restore GPVI function, including collagen binding, platelet adhesion, collagen-induced platelet activation, and collagen-induced platelet aggregation. The invention further relates to compositions comprising the nucleic acid ligand, the ligand and a modulator, methods to generate the nucleic acid ligand and its modulator, as well as methods of using these agents and compositions in medical therapeutic and diagnostic procedures.

23 Claims, 30 Drawing Sheets

| SELEX Round | [Protein] µM | [RNA] µM | RNA:Protein | Input RNA | Buffer | Wash Buffer | Incubation Time |
|---|---|---|---|---|---|---|---|
| 1 E2 | 2 | 10 | 5 | 1 nmole | E | E | 15' incubation |
| 2 E2 | 0.35 | 3.5 | 10 | 1 nmole | E | E | 15' incubation |
| 3 E2 | 0.25 | 2.5 | 10 | 1 nmole | E | E | 15' incubation |
| 4 E2 | 0.25 | 2.5 | 10 | 1 nmole | E | E | 15' incubation |
| 5 E2 | 0.035 | 0.35 | 10 | 1 nmole | E | E | 20' incubation |
| 6 E2 | 0.035 | 0.35 | 10 | 1 nmole | E | E | 20' incubation |
| 7 E2 | 0.002 | 0.03 | 15 | 1 nmole | E | E | 30' incubation |
| 8 E2 | 0.002 | 0.03 | 15 | 1 nmole | E | E | 30' incubation |
| 7 EF | 0.025 | 0.25 | 10 | 1 nmole | F | F | 30' incubation |
| 8 EF | 0.025 | 0.25 | 10 | 1 nmole | F | F | 30' incubation |
| 9 E2 AND 9 EF | 0.007 | 0.105 | 15 | 1 nmole | F | F | 30' incubation |
| 10 E2 AND 10 EF | 0.005 | 0.085 | 17 | 1 nmole | F | F | 30' incubation |

Figure 2

R10 E/F Sequences

| | Random Region | Sequence | SEQ ID NO: |
|---|---|---|---|
| R10-EF-3 | ATCACACCGCGTCTTGCGTAAGCCTCCTACTAACGGATCG | C | 7 |
| R10-EF-14 | ATCACACCGCGTCTTGCGTAAGCCTCCTACTAACGGATCG | C | 7 |
| R10-EF-17 | ATCACACCGCGTCTTGCGTAAGCCTCCTACTAACGGATCG | C | 7 |
| R10-EF-39 | ATCACACCGCGTCTTGCGTAAGCCTCCTACTAACGGATCG | C | 7 |
| R10-EF-4 | ATCAC-CCGCGTCTTGCGTAAGCCTCCTACTAACGGATCG | C | 8 |
| | | | |
| R10-EF-22 | ATTCAACCCGCCTCTGGCATAAGCCTACCCATCGTGATTGT | E | 9 |
| | | | |
| R10-EF-35 | CAATCGAAGCTGCATCCAGCGTAAGCCTTCCAGGGACCGT | A | 10 |
| R10-EF-1 | CAATCGAAGCTGCATCCAGCGTAAGCCTTCCAGGGATCGT | A | 11 |
| R10-EF-5 | CAATCGAAGCTGCATCCAGCGTAAGCCTTCCAGGGATCGT | A | 11 |
| R10-EF-6 | CAATCGAAGCTGCATCCAGCGTAAGCCTTCCAGGGATCGT | A | 11 |
| R10-EF-9 | CAATCGAAGCTGCATCCAGCGTAAGCCTTCCAGGGATCGT | A | 11 |
| R10-EF-15 | CAATCGAAGCTGCATCCAGCGTAAGCCTTCCAGGGATCGT | A | 11 |
| R10-EF-20 | CAATCGAAGCTGCATCCAGCGTAAGCCTTCCAGGGATCGT | A | 11 |
| R10-EF-23 | CAATCGAAGCTGCATCCAGCGTAAGCCTTCCAGGGATCGT | A | 11 |
| R10-EF-25 | CAATCGAAGCTGCATCCAGCGTAAGCCTTCCAGGGATCGT | A | 11 |
| R10-EF-26 | CAATCGAAGCTGCATCCAGCGTAAGCCTTCCAGGGATCGT | A | 11 |
| R10-EF-27 | CAATCGAAGCTGCATCCAGCGTAAGCCTTCCAGGGATCGT | A | 11 |
| R10-EF-32 | CAATCGAAGCTGCATCCAGCGTAAGCCTTCCAGGGATCGT | A | 11 |
| R10-EF-36 | CAATCGAAGCTGCATCCAGCGTAAGCCTTCCAGGGATCGT | A | 11 |
| R10-EF-37 | CAATCGAAGCTGCATCCAGCGTAAGCCTTCCAGGGATCGT | A | 11 |
| R10-EF-40 | CAATCGAAGCTGCATCCAGCGTAAGCCTTCCAGGGATCGT | A | 11 |
| | | | |
| R10-EF-31 | TCTAAGCTGCGTCTGGCATAAGCCTCACCTACTCGATACT | F | 12 |
| | | | |
| R10-EF-29 | TGCCAAAACACCCGTCTTGCATAAGCCTCCTACATAA | B | 13 |
| R10-EF-2 | TGCCAAAACACCCGTCTTGCATAAGCCTCCTACGGCAACT | B | 14 |
| R10-EF-7 | TGCCAAAACACCCGTCTTGCATAAGCCTCCTACGGCAACT | B | 14 |
| R10-EF-8 | TGCCAAAACACCCGTCTTGCATAAGCCTCCTACGGCAACT | B | 14 |
| R10-EF-10 | TGCCAAAACACCCGTCTTGCATAAGCCTCCTACGGCAACT | B | 14 |
| R10-EF-11 | TGCCAAAACACCCGTCTTGCATAAGCCTCCTACGGCAACT | B | 14 |
| R10-EF-12 | TGCCAAAACACCCGTCTTGCATAAGCCTCCTACGGCAACT | B | 14 |
| R10-EF-13 | TGCCAAAACACCCGTCTTGCATAAGCCTCCTACGGCAACT | B | 14 |
| R10-EF-16 | TGCCAAAACACCCGTCTTGCATAAGCCTCCTACGGCAACT | B | 14 |
| R10-EF-18 | TGCCAAAACACCCGTCTTGCATAAGCCTCCTACGGCAACT | B | 14 |
| R10-EF-19 | TGCCAAAACACCCGTCTTGCATAAGCCTCCTACGGCAACT | B | 14 |
| R10-EF-21 | TGCCAAAACACCCGTCTTGCATAAGCCTCCTACGGCAACT | B | 14 |
| R10-EF-24 | TGCCAAAACACCCGTCTTGCATAAGCCTCCTACGGCAACT | B | 14 |
| R10-EF-28 | TGCCAAAACACCCGTCTTGCATAAGCCTCCTACGGCAACT | B | 14 |
| R10-EF-30 | TGCCAAAACACCCGTCTTGCATAAGCCTCCTACGGCAACT | B | 14 |
| R10-EF-33 | TGCCAAAACACCCGTCTTGCATAAGCCTCCTACGGCAACT | B | 14 |
| R10-EF-38 | TGCCAAAACACCCGTCTTGCATAAGCCTCCTACGGCAACT | B | 14 |

Figure 4A

R10 E2 Sequences

| | Random Region | Sequence | SEQ ID NO: |
|---|---|---|---|
| R10-E2-6 | ATAGACCGCGTCTGGCATAAGCCTCCAAACACTCTGATCC | D | 15 |
| R10-E2-16 | ATCACACCGCGTCTTGCGTAAGCCTCCTACCAACGGATCG | C | 16 |
| R10-E2-14 | ATCACACCGCGTCTTGCGTAAGCCTCCTACTAACGGATCA | C | 17 |
| R10-E2-3 | ATCACACCGCGTCTTGCGTAAGCCTCCTACTAACGGATCG | C | 7 |
| R10-E2-11 | ATCACACCGCGTCTTGCGTAAGCCTCCTACTAACGGATCG | C | 7 |
| R10-E2-13 | ATCACACCGCGTCTTGCGTAAGCCTCCTACTAACGGATCG | C | 7 |
| R10-E2-20 | ATCACACCGCGTCTTGCGTAAGCCTCCTACTAACGGATCG | C | 7 |
| R10-E2-27 | ATCACACCGCGTCTTGCGTAAGCCTCCTACTAACGGATCG | C | 7 |
| R10-E2-29 | ATCACACCGCGTCTTGCGTAAGCCTCCTACTAACGGATCG | C | 7 |
| R10-E2-5 | ATCACACCGCGTCTTGCGTAAGCCTCCTACTAACGGATCT | C | 18 |
| R10-E2-9 | ATTCAACCCGCCTCTGGCATAAGCCTACCCATCGTGATTGT | E | 9 |
| R10-E2-19 | ATTCAACCCGCCTCTGGCATAAGCCTACCCATCGTGATTGT | E | 9 |
| R10-E2-24 | ATTCAACCCGCCTCTGGCATAAGCCTACCCATCGTGATTGT | E | 9 |
| R10-E2-30 | ATTCAACCCGCCTCTGGCATAAGCCTACCCATCGTGATTGT | E | 9 |
| R10-E2-34 | CAATCGAAGCTGCATCCAGCGTAAGCCTTCCAAGGATCGT | A | 19 |
| R10-E2-8 | CAATCGAAGCTGCATCCAGCGTAAGCCTTCCAGGGATCGT | A | 11 |
| R10-E2-10 | CAATCGAAGCTGCATCCAGCGTAAGCCTTCCAGGGATCGT | A | 11 |
| R10-E2-12 | CAATCGAAGCTGCATCCAGCGTAAGCCTTCCAGGGATCGT | A | 11 |
| R10-E2-18 | CAATCGAAGCTGCATCCAGCGTAAGCCTTCCAGGGATCGT | A | 11 |
| R10-E2-26 | CAATCGAAGCTGCATCCAGCGTAAGCCTTCCAGGGATCGT | A | 11 |
| R10-E2-28 | CAATCGAAGCTGCATCCAGCGTAAGCCTTCCAGGGATCGT | A | 11 |
| R10-E2-32 | CAATCGAAGCTGCATCCAGCGTAAGCCTTCCAGGGATCGT | A | 11 |
| R10-E2-33 | CAATCGAAGCTGCATCCAGCGTAAGCCTTCCAGGGATCGT | A | 11 |
| R10-E2-35 | CAATCGAAGCTGCATCCAGCGTAAGCCTTCCAGGGATCGT | A | 11 |
| R10-E2-36 | TGCCAAAACACCCGTCTTGCATAAGCCTCCTACGGCAAAT | B | 20 |
| R10-E2-1 | TGCCAAAACACCCGTCTTGCATAAGCCTCCTACGGCAACT | B | 14 |
| R10-E2-2 | TGCCAAAACACCCGTCTTGCATAAGCCTCCTACGGCAACT | B | 14 |
| R10-E2-4 | TGCCAAAACACCCGTCTTGCATAAGCCTCCTACGGCAACT | B | 14 |
| R10-E2-7 | TGCCAAAACACCCGTCTTGCATAAGCCTCCTACGGCAACT | B | 14 |
| R10-E2-15 | TGCCAAAACACCCGTCTTGCATAAGCCTCCTACGGCAACT | B | 14 |
| R10-E2-17 | TGCCAAAACACCCGTCTTGCATAAGCCTCCTACGGCAACT | B | 14 |
| R10-E2-21 | TGCCAAAACACCCGTCTTGCATAAGCCTCCTACGGCAACT | B | 14 |
| R10-E2-22 | TGCCAAAACACCCGTCTTGCATAAGCCTCCTACGGCAACT | B | 14 |
| R10-E2-23 | TGCCAAAACACCCGTCTTGCATAAGCCTCCTACGGCAACT | B | 14 |
| R10-E2-31 | TGCCAAAACACCCGTCTTGCATAAGCCTCCTACGGCAACT | B | 14 |
| R10-E2-37 | TGCCAAAACACCCGTCTTGCATAAGCCTCCTACGGCAACT | B | 14 |
| R10-E2-38 | TGCCAAAACACCCGTCTTGCATAAGCCTCCTACGGCAACT | B | 14 |
| R10-E2-39 | TGCCAAAACACCCGTCTTGCATAAGCCTCCTACGGCAACT | B | 14 |
| R10-E2-40 | TGCCAAAACACCCGTCTTGCATAAGCCTCCTACGGCAACT | B | 14 |
| R10-E2-25 | TGCCAAAACGCCCGTCTTGCATAAGCCTCCTACGGCAACT | B | 21 |

Figure 4B

Clone Family

| Clone Family | | S1 | L1 | S2 | S2 | L2 | S2 | L3 | S3 | L4 | S3 | S1 | | |
|---|---|---|---|---|---|---|---|---|---|---|---|---|---|---|
| EF-2 | 5' | GGGAG | GAC | GAUGCGGUG | CCAAAAA | CACCCGUC | UU | GC | AUAA | GC | CUCCU | 3' | SEQ ID NO:36 |
| EF-3 | 5' | GGGAG | GAC | GAUGCGG | AUCACA | CCGCGUC | UU | GC | GUAA | GC | CUCCU | 3' | SEQ ID NO:40 |
| EF-1 | 5' | GGGAG | GAC | GAUGCGGC | AAUCGAA | GCUGCAUC | CA | GC | GUAA | GC | CUUCC | 3' | SEQ ID NO:34 |
| EF-22 | 5' | GGGAG | GAC | GAUGCGG | AUUCAAC | CCGCCUC | UG | GC | AUAA | GC | CUACCC | 3' | SEQ ID NO:53 |
| E2-6 | 5' | GGAG | GAC | GAUGCGG | AUAGA | CCGCGUC | UG | GC | AUAA | GC | CUCC | 3' | SEQ ID NO:96 |
| EF-31 | 5' | GGGAG | GAC | GAUGCGGU | CUAA | GCUGCGUC | UG | GC | AUAA | GC | CUCACC | 3' | SEQ ID NO:55 |

Figure 5

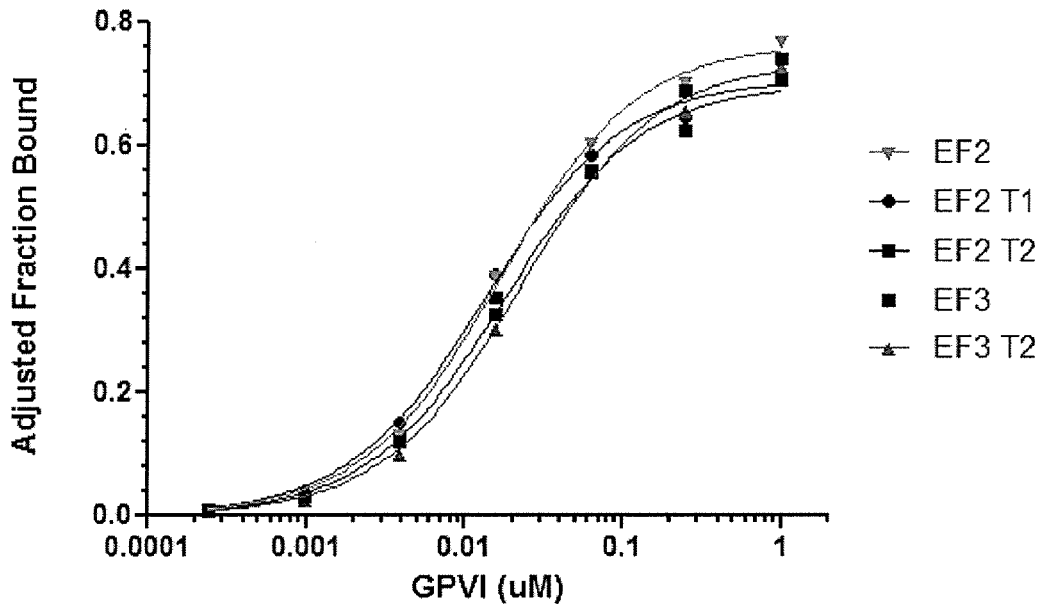
Figure 7
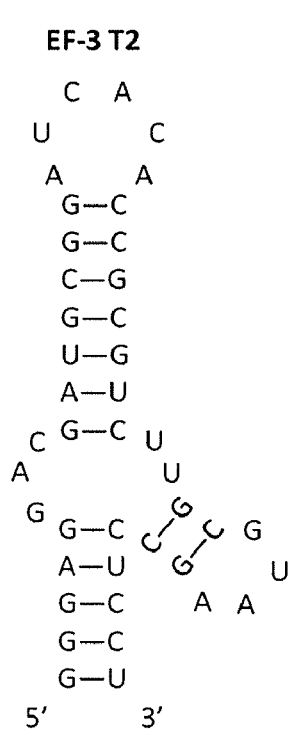
SEQ ID NO: 40
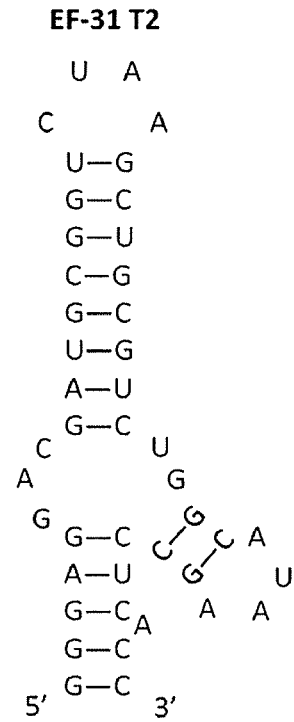
SEQ ID NO: 55
Figure 8A

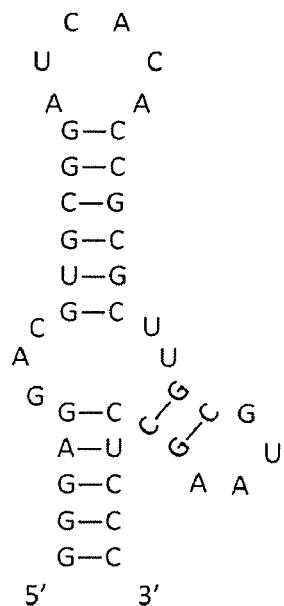
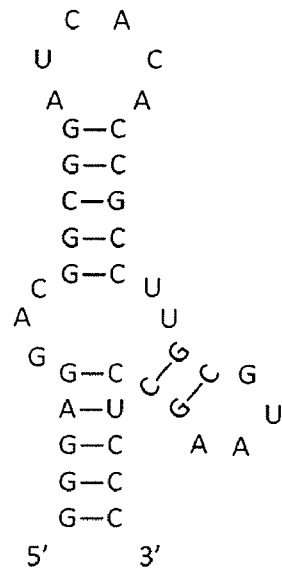
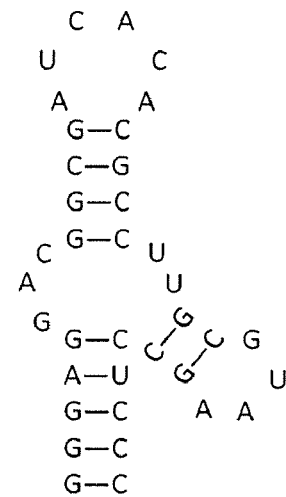
Figure 8B
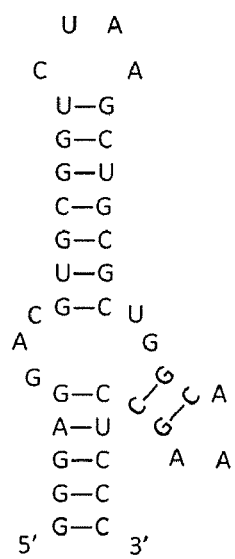
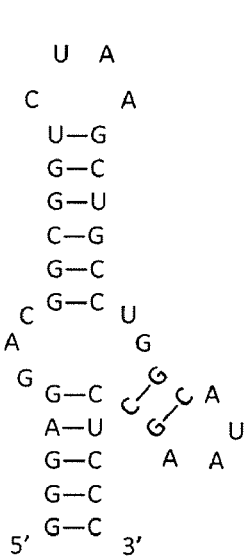
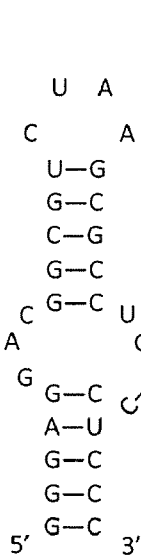
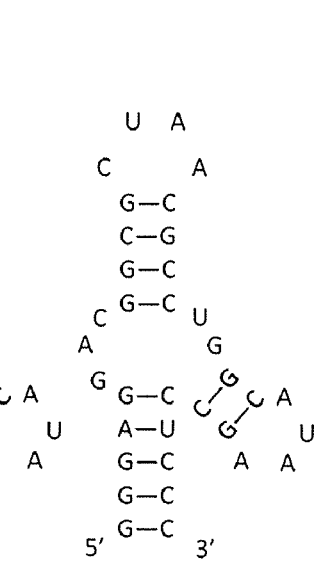
Figure 8C

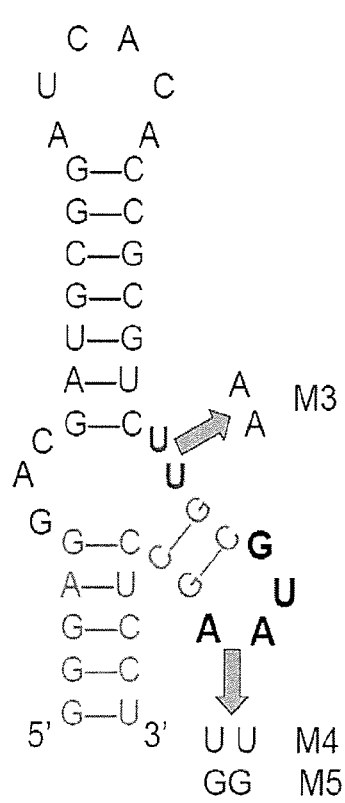
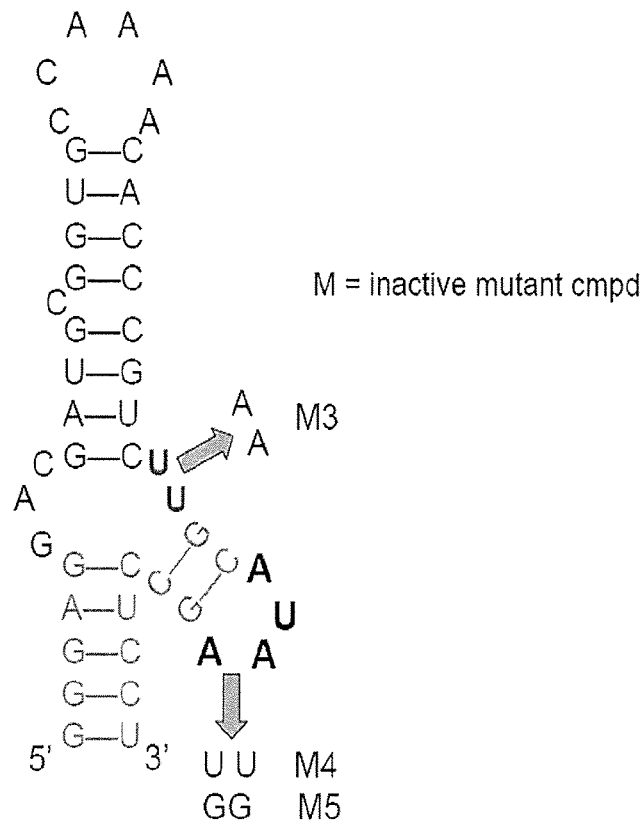
Figure 9

RB526
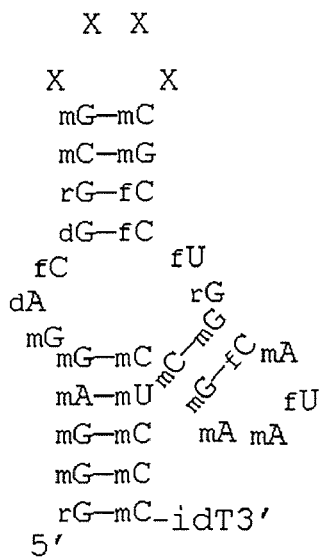
SEQ ID NO: 63
RB537
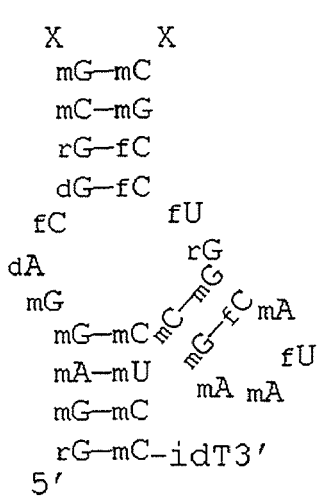
SEQ ID NO: 69
RB538
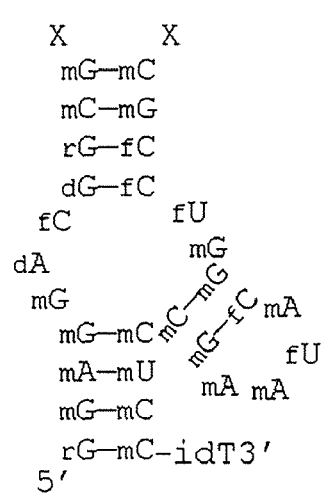
SEQ ID NO: 69
Figure 11C
RB540
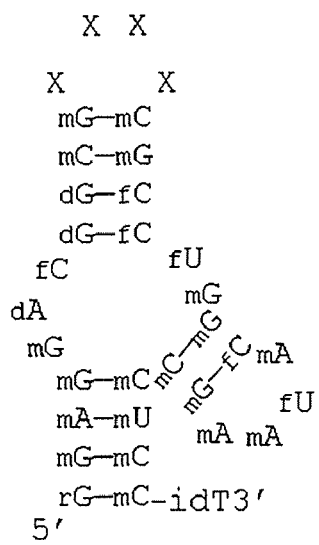
SEQ ID NO: 69
RB566
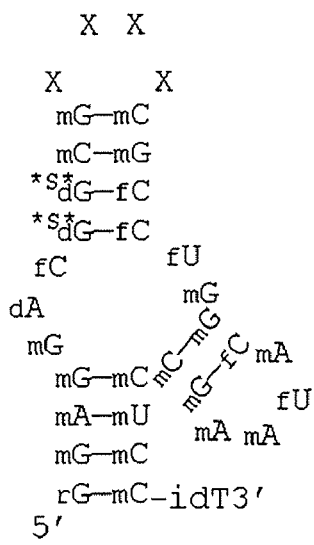
SEQ ID NO: 69
RB571
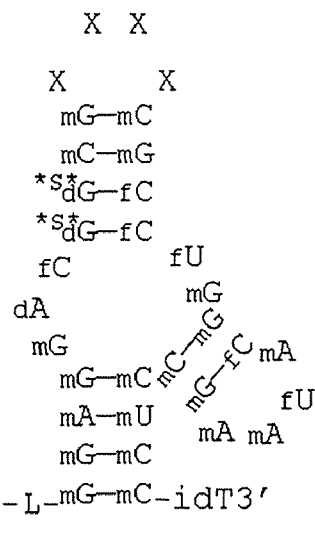
SEQ ID NO: 69
Figure 11D

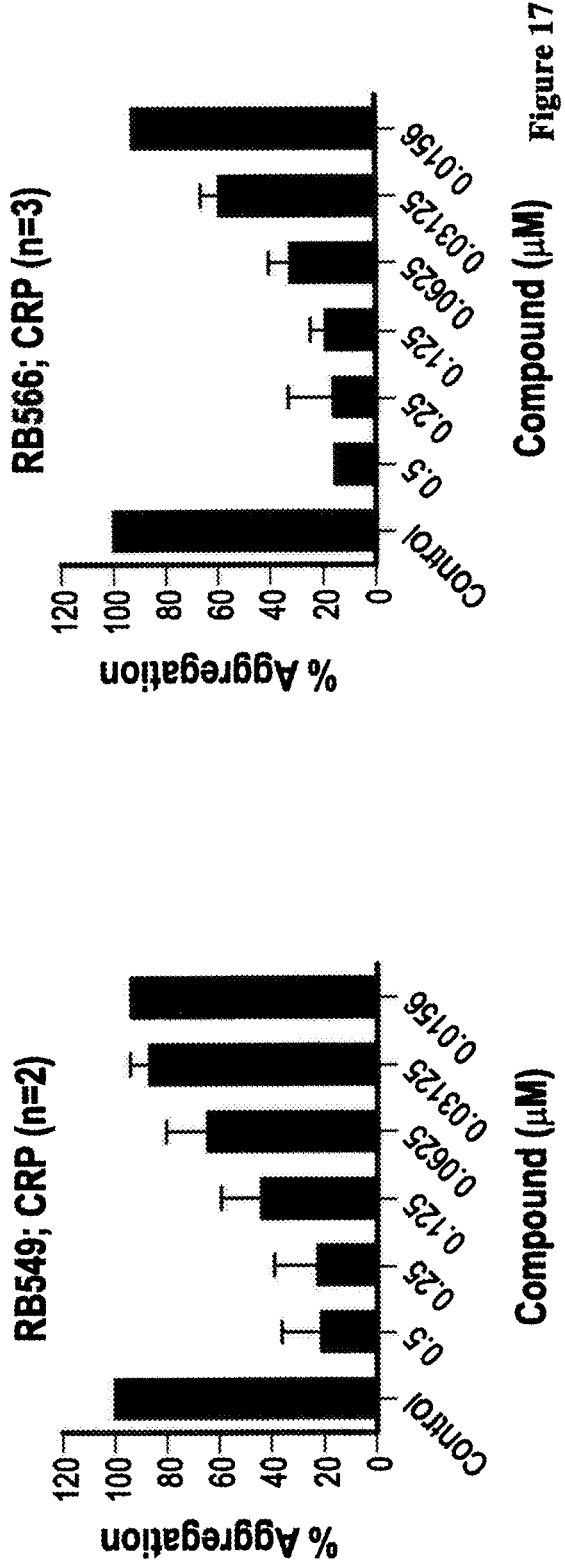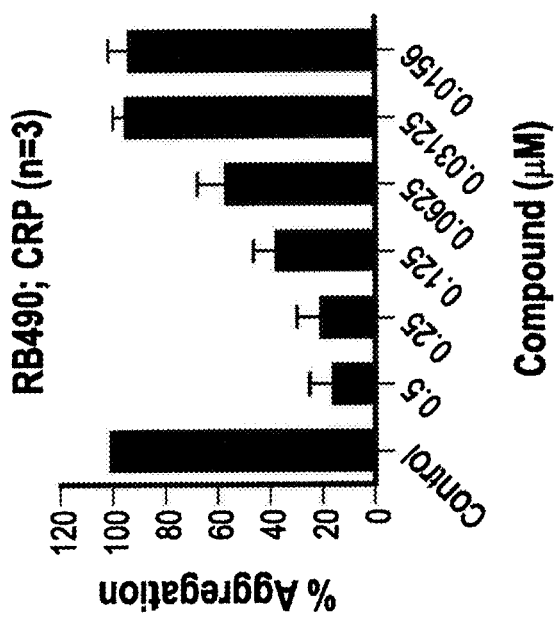
Figure 17

HIP1= anti-GP1bα mAb

SEQUENCE LISTING

<160> NUMBER OF SEQ ID NOS: 96

<210> SEQ ID NO 1
<211> LENGTH: 339
<212> TYPE: PRT
<213> ORGANISM: Homo sapiens

<400> SEQUENCE: 1

```
Met Ser Pro Ser Pro Thr Ala Leu Phe Cys Leu Gly Leu Cys Leu Gly
1               5                   10                  15

Arg Val Pro Ala Gln Ser Gly Pro Leu Pro Lys Pro Ser Leu Gln Ala
            20                  25                  30

Leu Pro Ser Ser Leu Val Pro Leu Glu Lys Pro Val Thr Leu Arg Cys
        35                  40                  45

Gln Gly Pro Pro Gly Val Asp Leu Tyr Arg Leu Glu Lys Leu Ser Ser
    50                  55                  60

Ser Arg Tyr Gln Asp Gln Ala Val Leu Phe Ile Pro Ala Met Lys Arg
65                  70                  75                  80

Ser Leu Ala Gly Arg Tyr Arg Cys Ser Tyr Gln Asn Gly Ser Leu Trp
                85                  90                  95

Ser Leu Pro Ser Asp Gln Leu Glu Leu Val Ala Thr Gly Val Phe Ala
            100                 105                 110

Lys Pro Ser Leu Ser Ala Gln Pro Gly Pro Ala Val Ser Ser Gly Gly
        115                 120                 125

Asp Val Thr Leu Gln Cys Gln Thr Arg Tyr Gly Phe Asp Gln Phe Ala
    130                 135                 140

Leu Tyr Lys Glu Gly Asp Pro Ala Pro Tyr Lys Asn Pro Glu Arg Trp
145                 150                 155                 160

Tyr Arg Ala Ser Phe Pro Ile Ile Thr Val Thr Ala Ala His Ser Gly
                165                 170                 175

Thr Tyr Arg Cys Tyr Ser Phe Ser Ser Arg Asp Pro Tyr Leu Trp Ser
            180                 185                 190

Ala Pro Ser Asp Pro Leu Glu Leu Val Val Thr Gly Thr Ser Val Thr
        195                 200                 205

Pro Ser Arg Leu Pro Thr Glu Pro Pro Ser Ser Val Ala Glu Phe Ser
    210                 215                 220

Glu Ala Thr Ala Glu Leu Thr Val Ser Phe Thr Asn Lys Val Phe Thr
225                 230                 235                 240

Thr Glu Thr Ser Arg Ser Ile Thr Thr Ser Pro Lys Glu Ser Asp Ser
                245                 250                 255

Pro Ala Gly Pro Ala Arg Gln Tyr Tyr Thr Lys Gly Asn Leu Val Arg
            260                 265                 270

Ile Cys Leu Gly Ala Val Ile Leu Ile Ile Leu Ala Gly Phe Leu Ala
        275                 280                 285

Glu Asp Trp His Ser Arg Arg Lys Arg Leu Arg His Arg Gly Arg Ala
    290                 295                 300

Val Gln Arg Pro Leu Pro Pro Leu Pro Pro Leu Pro Gln Thr Arg Lys
305                 310                 315                 320
```

Ser His Gly Gly Gln Asp Gly Gly Arg Gln Asp Val His Ser Arg Gly
                325                 330                 335

Leu Cys Ser

<210> SEQ ID NO 2
<211> LENGTH: 319
<212> TYPE: PRT
<213> ORGANISM: Homo sapiens

<400> SEQUENCE: 2

Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys Gly Asn Leu Val Arg Ile Cys Leu Gly
                245                 250                 255

Ala Val Ile Leu Ile Ile Leu Ala Gly Phe Leu Ala Glu Asp Trp His
            260                 265                 270

Ser Arg Arg Lys Arg Leu Arg His Arg Gly Arg Ala Val Gln Arg Pro
        275                 280                 285

Leu Pro Pro Leu Pro Pro Leu Pro Gln Thr Arg Lys Ser His Gly Gly
    290                 295                 300

Gln Asp Gly Gly Arg Gln Asp Val His Ser Arg Gly Leu Cys Ser
305                 310                 315

<210> SEQ ID NO 3
<211> LENGTH: 253
<212> TYPE: PRT
<213> ORGANISM: Artificial sequence
<220> FEATURE:

<223> OTHER INFORMATION: GPVI Extracellular domain with His tag

<400> SEQUENCE: 3

```
Gln Ser Gly Pro Leu Pro Lys Pro Ser Leu Gln Ala Leu Pro Ser Ser
1               5                   10                  15

Leu Val Pro Leu Glu Lys Pro Val Thr Leu Arg Cys Gln Gly Pro Pro
            20                  25                  30

Gly Val Asp Leu Tyr Arg Leu Glu Lys Leu Ser Ser Ser Arg Tyr Gln
        35                  40                  45

Asp Gln Ala Val Leu Phe Ile Pro Ala Met Lys Arg Ser Leu Ala Gly
    50                  55                  60

Arg Tyr Arg Cys Ser Tyr Gln Asn Gly Ser Leu Trp Ser Leu Pro Ser
65                  70                  75                  80

Asp Gln Leu Glu Leu Val Ala Thr Gly Val Phe Ala Lys Pro Ser Leu
                85                  90                  95

Ser Ala Gln Pro Gly Pro Ala Val Ser Ser Gly Gly Asp Val Thr Leu
            100                 105                 110

Gln Cys Gln Thr Arg Tyr Gly Phe Asp Gln Phe Ala Leu Tyr Lys Glu
        115                 120                 125

Gly Asp Pro Ala Pro Tyr Lys Asn Pro Glu Arg Trp Tyr Arg Ala Ser
    130                 135                 140

Phe Pro Ile Ile Thr Val Thr Ala Ala His Ser Gly Thr Tyr Arg Cys
145                 150                 155                 160

Tyr Ser Phe Ser Ser Arg Asp Pro Tyr Leu Trp Ser Ala Pro Ser Asp
                165                 170                 175

Pro Leu Glu Leu Val Val Thr Gly Thr Ser Val Thr Pro Ser Arg Leu
            180                 185                 190

Pro Thr Glu Pro Pro Ser Ser Val Ala Glu Phe Ser Glu Ala Thr Ala
        195                 200                 205

Glu Leu Thr Val Ser Phe Thr Asn Lys Val Phe Thr Thr Glu Thr Ser
    210                 215                 220

Arg Ser Ile Thr Thr Ser Pro Lys Glu Ser Asp Ser Pro Ala Gly Pro
225                 230                 235                 240

Ala Arg Gln Tyr Tyr Thr Lys His His His His His His
                245                 250
```

<210> SEQ ID NO 4
<211> LENGTH: 82
<212> TYPE: DNA
<213> ORGANISM: Artificial Sequence
<220> FEATURE:
<223> OTHER INFORMATION: Synthetic Oligonucleotide Template Sequence for Library Screen
<220> FEATURE:
<221> NAME/KEY: misc_feature
<222> LOCATION: (26)..(65)
<223> OTHER INFORMATION: N is A, T, G, or C

<400> SEQUENCE: 4
tctcggatcc tcagcgagtc gtctgnnnnn nnnnnnnnnn nnnnnnnnnn nnnnnnnnnn    60
nnnnnccgca tcgtcctccc ta                                             82

<210> SEQ ID NO 5
<211> LENGTH: 42
<212> TYPE: DNA
<213> ORGANISM: Artificial Sequence
<220> FEATURE:
<223> OTHER INFORMATION: Synthetic Oligonucleotide Primer for library screen template

```
<400> SEQUENCE: 5
gggggaattc taatacgact cactataggg aggacgatgc gg                     42

<210> SEQ ID NO 6
<211> LENGTH: 25
<212> TYPE: DNA
<213> ORGANISM: Artificial sequence
<220> FEATURE:
<223> OTHER INFORMATION: Primer for library screen template

<400> SEQUENCE: 6
tctcggatcc tcagcgagtc gtctg                                       25

<210> SEQ ID NO 7
<211> LENGTH: 40
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 7
atcacaccgc gtcttgcgta agcctcctac taacggatcg                       40

<210> SEQ ID NO 8
<211> LENGTH: 39
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 8
atcacccgcg tcttgcgtaa gcctcctact aacggatcg                        39

<210> SEQ ID NO 9
<211> LENGTH: 41
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 9
attcaacccg cctctggcat aagcctaccc atcgtgattg t                     41

<210> SEQ ID NO 10
<211> LENGTH: 40
<212> TYPE: DNA
<213> ORGANISM: Artificial sequence
<220> FEATURE:
<223> OTHER INFORMATION: Synthetic oligonucleotide random region of R10
      selected sequence

<400> SEQUENCE: 10
caatcgaagc tgcatccagc gtaagccttc cagggaccgt                       40

<210> SEQ ID NO 11
<211> LENGTH: 40
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 11
caatcgaagc tgcatccagc gtaagccttc caggatcgt                        40
```

<210> SEQ ID NO 12
<211> LENGTH: 40
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 12
tctaagctgc gtctggcata agcctcacct actcgatact                              40

<210> SEQ ID NO 13
<211> LENGTH: 37
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 13
tgccaaaaca cccgtcttgc ataagcctcc tacataa                                 37

<210> SEQ ID NO 14
<211> LENGTH: 40
<212> TYPE: DNA
<213> ORGANISM: Artificial sequence
<220> FEATURE:
<223> OTHER INFORMATION: Synthetic oligonucleotide random region of R10
      selected sequence

<400> SEQUENCE: 14
tgccaaaaca cccgtcttgc ataagcctcc tacggcaact                              40

<210> SEQ ID NO 15
<211> LENGTH: 40
<212> TYPE: DNA
<213> ORGANISM: Artificial sequence
<220> FEATURE:
<223> OTHER INFORMATION: Synthetic oligonucleotide random region of R10
      selected sequence

<400> SEQUENCE: 15
atagaccgcg tctggcataa gcctccaaac actctgatcc                              40

<210> SEQ ID NO 16
<211> LENGTH: 40
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 16
atcacaccgc gtcttgcgta agcctcctac caacggatcg                              40

<210> SEQ ID NO 17
<211> LENGTH: 40
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 17
atcacaccgc gtcttgcgta agcctcctac taacggatca                              40

```
<210> SEQ ID NO 18
<211> LENGTH: 40
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 18
atcacaccgc gtcttgcgta agcctcctac taacggatct                              40

<210> SEQ ID NO 19
<211> LENGTH: 40
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 19
caatcgaagc tgcatccagc gtaagccttc caaggatcgt                              40

<210> SEQ ID NO 20
<211> LENGTH: 40
<212> TYPE: DNA
<213> ORGANISM: Artificial sequence
<220> FEATURE:
<223> OTHER INFORMATION: Synthetic Oligonucleotide Synthetic
      oligonucleotide random region of R10 selected sequence

<400> SEQUENCE: 20
tgccaaaaca cccgtcttgc ataagcctcc tacggcaaat                              40

<210> SEQ ID NO 21
<211> LENGTH: 40
<212> TYPE: DNA
<213> ORGANISM: Artificial sequence
<220> FEATURE:
<223> OTHER INFORMATION: Synthetic Oligonucleotide Random region of R10
      selected sequence

<400> SEQUENCE: 21
tgccaaaacg cccgtcttgc ataagcctcc tacggcaact                              40

<210> SEQ ID NO 22
<211> LENGTH: 80
<212> TYPE: DNA
<213> ORGANISM: Artificial sequence
<220> FEATURE:
<223> OTHER INFORMATION: Synthetic Oligonucleotide EF-1 DNA

<400> SEQUENCE: 22
gggaggacga tgcggcaatc gaagctgcat ccagcgtaag ccttccaggg atcgtcagac        60
gactcgctga ggatccgaga                                                    80

<210> SEQ ID NO 23
<211> LENGTH: 80
<212> TYPE: DNA
<213> ORGANISM: Artificial sequence
<220> FEATURE:
<223> OTHER INFORMATION: Synthetic Oligonucleotide EF-2 DNA

<400> SEQUENCE: 23
gggaggacga tgcggtgcca aacacccgt cttgcataag cctcctacgg caactcagac         60
gactcgctga ggatccgaga                                                    80
```

```
<210> SEQ ID NO 24
<211> LENGTH: 80
<212> TYPE: DNA
<213> ORGANISM: Artificial sequence
<220> FEATURE:
<223> OTHER INFORMATION: Synthetic Oligonucleotide EF-3 DNA

<400> SEQUENCE: 24
gggaggacga tgcggatcac accgcgtctt gcgtaagcct cctactaacg gatcgcagac     60
gactcgctga ggatccgaga                                                  80

<210> SEQ ID NO 25
<211> LENGTH: 80
<212> TYPE: DNA
<213> ORGANISM: Artificial sequence
<220> FEATURE:
<223> OTHER INFORMATION: Synthetic Oligonucleotide E2-6 DNA

<400> SEQUENCE: 25
gggaggacga tgcggataga ccgcgtctgg cataagcctc aaacactct gatcccagac      60 gactcgctga ggatccgaga                                                  80

<210> SEQ ID NO 26
<211> LENGTH: 81
<212> TYPE: DNA
<213> ORGANISM: Artificial sequence
<220> FEATURE:
<223> OTHER INFORMATION: Synthetic Oligonucleotide EF-22 DNA

<400> SEQUENCE: 26
gggaggacga tgcggattca acccgcctct ggcataagcc tacccatcgt gattgtcaga     60
cgactcgctg aggatccgag a                                                81

<210> SEQ ID NO 27
<211> LENGTH: 80
<212> TYPE: DNA
<213> ORGANISM: Artificial sequence
<220> FEATURE:
<223> OTHER INFORMATION: Synthetic Oligonucleotide EF-31 DNA

<400> SEQUENCE: 27
gggaggacga tgcggtctaa gctgcgtctg gcataagcct cacctactcg atactcagac     60
gactcgctga ggatccgaga                                                  80

<210> SEQ ID NO 28
<211> LENGTH: 80
<212> TYPE: RNA
<213> ORGANISM: Artificial sequence
<220> FEATURE:
<223> OTHER INFORMATION: Synthetic Oligonucleotide EF-1 full length RNA

<400> SEQUENCE: 28
gggaggacga ugcggcaauc gaagcugcau ccagcguaag ccuuccaggg aucgucagac     60
gacucgcuga ggauccgaga                                                  80

<210> SEQ ID NO 29
<211> LENGTH: 80
<212> TYPE: RNA
<213> ORGANISM: Artificial sequence
<220> FEATURE:
<223> OTHER INFORMATION: Synthetic Oligonucleotide EF-2 full length RNA

<400> SEQUENCE: 29
gggaggacga ugcggugcca aaacacccgu cuugcauaag ccuccuacgg caacucagac     60
```

-continued

```
gacucgcuga ggauccgaga                                              80

<210> SEQ ID NO 30
<211> LENGTH: 80
<212> TYPE: RNA
<213> ORGANISM: Artificial sequence
<220> FEATURE:
<223> OTHER INFORMATION: Synthetic Oligonucleotide EF-3 full length RNA

<400> SEQUENCE: 30
gggaggacga ugcggaucac accgcgucuu gcguaagccu ccuacuaacg gaucgcagac    60
gacucgcuga ggauccgaga                                              80

<210> SEQ ID NO 31
<211> LENGTH: 80
<212> TYPE: RNA
<213> ORGANISM: Artificial sequence
<220> FEATURE:
<223> OTHER INFORMATION: Synthetic Oligonucleotide E2-6  full length RNA

<400> SEQUENCE: 31
gggaggacga ugcggauaga ccgcgucugg cauaagccuc caaacacucu gaucccagac    60
gacucgcuga ggauccgaga                                              80

<210> SEQ ID NO 32
<211> LENGTH: 81
<212> TYPE: RNA
<213> ORGANISM: Artificial sequence
<220> FEATURE:
<223> OTHER INFORMATION: Synthetic Oligonucleotide EF-22 full length RNA

<400> SEQUENCE: 32
gggaggacga ugcggauuca acccgccucu ggcauaagcc uacccaucgu gauugucaga    60
cgacucgcug aggauccgag a                                            81

<210> SEQ ID NO 33
<211> LENGTH: 80
<212> TYPE: RNA
<213> ORGANISM: Artificial sequence
<220> FEATURE:
<223> OTHER INFORMATION: Synthetic Oligonucleotide EF-31 full length RNA

<400> SEQUENCE: 33
gggaggacga ugcggucuaa gcugcgucug gcauaagccu caccuacucg auacucagac    60
gacucgcuga ggauccgaga                                              80

<210> SEQ ID NO 34
<211> LENGTH: 46
<212> TYPE: RNA
<213> ORGANISM: Artificial sequence
<220> FEATURE:
<223> OTHER INFORMATION: Synthetic Oligonucleotide EF-1 T1

<400> SEQUENCE: 34
gggaggacga ugcggcaauc gaagcugcau ccagcguaag ccuucc                  46

<210> SEQ ID NO 35
<211> LENGTH: 55
<212> TYPE: RNA
<213> ORGANISM: Artificial sequence
<220> FEATURE:
<223> OTHER INFORMATION: Synthetic Oligonucleotide EF-2 T1

<400> SEQUENCE: 35
```
gggaggacga ugcggugcca aaacacccgu cuugcauaag ccuccuacgg caacu    55

<210> SEQ ID NO 36
<211> LENGTH: 46
<212> TYPE: RNA
<213> ORGANISM: Artificial sequence
<220> FEATURE:
<223> OTHER INFORMATION: Synthetic Oligonucleotide EF-2 T2

<400> SEQUENCE: 36
gggaggacga ugcggugcca aaacacccgu cuugcauaag ccuccu    46

<210> SEQ ID NO 37
<211> LENGTH: 46
<212> TYPE: RNA
<213> ORGANISM: Artificial sequence
<220> FEATURE:
<223> OTHER INFORMATION: Synthetic Oligonucleotide EF-2-T2 mut3

<400> SEQUENCE: 37
gggaggacga ugcggugcca aaacacccgu caagcauaag ccuccu    46

<210> SEQ ID NO 38
<211> LENGTH: 46
<212> TYPE: RNA
<213> ORGANISM: Artificial sequence
<220> FEATURE:
<223> OTHER INFORMATION: Synthetic Oligonucleotide EF-2-T2 mut4

<400> SEQUENCE: 38
gggaggacga ugcggugcca aaacacccgu cuugcauuug ccuccu    46

<210> SEQ ID NO 39
<211> LENGTH: 46
<212> TYPE: RNA
<213> ORGANISM: Artificial sequence
<220> FEATURE:
<223> OTHER INFORMATION: Synthetic Oligonucleotide EF-2-T2 mut5

<400> SEQUENCE: 39
gggaggacga ugcggugcca aaacacccgu cuugcauggg ccuccu    46

<210> SEQ ID NO 40
<211> LENGTH: 43
<212> TYPE: RNA
<213> ORGANISM: Artificial sequence
<220> FEATURE:
<223> OTHER INFORMATION: Synthetic Oligonucleotide EF-3 T2

<400> SEQUENCE: 40
gggaggacga ugcggaucac accgcgucuu gcguaagccu ccu    43

<210> SEQ ID NO 41
<211> LENGTH: 41
<212> TYPE: RNA
<213> ORGANISM: Artificial sequence
<220> FEATURE:
<223> OTHER INFORMATION: Synthetic Oligonucleotide EF-3 T3

<400> SEQUENCE: 41
gggaggacgu gcggaucaca ccgcgcuugc guaagccucc c    41

<210> SEQ ID NO 42
<211> LENGTH: 39
<212> TYPE: RNA
<213> ORGANISM: Artificial sequence

```
<220> FEATURE:
<223> OTHER INFORMATION: Synthetic Oligonucleotide EF-3 T4

<400> SEQUENCE: 42
gggaggacgg cggaucacac cgccuugcgu aagccuccc                                39

<210> SEQ ID NO 43
<211> LENGTH: 37
<212> TYPE: RNA
<213> ORGANISM: Artificial sequence
<220> FEATURE:
<223> OTHER INFORMATION: Synthetic Oligonucleotide EF-3 T5

<400> SEQUENCE: 43
gggaggacgg cgaucacacg ccuugcguaa gccuccc                                  37

<210> SEQ ID NO 44
<211> LENGTH: 43
<212> TYPE: RNA
<213> ORGANISM: Artificial sequence
<220> FEATURE:
<223> OTHER INFORMATION: Synthetic Oligonucleotide EF-3 T2 mut3

<400> SEQUENCE: 44
gggaggacga ugcggaucac accgcgucaa gcguaagccu ccu                           43

<210> SEQ ID NO 45
<211> LENGTH: 43
<212> TYPE: RNA
<213> ORGANISM: Artificial sequence
<220> FEATURE:
<223> OTHER INFORMATION: Synthetic Oligonucleotide EF-3 T2 mut4

<400> SEQUENCE: 45
gggaggacga ugcggaucac accgcgucuu gcguuugccu ccu                           43

<210> SEQ ID NO 46
<211> LENGTH: 43
<212> TYPE: RNA
<213> ORGANISM: Artificial sequence
<220> FEATURE:
<223> OTHER INFORMATION: Synthetic Oligonucleotide EF-3 T2 mut5

<400> SEQUENCE: 46
gggaggacga ugcggaucac accgcgucuu gcgugggccu ccu                           43

<210> SEQ ID NO 47
<211> LENGTH: 43
<212> TYPE: RNA
<213> ORGANISM: Artificial sequence
<220> FEATURE:
<223> OTHER INFORMATION: Synthetic Oligonucleotide EF-3 T2 mut6

<400> SEQUENCE: 47
gggaggacga ugcggaucac accgcgucua gcguaagccu ccu                           43

<210> SEQ ID NO 48
<211> LENGTH: 43
<212> TYPE: RNA
<213> ORGANISM: Artificial sequence
<220> FEATURE:
<223> OTHER INFORMATION: Synthetic Oligonucleotide EF-3 T2 mut7

<400> SEQUENCE: 48
gggaggacga ugcggaucac accgcgucau gcguaagccu ccu                           43
```

-continued

```
<210> SEQ ID NO 49
<211> LENGTH: 37
<212> TYPE: RNA
<213> ORGANISM: Artificial sequence
<220> FEATURE:
<223> OTHER INFORMATION: Synthetic Oligonucleotide EF-3 T5 mut8

<400> SEQUENCE: 49
gggaggacgg cgaucacacg ccuggcguaa gccuccc                                37

<210> SEQ ID NO 50
<211> LENGTH: 37
<212> TYPE: RNA
<213> ORGANISM: Artificial sequence
<220> FEATURE:
<223> OTHER INFORMATION: Synthetic Oligonucleotide EF-3 T5 mut9

<400> SEQUENCE: 50
gggaggacgg cgaucacacg ccuugcauaa gccuccc                                37

<210> SEQ ID NO 51
<211> LENGTH: 37
<212> TYPE: RNA
<213> ORGANISM: Artificial sequence
<220> FEATURE:
<223> OTHER INFORMATION: Synthetic Oligonucleotide EF-3 T5 mut10

<400> SEQUENCE: 51
gggaggacgg cgaucacacg ccuggcauaa gccuccc                                37

<210> SEQ ID NO 52
<211> LENGTH: 41
<212> TYPE: RNA
<213> ORGANISM: Artificial sequence
<220> FEATURE:
<223> OTHER INFORMATION: Synthetic Oligonucleotide E2-6 T1

<400> SEQUENCE: 52
gggaggacga ugcggauaga ccgcgucugg cauaagccuc c                           41

<210> SEQ ID NO 53
<211> LENGTH: 45
<212> TYPE: RNA
<213> ORGANISM: Artificial sequence
<220> FEATURE:
<223> OTHER INFORMATION: Synthetic Oligonucleotide EF-22 T1

<400> SEQUENCE: 53
gggaggacga ugcggauuca acccgccucu ggcauaagcc uaccc                       45

<210> SEQ ID NO 54
<211> LENGTH: 48
<212> TYPE: RNA
<213> ORGANISM: Artificial sequence
<220> FEATURE:
<223> OTHER INFORMATION: Synthetic Oligonucleotide EF-31 T1

<400> SEQUENCE: 54
gggaggacga ugcggucuaa gcugcgucug gcauaagccu caccuacu                    48

<210> SEQ ID NO 55
<211> LENGTH: 44
<212> TYPE: RNA
<213> ORGANISM: Artificial sequence
<220> FEATURE:
<223> OTHER INFORMATION: Synthetic Oligonucleotide EF-31 T2

<400> SEQUENCE: 55
```
gggaggacga ugcggucuaa gcugcgucug gcauaagccu cacc     44

<210> SEQ ID NO 56
<211> LENGTH: 43
<212> TYPE: RNA
<213> ORGANISM: Artificial sequence
<220> FEATURE:
<223> OTHER INFORMATION: Synthetic Oligonucleotide EF-31 T3

<400> SEQUENCE: 56
gggaggacga ugcggucuaa gcugcgucug gcauaagccu ccc     43

<210> SEQ ID NO 57
<211> LENGTH: 41
<212> TYPE: RNA
<213> ORGANISM: Artificial sequence
<220> FEATURE:
<223> OTHER INFORMATION: Synthetic Oligonucleotide EF-31 T4

<400> SEQUENCE: 57
gggaggacgu gcggucuaag cugcgcuggc auaagccucc c     41

<210> SEQ ID NO 58
<211> LENGTH: 39
<212> TYPE: RNA
<213> ORGANISM: Artificial sequence
<220> FEATURE:
<223> OTHER INFORMATION: Synthetic Oligonucleotide EF-31 T5

<400> SEQUENCE: 58
gggaggacgg cggucuaagc ugccuggcau aagccuccc     39

<210> SEQ ID NO 59
<211> LENGTH: 37
<212> TYPE: RNA
<213> ORGANISM: Artificial sequence
<220> FEATURE:
<223> OTHER INFORMATION: Synthetic Oligonucleotide EF-31 T6

<400> SEQUENCE: 59
gggaggacgg cgucuaagcg ccuggcauaa gccuccc     37

<210> SEQ ID NO 60
<211> LENGTH: 35
<212> TYPE: RNA
<213> ORGANISM: Artificial sequence
<220> FEATURE:
<223> OTHER INFORMATION: Synthetic Oligonucleotide EF-31 T7

<400> SEQUENCE: 60
gggaggacgg cgcuaacgcc uggcauaagc cuccc     35

<210> SEQ ID NO 61
<211> LENGTH: 33
<212> TYPE: RNA
<213> ORGANISM: Artificial sequence
<220> FEATURE:
<223> OTHER INFORMATION: Synthetic Oligonucleotide EF-31 T8

<400> SEQUENCE: 61
gggaggacgg ccuaagccug gcauaagccu ccc     33

<210> SEQ ID NO 62
<211> LENGTH: 35
<212> TYPE: RNA
<213> ORGANISM: Artificial sequence

```
<220> FEATURE:
<223> OTHER INFORMATION: Synthetic Oligonucleotide Modification of RB448

<400> SEQUENCE: 62
gggaggacgg cgcuaacgcc uggcauaagc cuccc                                    35

<210> SEQ ID NO 63
<211> LENGTH: 31
<212> TYPE: RNA
<213> ORGANISM: Artificial sequence
<220> FEATURE:
<223> OTHER INFORMATION: Synthetic Oligonucleotide Modification of RB448
<220> FEATURE:
<221> NAME/KEY: misc_feature
<222> LOCATION: (12)..(12)
<223> OTHER INFORMATION: a spacer is incorporated between positions 12
      and 13

<400> SEQUENCE: 63
gggaggacgg cgcgccuggc auaagccucc c                                        31

<210> SEQ ID NO 64
<211> LENGTH: 35
<212> TYPE: RNA
<213> ORGANISM: Artificial sequence
<220> FEATURE:
<223> OTHER INFORMATION: Synthetic Oligonucleotide Modification of RB448

<400> SEQUENCE: 64
gggaggacgg cgcuaacgcc aagcauaagc cuccc                                    35

<210> SEQ ID NO 65
<211> LENGTH: 31
<212> TYPE: RNA
<213> ORGANISM: Artificial sequence
<220> FEATURE:
<223> OTHER INFORMATION: Synthetic Oligonucleotide Modification of RB448
<220> FEATURE:
<221> NAME/KEY: misc_feature
<222> LOCATION: (12)..(12)
<223> OTHER INFORMATION: a spacer is incorporated between positions 12
      and 13

<400> SEQUENCE: 65
gggagcacgg cgcgccuggc auaagccucc c                                        31

<210> SEQ ID NO 66
<211> LENGTH: 31
<212> TYPE: RNA
<213> ORGANISM: Artificial sequence
<220> FEATURE:
<223> OTHER INFORMATION: Synthetic Oligonucleotide Modification of RB448
<220> FEATURE:
<221> NAME/KEY: misc_feature
<222> LOCATION: (12)..(12)
<223> OTHER INFORMATION: a spacer is incorporated between positions 12
      and 13

<400> SEQUENCE: 66
gggaggucgg cgcgccuggc auaagccucc c                                        31

<210> SEQ ID NO 67
<211> LENGTH: 31
<212> TYPE: RNA
<213> ORGANISM: Artificial sequence
<220> FEATURE:
<223> OTHER INFORMATION: Synthetic Oligonucleotide Modification of RB448
<220> FEATURE:
<221> NAME/KEY: misc_feature
<222> LOCATION: (12)..(12)
```

-continued

```
<223> OTHER INFORMATION: a spacer is incorporated between positions 12
      and 13

<400> SEQUENCE: 67
gggaggaggg cgcgccuggc auaagccucc c                                      31

<210> SEQ ID NO 68
<211> LENGTH: 31
<212> TYPE: RNA
<213> ORGANISM: Artificial sequence
<220> FEATURE:
<223> OTHER INFORMATION: Synthetic Oligonucleotide Modification of RB448
<220> FEATURE:
<221> NAME/KEY: misc_feature
<222> LOCATION: (12)..(12)
<223> OTHER INFORMATION: a spacer is incorporated between positions 12
      and 13

<400> SEQUENCE: 68
gggaggacgg cgcgccuugc auaagccucc c                                      31

<210> SEQ ID NO 69
<211> LENGTH: 29
<212> TYPE: RNA
<213> ORGANISM: Artificial sequence
<220> FEATURE:
<223> OTHER INFORMATION: Synthetic Oligonucleotide Modification of RB448
<220> FEATURE:
<221> NAME/KEY: misc_feature
<222> LOCATION: (11)..(11)
<223> OTHER INFORMATION: a spacer is incorporated between positions 11
      and 12

<400> SEQUENCE: 69
ggaggacggc gcgccuggca uaagccucc                                         29

<210> SEQ ID NO 70
<211> LENGTH: 31
<212> TYPE: RNA
<213> ORGANISM: Artificial sequence
<220> FEATURE:
<223> OTHER INFORMATION: Synthetic Oligonucleotide Modification of RB448
<220> FEATURE:
<221> NAME/KEY: misc_feature
<222> LOCATION: (22)..(22)
<223> OTHER INFORMATION: n is deoxythymidine
<220> FEATURE:
<221> NAME/KEY: misc_feature
<222> LOCATION: (12)..(12)
<223> OTHER INFORMATION: a spacer is incorporated between positions 12
      and 13

<400> SEQUENCE: 70
gggaggacgg cgcgccuggc anaagccucc c                                      31

<210> SEQ ID NO 71
<211> LENGTH: 31
<212> TYPE: RNA
<213> ORGANISM: Artificial sequence
<220> FEATURE:
<223> OTHER INFORMATION: Synthetic Oligonucleotide Modification of RB448
<220> FEATURE:
<221> NAME/KEY: misc_feature
<222> LOCATION: (12)..(12)
<223> OTHER INFORMATION: a spacer is incorporated between positions 12
      and 13

<400> SEQUENCE: 71
gggaggacgg cgcgccuggc guaagccucc c                                      31
```

```
<210> SEQ ID NO 72
<211> LENGTH: 31
<212> TYPE: RNA
<213> ORGANISM: Artificial sequence
<220> FEATURE:
<223> OTHER INFORMATION: Synthetic Oligonucleotide Modification of RB448
<220> FEATURE:
<221> NAME/KEY: misc_feature
<222> LOCATION: (12)..(12)
<223> OTHER INFORMATION: a spacer is incorporated between positions 12
      and 13

<400> SEQUENCE: 72
gggaggacgg cgcgccuugc guaagccucc c                                   31

<210> SEQ ID NO 73
<211> LENGTH: 31
<212> TYPE: RNA
<213> ORGANISM: Artificial sequence
<220> FEATURE:
<223> OTHER INFORMATION: Synthetic Oligonucleotide Modification of RB448
<220> FEATURE:
<221> NAME/KEY: misc_feature
<222> LOCATION: (12)..(12)
<223> OTHER INFORMATION: a spacer is incorporated between positions 12
      and 13

<400> SEQUENCE: 73
gggaggacga cgcgucuggc auaagccucc c                                   31

<210> SEQ ID NO 74
<211> LENGTH: 16
<212> TYPE: RNA
<213> ORGANISM: Artificial sequence
<220> FEATURE:
<223> OTHER INFORMATION: Synthetic Oligonucleotide Modulator sequence

<400> SEQUENCE: 74
aggaggcuua ugcaag                                                    16

<210> SEQ ID NO 75
<211> LENGTH: 17
<212> TYPE: RNA
<213> ORGANISM: Artificial sequence
<220> FEATURE:
<223> OTHER INFORMATION: Synthetic Oligonucleotide Modulator sequence

<400> SEQUENCE: 75
gaggcuuaug caagacg                                                   17

<210> SEQ ID NO 76
<211> LENGTH: 16
<212> TYPE: RNA
<213> ORGANISM: Artificial sequence
<220> FEATURE:
<223> OTHER INFORMATION: Synthetic Oligonucleotide Modulator sequence

<400> SEQUENCE: 76
uuaugcaaga cgggug                                                    16

<210> SEQ ID NO 77
<211> LENGTH: 18
<212> TYPE: RNA
<213> ORGANISM: Artificial sequence
<220> FEATURE:
<223> OTHER INFORMATION: Synthetic Oligonucleotide Modulator sequence

<400> SEQUENCE: 77
uuuuggcacc gcaucguc                                                  18
```

<210> SEQ ID NO 78
<211> LENGTH: 16
<212> TYPE: RNA
<213> ORGANISM: Artificial sequence
<220> FEATURE:
<223> OTHER INFORMATION: Synthetic Oligonucleotide Modulator sequence

<400> SEQUENCE: 78
aggaggcuua cgcaag                                                    16

<210> SEQ ID NO 79
<211> LENGTH: 17
<212> TYPE: RNA
<213> ORGANISM: Artificial sequence
<220> FEATURE:
<223> OTHER INFORMATION: Synthetic Oligonucleotide Modulator sequence

<400> SEQUENCE: 79
gaggcuuacg caagacg                                                   17

<210> SEQ ID NO 80
<211> LENGTH: 16
<212> TYPE: RNA
<213> ORGANISM: Artificial sequence
<220> FEATURE:
<223> OTHER INFORMATION: Synthetic Oligonucleotide Modulator sequence

<400> SEQUENCE: 80
uuacgcaaga cgcggu                                                    16

<210> SEQ ID NO 81
<211> LENGTH: 16
<212> TYPE: RNA
<213> ORGANISM: Artificial sequence
<220> FEATURE:
<223> OTHER INFORMATION: Synthetic Oligonucleotide Modulator sequence

<400> SEQUENCE: 81
ugugauccgc aucguc                                                    16

<210> SEQ ID NO 82
<211> LENGTH: 19
<212> TYPE: RNA
<213> ORGANISM: Artificial sequence
<220> FEATURE:
<223> OTHER INFORMATION: Synthetic Oligonucleotide Modulator sequence

<400> SEQUENCE: 82
gggaggcuua ugccaggcg                                                 19

<210> SEQ ID NO 83
<211> LENGTH: 17
<212> TYPE: RNA
<213> ORGANISM: Artificial sequence
<220> FEATURE:
<223> OTHER INFORMATION: Synthetic Oligonucleotide Modulator sequence

<400> SEQUENCE: 83
gaggcuuaug ccaggcg                                                   17

<210> SEQ ID NO 84
<211> LENGTH: 12
<212> TYPE: RNA
<213> ORGANISM: Artificial sequence
<220> FEATURE:
<223> OTHER INFORMATION: Synthetic Oligonucleotide Modulator sequence

```
<400> SEQUENCE: 84
uuaugccagg cg                                                    12

<210> SEQ ID NO 85
<211> LENGTH: 12
<212> TYPE: RNA
<213> ORGANISM: Artificial sequence
<220> FEATURE:
<223> OTHER INFORMATION: Synthetic Oligonucleotide Modulator sequence

<400> SEQUENCE: 85
cgccguccuc cc                                                    12

<210> SEQ ID NO 86
<211> LENGTH: 14
<212> TYPE: RNA
<213> ORGANISM: Artificial sequence
<220> FEATURE:
<223> OTHER INFORMATION: Synthetic Oligonucleotide Modulator sequence

<400> SEQUENCE: 86
gcuuaugcca ggcg                                                  14

<210> SEQ ID NO 87
<211> LENGTH: 15
<212> TYPE: RNA
<213> ORGANISM: Artificial sequence
<220> FEATURE:
<223> OTHER INFORMATION: Synthetic Oligonucleotide Modulator sequence

<400> SEQUENCE: 87
ggcuuaugcc aggcg                                                 15

<210> SEQ ID NO 88
<211> LENGTH: 16
<212> TYPE: RNA
<213> ORGANISM: Artificial sequence
<220> FEATURE:
<223> OTHER INFORMATION: Synthetic Oligonucleotide Modulator sequence

<400> SEQUENCE: 88
aggcuuaugc caggcg                                                16

<210> SEQ ID NO 89
<211> LENGTH: 30
<212> TYPE: DNA
<213> ORGANISM: Artificial sequence
<220> FEATURE:
<223> OTHER INFORMATION: Synthetic Oligonucleotide RB569
<220> FEATURE:
<221> NAME/KEY: misc_feature
<222> LOCATION: (11)..(11)
<223> OTHER INFORMATION: a spacer is incorporated between positions 11
      and 12
<220> FEATURE:
<221> NAME/KEY: modified_base
<222> LOCATION: 1,2,4,5,11,13,17,18,24
<223> OTHER INFORMATION: G is a 2'-O-methyl G
<220> FEATURE:
<221> NAME/KEY: modified_base
<222> LOCATION: 10,12,25,26,28,29
<223> OTHER INFORMATION: C is a 2'-O-methyl C
<220> FEATURE:
<221> NAME/KEY: modified_base
<222> LOCATION: 3,20,22,23
<223> OTHER INFORMATION: A is a 2'-O-methyl A
<220> FEATURE:
<221> NAME/KEY: modified_base
<222> LOCATION: 27
```

```
<223> OTHER INFORMATION: U is a 2'-O-methyl U
<220> FEATURE:
<221> NAME/KEY: modified_base
<222> LOCATION: 7,14,15,19
<223> OTHER INFORMATION: C is a 2'-Fluoro C
<220> FEATURE:
<221> NAME/KEY: modified_base
<222> LOCATION: 16,21
<223> OTHER INFORMATION: U is a 2'-Fluoro U
<220> FEATURE:
<221> NAME/KEY: misc_feature
<222> LOCATION: 8
<223> OTHER INFORMATION: A phosphorothioate linkage is present between
      residues 8 and 9
<220> FEATURE:
<221> NAME/KEY: misc_feature
<222> LOCATION: (30)..(30)
<223> OTHER INFORMATION: n is an inverted deoxythymidine

<400> SEQUENCE: 89
ggaggacggc gcgccuggca uaagccuccn                                              30

<210> SEQ ID NO 90
<211> LENGTH: 30
<212> TYPE: DNA
<213> ORGANISM: Artificial sequence
<220> FEATURE:
<223> OTHER INFORMATION: Synthetic Oligonucleotide RB570
<220> FEATURE:
<221> NAME/KEY: misc_feature
<222> LOCATION: (11)..(11)
<223> OTHER INFORMATION: a spacer is incorporated between positions 11
      and 12
<220> FEATURE:
<221> NAME/KEY: modified_base
<222> LOCATION: 1,2,4,5,11,13,17,18,24
<223> OTHER INFORMATION: G is a 2'-O-methyl G
<220> FEATURE:
<221> NAME/KEY: modified_base
<222> LOCATION: 10,12,25,26,28,29
<223> OTHER INFORMATION: C is a 2'-O-methyl C
<220> FEATURE:
<221> NAME/KEY: modified_base
<222> LOCATION: 3,20,22,23
<223> OTHER INFORMATION: A is a 2'-O-methyl A
<220> FEATURE:
<221> NAME/KEY: modified_base
<222> LOCATION: 27
<223> OTHER INFORMATION: U is a 2'-O-methyl U
<220> FEATURE:
<221> NAME/KEY: modified_base
<222> LOCATION: 7,14,15,19
<223> OTHER INFORMATION: C is a 2'-Fluoro C
<220> FEATURE:
<221> NAME/KEY: modified_base
<222> LOCATION: 16,21
<223> OTHER INFORMATION: U is a 2'-Fluoro U
<220> FEATURE:
<221> NAME/KEY: misc_feature
<222> LOCATION: (30)..(30)
<223> OTHER INFORMATION: n is an inverted deoxythymidine

<400> SEQUENCE: 90
ggaggacggc gcgccuggca uaagccuccn                                              30

<210> SEQ ID NO 91
<211> LENGTH: 30
<212> TYPE: DNA
<213> ORGANISM: Artificial sequence
<220> FEATURE:
<223> OTHER INFORMATION: Synthetic Oligonucleotide RB571
<220> FEATURE:
<221> NAME/KEY: misc_feature
<222> LOCATION: (11)..(11)
<223> OTHER INFORMATION: a spacer is incorporated between positions 11
      and 12
```

```
<220> FEATURE:
<221> NAME/KEY: modified_base
<222> LOCATION: 1,2,4,5,11,13,17,18,24
<223> OTHER INFORMATION: G is a 2'-O-methyl G
<220> FEATURE:
<221> NAME/KEY: modified_base
<222> LOCATION: 10,12,25,26,28,29
<223> OTHER INFORMATION: C is a 2'-O-methyl C
<220> FEATURE:
<221> NAME/KEY: modified_base
<222> LOCATION: 3,20,22,23
<223> OTHER INFORMATION: A is a 2'-O-methyl A
<220> FEATURE:
<221> NAME/KEY: modified_base
<222> LOCATION: 27
<223> OTHER INFORMATION: U is a 2'-O-methyl U
<220> FEATURE:
<221> NAME/KEY: modified_base
<222> LOCATION: 7,14,15,19
<223> OTHER INFORMATION: C is a 2'-Fluoro C
<220> FEATURE:
<221> NAME/KEY: modified_base
<222> LOCATION: 16,21
<223> OTHER INFORMATION: U is a 2'-Fluoro U
<220> FEATURE:
<221> NAME/KEY: misc_feature
<222> LOCATION: 8
<223> OTHER INFORMATION: A phosphorothioate linkage is present between
     residues 8 and 9
<220> FEATURE:
<221> NAME/KEY: misc_feature
<222> LOCATION: 9
<223> OTHER INFORMATION: A phosphorothioate linkage is present between
     residues 8 and 9
<220> FEATURE:
<221> NAME/KEY: misc_feature
<222> LOCATION: (30)..(30)
<223> OTHER INFORMATION: n is an inverted deoxythymidine

<400> SEQUENCE: 91
ggaggacggc gcgccuggca uaagccuccn                                   30

<210> SEQ ID NO 92
<211> LENGTH: 14
<212> TYPE: RNA
<213> ORGANISM: Artificial sequence
<220> FEATURE:
<223> OTHER INFORMATION: Synthetic Oligonucleotide; modified modulator
     sequence
<220> FEATURE:
<221> NAME/KEY: modified_base
<222> LOCATION: (1)..(14)
<223> OTHER INFORMATION: G=2'=O-methyl G,A=2'=O-methyl A,U=2'=O-methyl
     U,C=2'-O-methyl C

<400> SEQUENCE: 92
gcuuaugcca ggcg                                                    14

<210> SEQ ID NO 93
<211> LENGTH: 15
<212> TYPE: RNA
<213> ORGANISM: Artificial sequence
<220> FEATURE:
<223> OTHER INFORMATION: Synthetic Oligonucleotide; modified modulator
     sequence
<220> FEATURE:
<221> NAME/KEY: modified_base
<222> LOCATION: (1)..(15)
<223> OTHER INFORMATION: G=2'=O-methyl G,A=2'=O-methyl A,U=2'=O-methyl
     U,C=2'-O-methyl C

<400> SEQUENCE: 93
ggcuuaugcc aggcg                                                   15
```

```
<210> SEQ ID NO 94
<211> LENGTH: 16
<212> TYPE: RNA
<213> ORGANISM: Artificial sequence
<220> FEATURE:
<223> OTHER INFORMATION: Synthetic Oligonucleotide; modified modulator
      sequence
<220> FEATURE:
<221> NAME/KEY: modified_base
<222> LOCATION: (1)..(16)
<223> OTHER INFORMATION: G=2'=O-methyl G,A=2'=O-methyl A,U=2'=O-methyl
      U,C=2'=O-methyl C

<400> SEQUENCE: 94
aggcuuaugc caggcg                                                         16

<210> SEQ ID NO 95
<211> LENGTH: 12
<212> TYPE: RNA
<213> ORGANISM: Artificial sequence
<220> FEATURE:
<223> OTHER INFORMATION: Synthetic Oligonucleotide; modified modulator
      sequence
<220> FEATURE:
<221> NAME/KEY: modified_base
<222> LOCATION: (1)..(12)
<223> OTHER INFORMATION: G=2'=O-methyl G,A=2'=O-methyl A,U=2'=O-methyl
      U,C=2'=O-methyl C

<400> SEQUENCE: 95
uuaugccagg cg                                                             12

<210> SEQ ID NO 96
<211> LENGTH: 40
<212> TYPE: RNA
<213> ORGANISM: Artificial sequence
<220> FEATURE:
<223> OTHER INFORMATION: Synthetic Oligonucleotide; modified modulator
      sequence

<400> SEQUENCE: 96
ggaggacgau gcggauagac cgcgucuggc auaagccucc                               40
```

NUCLEIC ACID MODULATORS OF GLYCOPROTEIN VI

CROSS-REFERENCE TO RELATED APPLICATIONS

This application claims priority to U.S. Provisional Application No. 61/183,847, filed Jun. 3, 2009 and U.S. Provisional Application No. 61/300,951, filed Feb. 3, 2010, the contents of which are hereby incorporated by reference in their entirety.

REFERENCE TO SEQUENCE LISTING

A "Sequence Listing" has been submitted with this application in the form of a text file, created Mar. 29, 2012, named "108158009US01seq.txt" (33568 bytes), the contents of which are incorporated herein by reference in its entirety.

TECHNICAL FIELD

The present invention relates, in general, to an anti-platelet pharmacologic system comprising a nucleic acid ligand that binds to and regulates the activity of the platelet-specific protein glycoprotein VI (GPVI). These nucleic acid ligands are also actively reversible using a modulator that inhibits the activity of the nucleic acid ligand to neutralize its pharmacologic effect and thereby restore GPVI function. The invention further relates to compositions comprising the nucleic acid ligand and/or a modulator as well as methods of using these agents and compositions in treating platelet-mediated diseases and disorders.

BACKGROUND

Platelets are small, anuclear blood cells which are fairly quiescent under normal conditions but which respond immediately to vascular injury by adhesion, activation, aggregation, and thrombus formation. The primary function of platelets is to stop blood loss after tissue trauma and exposure of the subendothelial matrix. It is well known that damage to a blood vessel can expose extracellular matrix components to the blood, particularly von Willebrand factor (VWF), collagen, fibronectin, thrombospondin, and laminin. Interaction of platelets with these exposed molecules results in activation of the platelet cells.

While platelets have long been recognized as having a predominant role in hemostasis and thrombosis, it is becoming increasingly recognized that platelets may also play a significant role in a variety of other disorders such as inflammation, tumor growth and metastasis, and immunological host defense. Accordingly, platelet receptor proteins are attractive targets for regulation of platelet function as a means of treating or preventing platelet-mediated disorders.

Glycoprotein VI (GPVI) is a particularly attractive target as it is a transmembrane protein specifically expressed on platelets. Cell-specific molecules having extracellular exposure offer both accessibility to a therapeutic moiety and the potential for minimal—if any—adverse side effects, due to the limited expression profile.

Glycoprotein VI (GPVI) is a major platelet signaling receptor for collagen shown to have a role in generating intracellular signals that mediate platelet activation (Watson et al. Platelets, 2000, 11:252-258). GPVI is a 62-65 kDa glycoprotein in the Ig superfamily consisting of two Ig C2 loops that contain a collagen binding domain, representing potential drug target sites. The protein is very highly glycosylated and sialylated in vivo, and a single glycosylation site is found on the outer Ig-C2-like domain. As a member of the immunoglobulin superfamily, GPVI is related to natural killer receptors. Its signaling may be mediated indirectly through the γ-chain of FcR or directly through the GPVI cytoplasmic domain. The FcR γ-chain contains an immunoreceptor tyrosine-based activation motif and in conjunction with the non-tyrosine kinase SYK and the adapters LAT and LCP2 leads to the activation of phospholipase C2 and associated intracellular signaling pathways (Lankhof et al. Thromb Haemost, 1996, 75:950-958).

The importance of GPVI in the physiology and clinical events associated with clot formation has been recognized and is supported by epidemiologic associations of GPVI levels with onset of acute coronary syndrome (ACS) and stroke events (Bigalke et al. American Heart Journal, 2008, 156:193-200; Bigalke et al., European Journal of Neurology, 2009, 101:911-915), and the resistance to thrombosis demonstrated in GPVI deficient mice (Denis et al. Arteriosclerosis, Thrombosis and Vascular Biology, 2007, 27:728-739). Further, Gawaz et al have shown that radiolabeled GPVI could be used in scintillographic imaging of vascular lesions in mice as it binds specifically to the injured region, indicating that collagen is exposed at these sites (Thromb Haemost., 2005, 93:910-913). Penz et al. (FASEB J. 2005, 19:898-909) have shown that human atheromatous plaques from patients with carotid stenosis contained collagen type I and type III structures that were able to activate platelets. Further, blockage or absence of GPVI was able to prevent thrombus formation, whereas blockage of $\alpha_2\beta_1$ had little effect. Similarly blocking collagen with anti-collagen antibodies or degrading it with collagenase prevented thrombus formation.

More recently, GPVI has been linked to a broader role in disorders associated with platelet malfunctioning and abnormal collagen expression. This is due in part to the fact that platelets function both in adhesion following vascular injury as in the case of thrombosis, and in the release of a variety of inflammatory mediators and cytokines. Moreover, following reaction of platelets with a site of vascular injury, subsequent activation of the platelets results in release of cytokines and other regulatory molecules. Thus, although it may seem that the disorders associated with abnormal activation of platelets are diverse, these disorders are linked by their dependence on platelet function. Accordingly, inhibiting or preventing activation of platelets can provide valuable therapeutic effects.

Platelet-mediated disorders include vascular diseases as well as a variety of disorders associated with high-risk diabetes. Inflammatory disorders shown to be platelet-mediated include inflammatory arthritides and scleroderma. The role of inflammation and white blood cell activity has long been known in inflammatory joint disease. More recently, the presence of platelets in synovial fluid of inflamed joints has been identified (Boilard et al., Science, 2010, 327:580-583). Moreover, platelet microparticles in joint fluid from patients suffering from inflammatory arthritis have been shown to be proinflammatory, eliciting cytokine responses from synovial fibroblasts via IL-1. Both pharmacologic and genetic approaches showed that GPVI plays a key role in this proinflammatory nature of platelets in arthritis.

Other disorders shown to be associated with GPVI expression on the surface of platelets include experimental tumor metastasis (Jain et al., J. Thromb Haemostasis, 2009, 7:1713-1717), diabetes (Cabeza et al., 2004, 53:2117-2121) and infection by Hepatitis C virus (Zahn et al., Diabetes, 2004, 53:2117-2121).

Despite the expanding role GPVI has been shown to have in platelet function and related physiological maladies, efforts to discover and develop antagonists of this receptor have been limited. Active control, or modulation, of the intensity and duration of antiplatelet therapy can provide significant clinical benefit. Therefore, there remains a need in the art for modulatable agents designed to specifically target and regulate the function of the GPVI protein.

SUMMARY OF THE INVENTION

Described herein are compositions directed to nucleic acid ligands which specifically bind glycoprotein VI (GPVI), methods and treatments of use of nucleic acid ligands which specifically bind glycoprotein VI (GPVI), and modulators thereof.

In one aspect, a GPVI ligand is provided, wherein the ligand comprises an isolated nucleic acid sequence. In another embodiment, at least one nucleotide is a ribonucleotide. In another embodiment, at least one nucleotide is a deoxyribonucleic acid. In still another embodiment, the isolated nucleic acid sequence GPVI ligand comprises a mixture of ribonucleotides and deoxyribonucleotides.

In one embodiment, the nucleic acid GPVI ligand comprises a secondary structure comprising one, two, or three stems and one, two, three, or four, loops.

In one embodiment, the GPVI ligand comprises a secondary structure, wherein the secondary structure comprises, in a 5' to 3' direction, a first stem region, a first loop region, a second stem region, a second loop region, a third loop region, a third stem region and a fourth loop region. In another embodiment, the GPVI ligand consists essentially of, in a 5' to 3' direction, a first stem region, a first loop region, a second stem region, a second loop region, a third loop region, a third stem region and a fourth loop region.

In one embodiment, the nucleic acid GPVI ligand secondary structure is configured in the 5'-3' direction as the first stem, the first loop, the second stem connected to the second loop and to the third loop, a third stem connected to the third loop and to the fourth loop, and the fourth loop. In one embodiment, the second stem is connected to the first, the second, and the third loops.

In one embodiment, the fourth loop of the nucleic acid GPVI ligand comprises a first consensus sequence consisting of UAA. In another embodiment, the fourth loop comprises the sequence consisting of (G/A)UAA.

In one embodiment, the third stem comprises the sequence consisting of a G-C basepair followed by a C-G basepair.

In one embodiment, the nucleic acid GPVI ligand comprises GC(G/A)UAAGC. In another embodiment, the third stem and the fourth loop of the nucleic acid ligand comprise GC(G/A)UAAGC. In yet another embodiment, the third stem and the fourth loop of the nucleic acid ligand comprises a sequence selected from the group consisting of GCAUAAGC and GCGUAAGC.

In one embodiment, the third loop comprises the sequence YD, wherein Y is a pyrimidine and D is not cytosine. In another embodiment, the third loop comprises the sequence YU, YG or YA. In still another embodiment, the third loop comprises the sequence UU, UG, UA, CU, CG or CA. In another embodiment, the third loop consists of the sequence YD.

In one embodiment, the first loop comprises the sequence GAC.

In one embodiment, the isolated nucleic acid GPVI ligand sequence is about 20 nucleotides (nt) to about 50 nt in length, about 20 nt to about 45 nt in length, about 20 nt to about 40 nt in length, about 20 nt to about 35 nt in length, about 20 nt to about 30 nt in length, or about 30 nt to about 35 nt in length.

In one embodiment, the GPVI ligand comprises an isolated nucleic acid sequence selected from the group consisting of SEQ ID NO:7, SEQ ID NO:9, SEQ ID NO:11, SEQ ID NO:12, SEQ ID NO:14 and SEQ ID NO:15. In another embodiment, the GPVI ligand comprises an isolated nucleic acid sequence selected from the group consisting of SEQ ID NO:28 through SEQ ID NO:33, inclusive. In still another embodiment, the GPVI ligand comprises an isolated RNA nucleic acid sequence selected from the group consisting of EF-1-RNA, EF-2-RNA, EF-3-RNA, E2-6-RNA, EF-22-RNA and EF-31-RNA. In another embodiment, the GPVI ligand comprises an isolated RNA nucleic acid sequence selected from the group consisting of EF-1-modified, EF-2-modified, EF-3-modified, E2-6-modified, EF-22-modified and EF-31-modified. In another embodiment, the GPVI ligand comprises an isolated nucleic acid sequence which is at least 80% identical to the sequence selected from the group consisting of SEQ ID NO:28 through SEQ ID NO:33, inclusive.

In one embodiment, the GPVI ligand is selected from the group consisting of RB424, RB426, RB427, RB428, RB429, RB430, RB445, RB446, RB447, RB431, RB432, RB433, RB434, RB435, RB436, RB439, RB440, RB441, RB442, RB443 and RB444.

In one embodiment, the GPVI ligand is selected from the group consisting of RB448, RB452, RB453, RB455, RB460, RB462, RB466, RB478, RB480, RB488, EB490, RB491, RB492, RB493, RB495, RB496, RB497, RB498, RB499, RB500, RB502, RB503, RB504, RB505, RB506, RB507, RB508, RB517, RB518, RB519, RB520, RB521, RB522, RB523, RB524, RB525, RB526, RB527, RB528, RB531, RB532, RB533, RB534, RB535, RB536, RB537, RB538, RB540, RB541, RB542, RB546, RB547, RB548, RB549, RB550, RB551, RB552, RB553, RB554, RB555, RB556, RB560, RB561, RB566, RB567, RB569, RB570, RB571.

In one embodiment, the isolated nucleic acid sequence of the GPVI ligand comprises one or more ribonucleotides, deoxyribonucleotides, or a mixture both ribonucleotides and deoxyribonucleotides.

In one embodiment, one or more of the nucleotides of the isolated nucleic acid GPVI ligand sequence is modified. In another embodiment, the one or more nucleotides comprise a modification at the 2' hydroxyl position. In another embodiment, the modification is selected from the group consisting of 2'-O-methyl and 2'-fluoro. In yet another embodiment, the one or more nucleotides is 2'-O-methyl cytosine, 2'-O-methyl uridine, 2'-O-methyl adenosine or 2'-O-methyl guanosine. In still another embodiment, the one or more nucleotides is a 2' fluoro cytidine or a 2' fluoro uridine.

In one embodiment, the one or more nucleotides comprising a modification is selected from the group consisting of 5-fluorouracil, 5-fluorocytosine, 5-bromouracil, 5-bromocytosine, 5-chlorouracil, 5-chlorocytosine, 5-iodouracil, 5-iodocytosine, 5-methylcytosine, 5-methyluracil, hypoxanthine, xantine, 4-acetylcytosine, 5-(carboxyhydroxylmethyl) uracil, 5-carboxymethylamin-O-methyl thiouridine, 5-carboxymethylamin-O-methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 6-methylcytosine, N6-adenine, 7-methylguanine, 5-methylamin-O-methyluracil, 5-methoxyamin-O-methyl-2-thiouracil, beta-D-mannosylqueosine, 5'-methoxycarboxymethyluracil, 5-methoxyuracil, 5-methoxycytosine, 2-methylthio-N6-isopentenyladenine, uracil oxyacetic acid (v), butoxosine, pseudouracil, queosine, 2-thiocytosine, 5-methyl thiouracil, 2-thiouracil, 4-thiouracil, 5-methyluracil, uracil-5-oxyacetic acid methylester, uracil oxyacetic acid (v), 5-methyl thiouracil, 3-(3-amino-3-N carboxypropyl) uridine, (acp3U), and 2,6-diaminopurine.

In one embodiment, the GPVI ligand comprises at least one modified sugar moiety.

In one embodiment, the GPVI ligand comprises at least one modified phosphate backbone.

In one embodiment, the isolated nucleic acid GPVI ligand sequence comprises an inverted thymine at its 3' end.

In one embodiment, the nucleic acid GPVI ligand comprises a spacer. In another embodiment, the spacer is a glycol spacer. In another embodiment, the second loop of the nucleic acid GPVI ligand comprises the glycol spacer. In yet another embodiment, the second loop of the nucleic acid GPVI ligand consists of a glycol spacer. In still another embodiment, the glycol spacer is provided by incorporation of 9-O-Dimethoxytrityl-triethylene glycol, 1-[(2-cyanoethyl)-(N,N-diisopropyl)]-phosphoramidite. In yet another embodiment, the glycol spacer is attached to the 3' end of a first internal nucleotide of the isolated nucleotide GPVI ligand sequence and is attached to the 5' end of a second internal nucleotide adjacent to the first internal nucleotide of the isolated nucleotide GPVI ligand sequence.

In one embodiment, the nucleic acid GPVI ligand comprises an aliphatic amino linker. In another embodiment, the aliphatic amino linker is attached to the 5' end of the isolated nucleic acid GPVI ligand sequence. In yet another embodiment, the aliphatic amino linker is attached to the 3' end of the isolated nucleic acid GPVI ligand sequence. In still another embodiment, the aliphatic amino linker is provided by incorporation of 6-(trifluoroacetamino)hexanol (2-cyanoethyl-N, N-diisopropyl)phosphoramidite.

In one embodiment, the isolated nucleic acid GPVI ligand is linked to at least one hydrophilic moiety. In another embodiment, the at least one hydrophilic moiety is a polyalkylene glycol.

In one embodiment, the GPVI ligand comprises a polyalkylene moiety attached to the 5' end and/or the 3' end of the isolated nucleic acid sequence. In another embodiment, the polyalkylene moiety is attached via a linker. In yet another embodiment, the linker is an aliphatic amino linker.

In one embodiment, the GPVI ligand is linked to a 40 KD polyethylene glycol (PEG) moiety using a six carbon amino linker. In a another embodiment, the six carbon amino linker is attached to the PEG moiety through an amide attachment. In a yet another embodiment, the PEG moiety is two twenty KD PEG moieties which are attached to one or more amino acids, such as lysine, which is attached via an amide bond to the six carbon amino linker.

In one embodiment, the first nucleic acid GPVI ligand comprises a phosphorothioate linkage.

In one embodiment, the nucleic acid GPVI ligand specifically binds to GPVI (SEQ ID NO:1). In another embodiment, the nucleic acid GPVI ligand specifically binds to the extracellular domain of GPVI (SEQ ID NO:2).

In one embodiment, the GPVI ligand has a dissociation constant of about 20 nanomolar (nM) or less.

In one embodiment, the GPVI ligand has a dissociation constant which ranges from about 400 picomolar (pM) to about 10 nM.

In one embodiment, the GPVI ligand has a dissociation constant which ranges from about 100 pM to about 10 nM.

In one embodiment, the nucleic acid GPVI ligand inhibits binding of GPVI to collagen. In another embodiment, the nucleic acid GPVI ligand inhibits intracellular signaling via GPVI. In another embodiment, the inhibiting of intracellular signaling via GPVI using a GPVI ligand comprises reducing generation of inositol trisphosphate or inhibiting fluctuations in intracellular calcium levels.

In one embodiment, the nucleic acid GPVI ligand inhibits binding of GPVI to collagen-related peptide (CRP) and/or to convulxin.

In one embodiment, the nucleic acid GPVI ligand inhibits binding of GPVI to both collagen and to CRP.

In one embodiment, the nucleic acid GPVI ligand inhibits binding of GPVI to collagen but does not inhibit binding of GPVI to CRP. In another embodiment, the nucleic acid GPVI ligand inhibits binding of GPVI to both collagen and CRP but does not inhibit binding of GPVI to convulxin.

In one embodiment, binding of the nucleic acid GPVI ligand to GPVI stabilizes an active conformation of GPVI. In another embodiment, binding of the nucleic acid GPVI ligand to GPVI stabilizes an inactive conformation of GPVI. In yet another embodiment, binding of the nucleic acid GPVI ligand to GPVI inhibits interaction between GPVI and the FcR γ subunit.

In another embodiment, binding of the GPVI ligand to GPVI results in inhibition of, or reduction of, GPVI activity. In yet another embodiment, binding of the GPVI ligand to GPVI results in the inability of, or the reduction in ability of, GPVI to interact with FcR γ-chain. In still another embodiment, binding of the GPVI ligand to GPVI expressed on the surface of a platelet results in an inhibition of, or reduction of, platelet adhesion. In still another embodiment, binding of the GPVI ligand to GPVI expressed on the surface of a platelet results in an inhibition of, or reduction of, platelet activation. In still another embodiment, binding of the GPVI ligand to GPVI expressed on the surface of a platelet results in an inhibition of, or reduction of, platelet aggregation.

In one embodiment, the GPVI ligand binds to and decreases or inhibits a function of a variant of GPVI, wherein said GPVI variant is at least 80%, 85%, 90%, 91%, 93%, 94%, 95%, 96%, 97%, 98% or 99% identical to SEQ ID NO:1.

In one embodiment the GPVI ligand has a dissociation constant ("$K_d$") for GPVI of less than about 100 micromolar (μM), less than about 1 μM, less than about 500 nanomolar (nM), less than about 100 nM, less than about 50 nM, less than about 1 nM, less than about 500 picomolar (pM), less than about 300 μM, less than about 250 μM, or less than about 200 about pM.

In a second aspect, a modulator to the GPVI ligand is provided, wherein the modulator reverses, partially or completely, the activity of a GPVI ligand.

In one embodiment, the modulator comprises an isolated nucleic acid sequence. In another embodiment, the modulator comprises a DNA sequence, an RNA sequence, a polypeptide sequence, or any combination thereof.

In one embodiment, the modulator of a GPVI nucleic acid ligand is selected from the group consisting of a ribozyme, a DNAzyme, a peptide nucleic acid (PNA), a morpholino nucleic acid (MNA), and a locked nucleic acid (LNA).

In one embodiment, the modulator of a GPVI nucleic acid ligand is selected from the group consisting of a ribozyme, a DNAzyme, a peptide nucleic acid (PNA), a morpholino nucleic acid (MNA), and a locked nucleic acid (LNA), wherein the modulator specifically binds to or interacts with at least a portion of a GPVI nucleic acid ligand.

In one embodiment, the modulator is selected from the group consisting of a nucleic acid binding protein or peptide, a small molecule, an oligosaccharide, a nucleic acid binding lipid, a polymer, a nanoparticle, and a microsphere, wherein the modulator binds to or interacts with at least a portion of a GPVI nucleic acid ligand.

In one embodiment, the modulator is a nucleic acid modulator comprising deoxyribonucleotides, ribonucleotides, or a mixture of deoxyribonucleotides and ribonucleotides. In another embodiment the nucleic acid modulator comprises at least one modified deoxyribonucleotide and/or at least one modified ribonucleotide.

In one embodiment, the modulator is an oligonucleotide which is complementary to at least a portion of the GPVI nucleic acid ligand. In another embodiment, the modulator is an oligonucleotide which is complementary to at least a portion of a loop in the GPVI ligand. In another embodiment, the modulator is an oligonucleotide complementary to at least the first loop, the second stem, and the second loop of the nucleic acid GPVI ligand. In another embodiment, the modulator is an oligonucleotide complementary to the third loop, the third stem, the fourth loop, and the first stem of the GPVI ligand.

In one embodiment, the modulator comprises an isolated nucleic acid sequence, wherein the sequence is about 10 nt to about 30 nt, about 10 nt to about 25 nt, about 10 nt to about 20 nt, about 10 nt to about 15 nt, or about 15 nt to about 20 nt in length.

In one embodiment, one or more of the nucleotides of the nucleic acid modulator sequence is modified. In another embodiment, the one or more nucleotides comprise a modification at the 2' hydroxyl position. In another embodiment, the modification is selected from the group consisting of 2'-O-methyl and 2'-fluoro. In yet another embodiment, the one or more nucleotides is 2'-O-methyl cytosine, 2'-O-methyl uridine, 2'-O-methyl adenosine, 2'-O-methyl guanosine or a 2'-O-methyl thymidine. In still another embodiment, the one or more nucleotides is a 2' fluoro cytidine, a 2' fluoro uridine, a 2' fluoro adenosine or a 2'-fluoro guanosine.

In one embodiment, the modification of one or more nucleotides of the nucleic acid modulator comprises a modification selected from the group consisting of 5-fluorouracil, 5-fluorocytosine, 5-bromouracil, 5-bromocytosine, 5-chlorouracil, 5-chlorocytosine, 5-iodouracil, 5-iodocytosine, 5-methylcytosine, 5-methyluracil, hypoxanthine, xantine, 4-acetylcytosine, 5-(carboxyhydroxylmethyl) uracil, 5-carboxymethylamin-O-methyl thiouridine, 5-carboxymethylamin-O-methyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 6-methylcytosine, N6-adenine, 7-methylguanine, 5-methylamin-O-methyluracil, 5-methoxyamin-O-methyl-2-thiouracil, beta-D-mannosylqueosine, 5'-methoxycarboxymethyluracil, 5-methoxyuracil, 5-methoxycytosine, 2-methylthio-N6-isopentenyladenine, uracil oxyacetic acid (v), butoxosine, pseudouracil, queosine, 2-thiocytosine, 5-methyl thiouracil, 2-thiouracil, 4-thiouracil, 5-methyluracil, uracil-5-oxyacetic acid methylester, uracil oxyacetic acid (v), 5-methyl thiouracil, 3-(3-amino-3-N carboxypropyl)uridine (acp3U), and 2,6-diaminopurine.

In one embodiment, the modulator comprises as least one modified sugar moiety.

In one embodiment, the modulator comprises at least one modified phosphate backbone.

In one embodiment, the modulator comprises an oligonucleotide which hybridizes at physiological conditions to the fourth loop of the GPVI ligand. In another embodiment, the oligonucleotide modulator comprises the sequence 3'-AUU-5'.

In one embodiment, the modulator comprises an oligonucleotide which hybridizes under physiological conditions to the first loop of the GPVI ligand. In another embodiment, the oligonucleotide modulator comprises the sequence 3'CUG-5'.

In one embodiment, the modulator comprises the sequence selected from the group consisting of SEQ ID NOs:74-88, inclusive. In another embodiment, the modulator is selected from the group consisting of RB416, RB417, RB418, RB419, RB420, RB421, RB422, RB423, RB513, RB514, RB515, RB516, RB543, RB544, and RB545.

In one embodiment, the modulator disrupts the secondary structure of the nucleic acid GPVI ligand. In another embodiment, the modulator stabilizes the secondary structure of the GPVI ligand.

In one embodiment, the modulator disrupts the tertiary structure of the nucleic acid GPVI ligand. In another embodiment, the modulator stabilizes the secondary structure of the GPVI ligand.

In one embodiment, the binding of the modulator to the GPVI ligand exposes a suicide position within the GPVI ligand, thereby disrupting the secondary structure of the GPVI ligand and leading to enhanced destruction of the nucleic acid GPVI ligand by nucleases.

In one embodiment, binding of the modulator to a GPVI ligand-GPVI complex reduces or eliminates binding of the GPVI ligand to GPVI.

In another aspect, a method of modulating the activity of a GPVI ligand is provided.

In one embodiment, a method of modulating the activity of a nucleic acid ligand to GPVI by administering a modulator of the GPVI ligand to a host who has been administered the nucleic acid GPVI ligand is provided. In one embodiment, the modulator can be a oligonucleotide modulator, or derivative thereof, and in certain embodiments, is complimentary to a portion of the nucleic acid GPVI ligand.

In a further aspect, a method of regulating GPVI function using a GPVI ligand is provided.

In one embodiment, the method for regulating GPVI function comprises administering to a host a therapeutically effective amount of a GPVI ligand. In another embodiment, the method further comprises administering a GPVI ligand modulator to the host.

In another aspect, a method of treating or ameliorating a platelet-mediated disease or disorder is provided.

In one embodiment, the method comprises administering to a host in need thereof a therapeutically effective dose of a GPVI ligand that binds to GPVI. In another embodiment, the host is diagnosed with high-risk diabetes. In still another embodiment, the host is diagnosed with a cancer at high risk of metastasis.

In one embodiment, the platelet-mediated disease or disorder is selected from the group consisting of cerebrovascular disorders, acute coronary syndromes, diabetes-related disorders, autoimmune inflammatory disorders, and cancer.

In one embodiment, the cerebrovascular disorder is a thrombosis, thromboembolism, or transient ischemia attack (TIA). In another embodiment, the acute coronary syndrome is due to coronary thrombosis, unstable angina or myocardial infarction. In still another embodiment, the diabetes-related disorder is diabetic retinopathy, diabetic vasculopathy, atherosclerosis, ischemic stroke, peripheral vascular disease, acute renal injury or chronic renal failure. In another embodiment, the autoimmune inflammatory disorder is scleroderma, rheumatoid arthritis, or an inflammatory autoimmune disorder selected from the group consisting of psoriatic arthritis, reactive arthritis, inflammatory bowel disease and ankylosing spondylitis. In one embodiment, the cancer is selected from lung cancer, breast cancer, prostate cancer, pancreatic cancer, brain cancer, bone cancer and liver cancer.

In one embodiment, the GPVI ligand is administered by parenteral administration, intravenous injection, intradermal delivery, intra-articular delivery, intra-synovial delivery, intrathecal, intra-arterial delivery, intracardiac delivery, intramuscular delivery, subcutaneous delivery, intraorbital delivery, intracapsular delivery, intraspinal delivery, intrasternal delivery, topical delivery, transdermal patch delivery, rectal delivery, delivery via vaginal or urethral suppository, peritoneal delivery, percutaneous delivery, delivery via nasal spray, delivery via surgical implant, delivery via internal surgical paint, delivery via infusion pump or delivery via catheter.

In another aspect, a method for treating a host in need thereof by administering a GPVI ligand, wherein the GPVI ligand regulates platelet function is provided.

In one embodiment, a therapeutically effective dose of GPVI is administered.

In one embodiment, the therapeutically effective dose reduces or inhibits platelet adhesion and/or aggregation.

In one aspect, a pharmaceutical composition comprising a therapeutically effective amount of a nucleic acid GPVI ligand which binds GPVI is provided.

In one aspect, a pharmaceutical composition comprising a therapeutically effective amount of a modulator, wherein the modulator regulates the activity of a nucleic acid GPVI ligand which binds GPVI, is provided.

In one embodiment, the pharmaceutical composition comprises a GPVI ligand and pharmaceutically-acceptable excipients. In another embodiment, the pharmaceutical composition is a liquid suitable for intravenous injection. In yet another embodiment, the pharmaceutical composition is a liquid or dispersion suitable for subcutaneous injection.

In one aspect, a kit comprising a therapeutically effective amount of a GPVI nucleic acid ligand and/or a modulator which regulates the activity of the GPVI nucleic acid ligand is provided.

BRIEF DESCRIPTION OF THE DRAWINGS

FIG. 2 shows the selection conditions for the SELEX rounds performed to identify nucleic acid ligands to GPVI.

FIGS. 4A-B shows a primary random region derived sequence identified for individual clones in the "E/F" selection series after Round 10 of selection and for individual clones in the "E2" selection series after Round 10 of selection.

FIG. 5 shows a minimal predicted primary sequence required for GPVI binding and the predicted conserved secondary structure for sequences identified in the selection procedure. "L" denotes a loop, "S" denotes a stem region.

FIG. 7 is a graph of binding curves of truncated ligands to GPVI compared to parent GPVI ligands EF-2 and EF-3.

FIG. 8 shows the sequence and predicted secondary structure of several truncations of EF-3 and EF-31 GPVI ligand truncation variants.

FIG. 9 shows predicted secondary structure of the truncated sequence EF-3 T2 and EF-2 T2 GPVI ligands and the location of inactive point mutants.

FIG. 17 shows graphs of CRP-induced platelet aggregation expressed as percentage of control for varying concentrations of select GPVI nucleic acid ligands.

DETAILED DESCRIPTION

Figure 1:
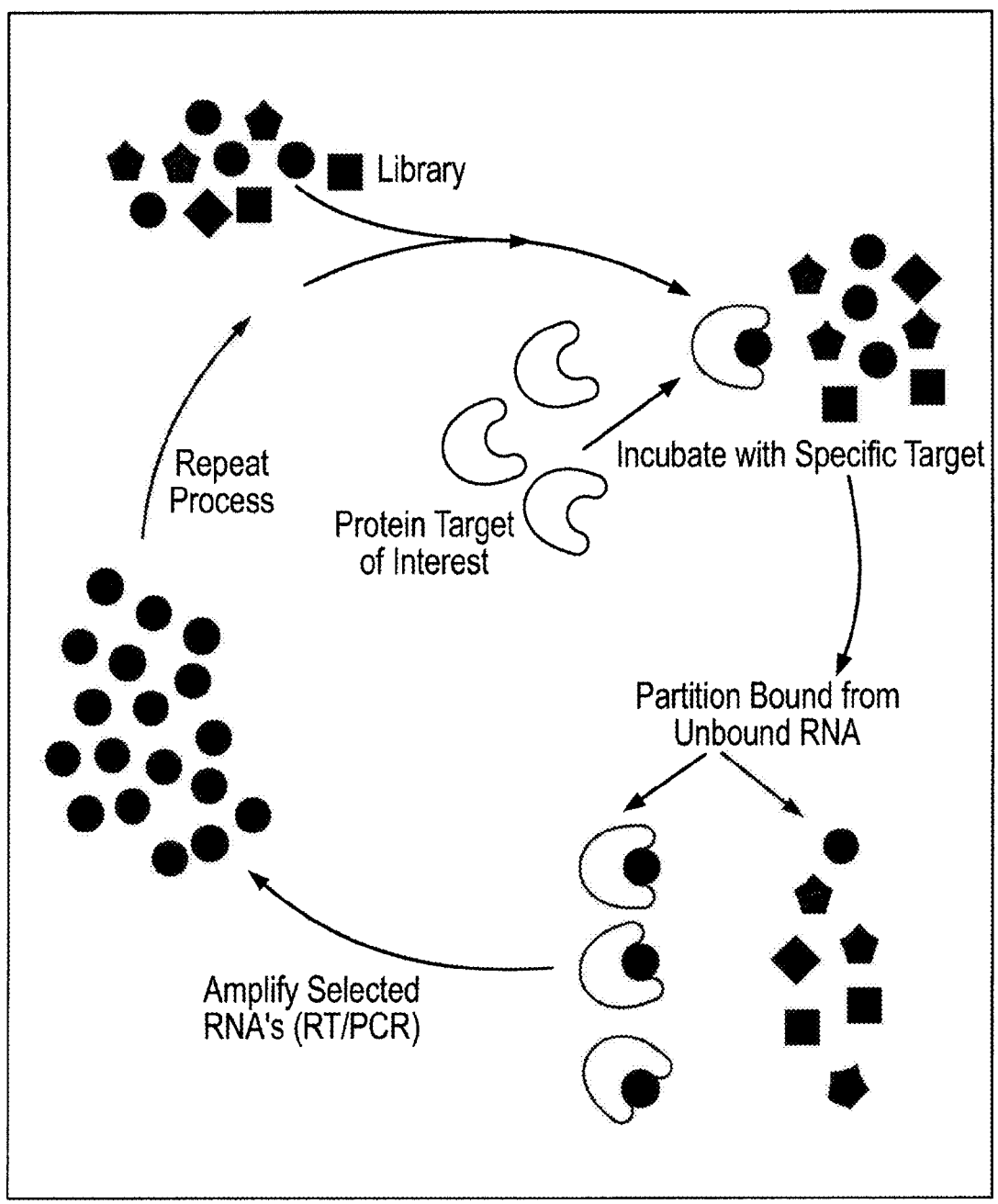
FIG. 1 is a diagram of the SELEX nucleic acid ligand selection process.

The present invention provides pharmaceutical compositions of nucleic acid ligands which bind to platelet membrane glycoprotein VI (GPVI), modulators of the ligands, and methods of use thereof for the treatment of platelet-mediated diseases and disorders. Further provided are pharmaceutical formulations comprising a GPVI nucleic acid ligand and/or GPVI ligand modulator.

A. DEFINITIONS

The term "about", as used herein when referring to a measurable value such as an amount of weight, time, dose, etc. is meant to encompass variations of ±20% or ±10%, ±5%, ±1%, or ±0.1% from the specified amount, as such variations are appropriate to perform the disclosed method.

A "nucleic acid ligand," which may also referred to herein as a "ligand" or "aptamer," is a nucleic acid that can form a tertiary structure, which allows it to interact with a target molecule. A "GPVI nucleic acid ligand" or "GPVI ligand" or "anti-GPVI ligand" of "nucleic acid GPVI ligand" refers to a ligand or aptamer that specifically binds to GPVI. The terms refer to oligonucleotides having specific binding regions that are capable of forming complexes with an intended target molecule in a physiological environment. The affinity of the binding of an ligand to a target molecule is defined in terms of the dissociation constant ($K_d$) of the interaction between the ligand and the target molecule. Typically, the $K_d$ of the ligand for its target is between about 1 nM to about 100 nM. The specificity of the binding is defined in terms of the comparative dissociation constant of the ligand for target as compared to the dissociation constant with respect to the ligand and other materials in the environment or unrelated molecules in general. Typically, the $K_d$ for the ligand with respect to the target will be 10-fold, 50-fold, 100-fold, or 200-fold less than the $K_d$ with respect to the unrelated material or accompanying material in the environment.

"Ligand modulator pair" or "ligand modulator pair" is meant to include a specified ligand to a target molecule, and a ligand modulator that changes the secondary and/or tertiary structure of the ligand so that the ligand's interaction with its target is modulated. The modulator can be an oligonucleotide complimentary to a portion of the ligand. The modulator can change the conformation of the ligand to reduce the target binding capacity of the ligand by 10% to 100%, 20% to 100%, 25%, 40%, 50%, 60%, 70%, 80%, 90% or 100%, or any percentage in the range between 10% and 100% under physiological conditions.

"Modulator," "antidote," "regulator" or "control agent" refer to any pharmaceutically acceptable agent that can bind a ligand or aptamer as described herein and modify the interaction between that ligand and its target molecule (e.g., by modifying the structure of the ligand) in a desired manner.

"Modulate" as used herein means a lessening, an increase, or some other measurable change in activity.

"Pharmaceutically acceptable," as used herein means approved by a regulatory agency of the Federal or a state government or listed in the U.S. Pharmacopeia or other generally recognized pharmacopeia for use in humans.

A pharmaceutically effective dose is that dose required to prevent, inhibit the occurrence, or treat (alleviate a symptom to some extent) of a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon the potency of the nucleic acid ligand and modulator.

A "stabilized nucleic acid molecule" refers to a nucleic acid molecule that is less readily degraded in vivo (e.g., via an exonuclease or endonuclease) in comparison to a non-stabilized nucleic acid molecule. Stabilization can be a function of length and/or secondary structure and/or inclusion of chemical substitutions within the sugar of phosphate portions of the oligonucleotide backbone. Stabilization can be obtained by controlling, for example, secondary structure which can stabilize a molecule. For example, if the 3' end of a nucleic acid molecule is complementarily to an upstream region, that portion can fold back and form a "stem loop" structure which stabilizes the molecule.

The terms "binding affinity" and "binding activity" are meant to refer to the tendency of a ligand molecule to bind or not to bind to a target. The energetics of said interactions are significant in "binding activity" and "binding affinity" because they define the necessary concentrations of interacting partners, the rates at which these partners are capable of associating, and the relative concentrations of bound and free molecules in a solution. The energetics may be characterized through, among other ways, the determination of a dissociation constant, $K_d$.

"Treatment" or "treating" as used herein means any treatment of disease in a mammal, including: (a) protecting against the disease, that is, causing the clinical symptoms not to develop; (b) inhibiting the disease, that is, arresting, ameliorating, reducing, or suppressing the development of clinical symptoms; and/or (c) relieving the disease, that is, causing the regression of clinical symptoms. It will be understood by those skilled in the art that in human medicine, it is not always possible to distinguish between "preventing" and "suppressing" since the ultimate inductive event or events may be unknown, latent, or the patient is not ascertained until well after the occurrence of the event or events. Therefore, as used herein the term "prophylaxis" is intended as an element of "treatment" to encompass both "preventing" and "suppressing" as defined herein. The term "protection," as used herein, is meant to include "prophylaxis."

The term "effective amount" means a dosage sufficient to provide treatment for the disorder or disease state being treated. This will vary depending on the patient, the disease and the treatment being effected.

A GPVI nucleic acid ligand "variant" as used herein encompasses variants that perform essentially the same function as a GPVI nucleic acid ligand and comprises substantially the same structure.

B. GLYCOPROTEIN VI

Glycoprotein VI (GPVI) is specifically expressed on the surface of platelet cells. Numerous studies have shown that collagen-mediated activation of GPVI plays a key role in platelet adhesion and aggregation. Accordingly, GPVI is a therapeutic target of increasing interest for the treatment of platelet and collagen-mediated diseases.

As the demarcation between physiological hemostasis and pathological thrombosis is very narrow, it is essential to be able to provide fine-tuned control of platelet activity with respect to collagen-mediated GPVI activation. Accordingly, also provided herein are modulator components capable of modulating or regulating the activity of the disclosed GPVI ligands.

GPVI is a glycoprotein of 339 amino acid residues in length (GenBank Accession No. Q9HCN6; disclosed herein as SEQ ID NO:1). Amino acid residues 1-20 represent a signal sequence that is cleaved to produce the mature protein having 319 amino acids. GPVI has two extracellular immunoglobulin domains, a mucin-like core, a short peptide linker sequence, a transmembrane domain and a short cytoplasmic tail that binds Fyn and Lyn Src family kinases. GPVI is also constitutively complexed with FcR γ-chain allowing the assembly and activation of Syk and initiating activation of a downstream signaling pathway that has many similarities with that employed by immune receptors. The gene encoding GPVI is found in the leukocyte receptor cluster (LRC) on human chromosome 19. Mice that lack either GPVI or the FcR γ-chain have significantly impaired platelet response to collagen and reduced thrombus formation. Additionally, the Fab fragment of a novel monoclonal antihuman GPVI antibody, OM4, inhibits thrombosis in vivo in a model of thrombosis in rats without prolongation of bleeding time seen with anti GP IIb/IIIa antibodies.

The GPVI extracellular domain (SEQ ID NO:2) has been shown to specifically bind collagen types I-IV (Jung et al., Platelets, 2008, 19:32-42). Moreover, collagen types I-IV are known to support platelet activation, aggregation and adhesion, while the non-fibrillar collagens, types VI, VII and VIII induce only weak adhesion with no platelet aggregation. Accordingly, studies were done to identify GPVI ligands that bind to the GPVI extracellular domain, in order to generate a pharmaceutical agent which can be useful in the treatment of platelet-mediated disorders or diseases.

C. DEVELOPMENT OF NUCLEIC ACID LIGANDS TO GPVI

Nucleic acid ligands which specifically bind the GPVI protein were identified using the SELEX method. The ligands which were initially obtained via SELEX were then fully characterized to understand the properties of the GPVI ligands. Such characterization included sequencing, sequence alignment to determine conserved sequences, secondary structure prediction, and truncations and mutation analysis to identify ligand regions most critical for the desired function of specifically binding and inhibiting GPVI. After identifying optimal ligand sequence and secondary structures, modifications were made to optimize the ligands for pharmaceutical use. Examples of these modifications include pegylation, use of a spacer within the nucleic acid ligand and selected modifications to the sugar and phosphate portion of the nucleic acid ligand. Binding assays were performed to monitor ligand function as a result of the various modifications used.

SELEX refers to the Systematic Evolution of Ligands by EXponential Enrichment. This method allows the in vitro evolution of nucleic acid molecules with highly specific binding to target molecules. The SELEX method is described in, for example, U.S. Pat. Nos. 7,087,735; 5,475,096; and 5,270,163 (see also WO 91/19813).

The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, such as mixtures comprising a segment of randomized sequence, the SELEX method includes steps of contacting the mixture with the target under conditions favorable for binding, partitioning unbound nucleic acids from those nucleic acids which have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific, high affinity ligands to the target molecule.

The basic SELEX method has been modified to achieve a number of specific objectives. For example, U.S. Pat. No. 5,707,796 describes the use of SELEX in conjunction with gel electrophoresis to select nucleic acid molecules with specific structural characteristics, such as bent DNA. U.S. Pat. No. 5,763,177 describes a SELEX-based method for selecting ligands containing photoreactive groups capable of binding and/or photocrosslinking to and/or photoinactivating a target molecule. U.S. Pat. No. 5,580,737 describes a method for identifying highly specific ligands able to discriminate between closely related molecules, termed Counter-SELEX. U.S. Pat. Nos. 5,567,588 and 5,861,254 describe SELEX-based methods that achieve highly efficient partitioning between oligonucleotides having high and low affinity for a target molecule. U.S. Pat. No. 5,496,938, describes methods for obtaining improved ligands after the SELEX process has been performed. U.S. Pat. No. 5,705,337, describes methods for covalently linking a ligand to its target.

The feasibility of identifying nucleic acid ligands to small peptides in solution was demonstrated in U.S. Pat. No. 5,648,214. The ability to use affinity elution with a ligand to produce ligands that are targeted to a specific site on the target molecule is exemplified in U.S. Pat. No. 5,780,228, which relates to the production of high affinity ligands binding to certain lectins. Methods of preparing nucleic acid ligands to certain tissues, which include groups of cell types, are described in U.S. Pat. No. 6,127,119. The production of certain modified high affinity ligands to calf intestinal phosphatase is described in U.S. Pat. No. 6,673,553. U.S. Pat. No. 6,716,580 describes an automated process of identifying nucleic acid ligands that includes the use of a robotic manipulators.

In its most basic form, the SELEX process may be defined by the following series of steps:

1) A candidate mixture of nucleic acids of differing sequence is prepared. The candidate mixture generally includes regions of fixed sequences (i.e., each of the members of the candidate mixture contains the same sequences in the same location) and regions of randomized sequences. The fixed sequence regions are selected either: (a) to assist in the amplification steps described below, (b) to mimic a sequence known to bind to the target, or (c) to enhance the concentration of a given structural arrangement of the nucleic acids in the candidate mixture. The randomized sequences can be totally randomized (i.e., the probability of finding a base at any position being one in four) or only partially randomized (e.g., the probability of finding a base at any location can be selected at any level between 0 and 100%).

2) The candidate mixture is contacted with the selected target under conditions favorable for binding between the target and members of the candidate mixture. Under these circumstances, the interaction between the target and the nucleic acids of the candidate mixture can be considered as forming nucleic acid-target complexes between the target and those nucleic acids having the strongest affinity for the target.

3) The nucleic acids with the highest affinity for the target are partitioned from those nucleic acids with lesser affinity to the target. Because only an extremely small number of sequences (and possibly only one molecule of nucleic acid) corresponding to the highest affinity nucleic acids exist in the candidate mixture, it is generally desirable to set the partitioning criteria so that a significant amount of the nucleic acids in the candidate mixture (approximately 5 to 50%) are retained during partitioning.

4) Those nucleic acids selected during partitioning as having the relatively higher affinity to the target are then amplified to create a new candidate mixture that is enriched in nucleic acids having a relatively higher affinity for the target.

5) By repeating the partitioning and amplifying steps above, the newly formed candidate mixture contains fewer and fewer weakly binding sequences, and the average degree of affinity of the nucleic acids to the target will generally increase. Taken to its extreme, the SELEX process will yield a candidate mixture containing one or a small number of unique nucleic acids representing those nucleic acids sequences from the original candidate mixture which fold into a specific secondary and tertiary structure enabling the highest affinity interaction with the target molecule.

SELEX can be used generate bivalent binding that have two or more binding domains with affinity for two or more epitopes of a protein, including a receptor. Specifically, in one embodiment, the process can be used to select for nucleic acid ligands that have affinity for two or more regions of the GPVI receptor. For example, in certain embodiments, the ligand can bind to at least two portions of the C2 regions. In certain embodiments, the ligand affects dimerization of the GPVI receptor, either by disrupting or stabilizing the dimeric conformation. In these embodiments, modulators can be designed to reduce binding to only one, more than one, or all epitopes that the nucleic acid ligand binds to. The modulator can, for example, interfere with binding to only a single epitope, such as a C2-1 or C2-2 region of the receptor.

Nucleic acid ligands specific to GPVI may be generated by performing SELEX against short peptides which represent the extracellular domain of the molecule, using SELEX methods as described for example in U.S. Pat. No. 7,087,735. Alternatively nucleic acid ligands specific to GPVI can be isolated by performing SELEX on intact platelets, platelet membrane fractions enriched for the protein, on purified GPVI, or on cell-lines specifically over-expressing the GPVI receptor using SELEX methods as described, for example, in U.S. Pat. No. 6,730,482.

Additionally, the SELEX process can be directed to isolate specific GPVI nucleic acid ligands using competitive affinity elution schemes, such as those described in U.S. Pat. No. 5,780,228. For example, to isolate nucleic acid ligands specific to GPVI, elution of ligands bound to the protein could be accomplished by addition of sufficient amounts of an activator or binder of GPVI such as collagen, convulxin or CRP or related compounds.

The GPVI receptor can be a recombinantly expressed and purified protein used for a SELEX procedure. In certain embodiments, the GPVI nucleic acid ligand binds to the GPVI receptor under physiological conditions. Physiological conditions are typically related to the level of salts and pH of a solution. In vitro, physiological conditions are typically replicated in a buffer including 150 mM NaCl, 2 mM $CaCl_2$ 20 mM HEPES, at a pH of about 7.4. In certain embodiments, native, typically unactivated, platelets are used as described above to screen a population of nucleic acid ligands and provide an enriched population, which contains ligands directed to proteins found on platelets. The enriched population is then used against either a stable cell line overexpressing the desired GPVI receptor, or a cell line that has been transiently transfected with the protein. The secondary screening can be accomplished either by using a modified SELEX procedure on isolated receptors from these cells or on the whole cells either through ligand competition studies or by identifying the effects on intracellular signaling pathways.

In certain embodiments, nucleic acid ligands to specific GPVI targets can be identified using an immobilized protein. In some of these embodiments, a purified protein can be linked to a solid matrix by a chemical linker. In other embodiments, membranes from cells over-expressing a particular protein can be extracted using a detergent, such as an anionic detergent (e.g. cholate), to isolate a certain fraction of the proteins and the mixture coupled to an immobilized artificial membrane. Generally, it is thought that the reorganization can be accomplished by removal of the detergent, during which lipids and proteins reorganize and form a layer with the hydrocarbon chains of the immobilized artificial membrane, which is generally on a support matrix such as a bead.

Nucleic acid ligands isolated by these SELEX procedures specific to GPVI, which also possess a desired functional activity can be identified by screening nucleic acid ligands for their ability to inhibit specific agonist-induced platelet function and/or intracellular signaling events elicited by GPVI. As the desired nucleic acid ligands are not merely binding partners, but are inhibitors of the receptor signaling, it is possible to identify ligands having a desired function by assessing the effect of the ligand on platelet activity. This can include characterizing the effects of the ligand on various signally pathways known to be regulated by GPVI. For example, GPVI signaling can lead to clustering of the GPVI protein, and to the activation of kinases to start a local signal chain of events that activates phospholipase Cγ2, releasing the second messengers 1,4,5-inositol trisphosphates and diacylglycerol that are responsible for raising $Ca^{2+}$ levels and activating protein kinase C. Any of these second messenger systems or signals can be measured using methods well known to those having ordinary skill in the art.

In addition, collagen binding of GPVI in the presence or absence of a GPVI nucleic acid ligand, can be measured in these systems.

Ligands can also be screened for inhibition of platelet aggregation in platelet function assays such as Light Transmittance Aggregometry performed in platelet rich plasma and wash platelet preparations or Impedance Aggregometry performed in whole blood. Additionally, ligands can also be screened for inhibition of platelet interaction with collagen coated surfaces in static conditions or in flowing whole blood. The specificity of a given nucleic acid ligand for GPVI can be further distinguished by the ability of the ligand to block intracellular signaling events triggered by known agonists of the given receptor. For example, a nucleic acid ligand inhibitor of GPVI may be expected to block signaling triggered by, for example, the snake C-type lectin convulxin, collagen or collagen-related peptide (CRP). The specificity of a given nucleic acid ligand for GPVI can also be further distinguished by the absence of an effect on platelet aggregation when aggregation is triggered by an agonist that activates a receptor other than GPVI.

Application of any of the above-described methods, alone or in combination, will give rise to a plurality of nucleic acid ligands specific to GPVI. Upon identification of a nucleic acid ligand with the desired inhibitory properties, modulators of this ligand can be identified as described below.

D. NUCLEIC ACID LIGANDS TO GPVI

The GPVI ligands disclosed herein are preferably nucleic acid ligands, such as ligands. GPVI ligands which specifically bind the GPVI extracellular domain (ECD) (amino acid residues Gln21-Lys267; SEQ ID NO:2) were selected using the SELEX method, described in more detail below and in Example 1, then modified to increase stability, affinity for GPVI and/or the ability to regulate GPVI activity.

A GPVI nucleic acid ligand of the present invention is comprised of an isolated nucleic acid sequence, which can be DNA or RNA, and which can be synthesized using modified ribo- or deoxyribonucleic acids. As described herein, if a base structure of RNA is utilized, the structure will include uridine (U) in lieu of thymidine (T) in the base sequence. In certain embodiments described herein, the sequence of nucleic acids is written as an RNA sequence. Similarly, in certain embodiments described herein, wherein the nucleic acid ligand is initially identified as a DNA molecule, the sequence of nucleic acids is written as a DNA sequence. It is understood that a sequence of nucleotides presented in text form as a DNA sequence inherently provides description of the corresponding RNA sequence, wherein thymines (T's) within the DNA sequence are replaced with uridines (U's) to get the corresponding RNA sequence of nucleotides. Similarly, it is understood that a sequence presented in text form as a RNA sequence inherently provides description of the corresponding DNA sequence, wherein uridines (U's) within the RNA sequence are replaced with thymines (T's) to get the corresponding DNA sequence.

Several GPVI nucleic acid ligands obtain via the SELEX method were sequenced and their sequences aligned. Alignment of the sequences shown in FIG. 4 resulted in the identification of 6 unique sequences enriched through the selection process. An alignment of the 6 sequences, referred to as "A" through "F", shows the presence of a UAA sequence. Moreover, this fully conserved sequence is contained within the sequence: (G/A)UAA. The (G/A)UAA sequence, which is flanked on each side by a GC, giving rise to a conserved GC(G/A)UAAGC sequence.

Secondary structure prediction analysis was then performed for the unique GPVI ligands. Secondary structure contributes to the functional nature of the ligand. As is well understood by the skilled artisan, the secondary structure can be described in terms of stem and loop structures as they occur in the molecule in a 5' to 3' direction. Based on secondary structure prediction as described in Example 2 below, ligands to the GPVI ECD possess a secondary structure that includes three stems and four loops. The 5' to 3' configuration includes a first stem (Stem 1 or S1), a first loop (Loop 1 or L1), a second stem (Stem 2 or S2) connecting to the second and a third loop (Loop 3 or L3), the third loop, a third stem (Stem 3 or S3) and a fourth loop (Loop 4 or L4) (see FIGS. 8A-8C). In some embodiments, the second stem links the first, second and third loops and the third stem links the third and fourth loop. In one embodiment, the third stem is adjacent to the first stem in a 5'-3' direction. The sequence GC(G/A)UAAGC forms Stem 3 (a GC base pair) and Loop 4 ((G/A)UAA). The sequence GAC forms Loop 1.

Mutational analysis of GPVI ligands identified by SELEX shows that a Loop 3 sequence of UA, UU or UG supports high affinity binding of the ligands to GPVI. Accordingly, in some embodiments, the Loop 3 of the GPVI nucleic acid ligand comprises the sequence 5'-YD-3', wherein Y represents a pyrimidine and D represents U, G or A.

In some embodiments, Loop 2 of the GPVI nucleic acid ligand may be substituted with a spacer using methods known to skilled artisans. The spacer can be a non-nucleotide spacer which provides a structure analogous to Loop 2 such that the GPVI ligand maintains its structure and function when Loop 2 is substituted with the spacer. Substitution of Loop 2 with a hexaethylene glycol spacer provided by incorporation of (9-O-Dimethoxytrityl-triethylene glycol, 1-[(2-cyanoethyl)-(N,N-diisopropyl)]-phosphoramidite (see FIGS. 13A-13B) into the GPVI nucleic acid ligand resulted in no loss of affinity for GPVI. Accordingly, one having ordinary skill in the art would understand that Loop 2 can be replaced with a variety of non-nucleotide spacers that are commercially available. Examples of such spacers include, but are not limited to those provided by incorporation of, 5'-O-Dimethoxytrityl-1'2'Dideoxyribose-3'-[(2-cyanoethyl)-(N,N-diisopropyl)]-phosphoramidite; 18-O-Dimethoxytritylhexaethyleneglycol, 1-[(2-cyanoethyl)-(N,N-diisopropyl)]-phosphoramidite; and 12-(4,4'-Dimethoxytrityloxy)dodecyl-1-[(2-cyanoethyl)-(N,N-diisopropyl)]-phosphoramidite into the GPVI nucleic acid ligand.

Efficacy of a GPVI ligand in regulating GPVI function or treating platelet-mediated disease depends largely upon the ability of the ligand to bind with sufficient affinity to the GPVI protein. Accordingly, after obtaining GPVI ligands through the SELEX process, each ligand is sequenced, and then may be characterized in terms of binding to the target molecule. The binding affinity of the ligands herein with respect to the target (GPVI) can be defined in terms of $K_d$. The value of this dissociation constant can be determined directly by well-known methods, such as by radioligand binding methods described in Example 1. It has been observed, however, that for some small oligonucleotides, direct determination of $K_d$ is sometimes difficult, and can lead to misleadingly high results. Under these circumstances, a competitive binding assay for the target molecule or other candidate substance can be conducted with respect to substances known to bind the target or candidate. The value of the concentration at which 50% inhibition occurs ($K_i$) is, under ideal conditions, equivalent to $K_d$. However, in no event will a $K_i$ be less than $K_d$. Thus, determination of $K_i$, in the alternative, sets a maximal value for the value of $K_d$. Under those circumstances where technical difficulties preclude accurate measurement of $K_d$, measurement of $K_i$ can conveniently be substituted to provide an upper limit for $K_d$. A $K_i$ value can also be used to confirm that an ligand of the present binds a target. In characterizing GPVI ligand binding properties, specificity may be analyzed using competition binding or functional assays with known GPVI binding molecules such as collagen, CRP (collagen related peptide), or convulxin (Cvx).

In some embodiments, the $K_d$ of binding of the ligand to GPVI can range from between about 1 nM to about 100 nM, from about 10 nM to about 50 nM or from about 20 nM to about 0.1 nM. In other embodiments, the $K_d$ of binding of a ligand to GPVI is at least 2-fold, 3-fold, 4-fold, 5-fold or 10-fold less than the $K_d$ of binding of the ligand to an unrelated protein or other accompanying material in the environment. The unrelated protein could also be a protein having motifs related to those present in GPVI, such as another Ig superfamily member or another protein including a collagen-binding domain or another platelet activation or adhesion receptor.

As will be discussed in greater detail below, the binding activity of the ligand obtained and identified by the SELEX method can be further modified or enhanced using a variety of engineering methods.

In some embodiments, the ligand interacts with the extracellular domain of GPVI. The ligand can interfere with collagen binding of the GPVI receptor. In certain embodiments, the ligand can inhibit intracellular signaling via the GPVI receptor, including reducing the generation of inositol trisphosphate or fluctuations in intracellular calcium levels. The ligand can also stabilize or disrupt a conformation of the receptor, such as a dimeric conformation, so that the receptor has a reduced capacity to interact with collagen or FcRγ. The ligand can affect platelet activation by collagen or other GPVI agonists. The ligand can also affect platelet adhesion to collagen or collagen-related peptides. The ligand can affect platelet aggregation induced by collagen or other GPVI agonists.

The nucleic acid ligands described herein can function as actively reversible agents. These are agents or pharmaceutically active molecules that, after administration to a patient, can be directly controlled by the administration of a second agent. As described in more detail below, the second agent, referred to herein as a modulator, can shut off or fine-tune the pharmacologic activity of the ligand. As a result, the pharmacologic activity of the ligand can be reversed by means other than, for example, drug clearance.

E. MODULATORS

In some embodiments, the nucleic acid ligands to GPVI are reversible. In one aspect, the invention provides a method of modulating the activity of a nucleic acid ligand to GPVI by administering a modulator of the GPVI ligand to a host who has been administered the nucleic acid ligand.

Modulators of the present invention include any pharmaceutically acceptable agent that can bind to a nucleic acid ligand and modify the interaction between that ligand and its target molecule (e.g., by modifying the structure of the nucleic acid ligand) in a desired manner, or which degrades, metabolizes, cleaves, or otherwise chemically alters the nucleic acid ligand to modify its biological effect. Examples of modulators of the present invention include: oligonucleotides, or analogues thereof, that are complementary to at least a portion of the nucleic acid ligand sequence (including ribozymes or DNAzymes). Other examples include peptide nucleic acids (PNA), morpholino nucleic acids (MNA), or locked nucleic acids (LNA); nucleic acid binding proteins or peptides; oligosaccharides; small molecules; or nucleic acid binding polymers, lipids, nanoparticle, or microsphere-based modulators.

Modulators can be designed so as to bind a particular nucleic acid ligand with a high degree of specificity and a desired degree of affinity. Modulators can also be designed so that, upon binding, the structure of the ligand is modified to either a more or less active form. For example, the modulator can be designed such that upon binding to the targeted nucleic acid ligand, the secondary and/or tertiary structure of that ligand is altered whereby the ligand can no longer bind to its target molecule or binds to its target molecule with less affinity. Alternatively, the modulator can be designed so that, upon binding, the three dimensional structure of the ligand is altered so that the affinity of the ligand for its target molecule is enhanced. That is, the modulator can be designed so that, upon binding, a structural motif is modified such that affinity of the ligand is increased. In another embodiment, a ligand/modulator pair is designed such that binding of the modulator to a nucleic acid ligand molecule which cannot bind to the target of interest can result in production of a structural motif within the ligand which thereby allows the ligand to bind to its target molecule.

Modulators can also be designed to nonspecifically bind to a particular nucleic acid ligand or set of nucleic acid ligands with sufficient affinity to form a complex. Such modulators can generally associate with nucleic acids via charge-charge interactions. Such modulators can also simultaneously bind more than one nucleic acid ligand. The modulator can be designed so that, upon binding to one or more nucleic acid ligands, the structure of the nucleic acid ligand is not significantly changed from its active form, but rather, the modulator masks or sterically prevents association of the nucleic acid ligand with its target molecule.

Nucleotide modulators can be of any length that allows effective binding to the ligand molecule. For example, oligonucleotide modulations can range in length from about 10 nucleotides (nt) to about 30 nt, from about 10 nt to about 20 nt, or from about 15 nt. The nucleotide modulators may be 8 nt, 9 nt, 10 nt, 11 nt, 12 nt, 13 nt, 14 nt, 15 nt, 16 nt, 17 nt, 18 nt, 19 nt, 20 nt, 21 nt, 22 nt, 23 nt, 24 nt, 25 n25, 26 nt, 27 nt, 28 nt, 29 nt or 30 nt in length. One having ordinary skill in the art can also envision nucleotide modulators having lengths greater than 30 nt.

A nucleic acid ligand as described herein possesses an active tertiary structure, which can be affected by formation of the appropriate stable secondary structure. Therefore, while the mechanism of formation of a duplex between a complementary oligonucleotide modulator of the invention and a nucleic acid ligand is similar to formation of a duplex between two short linear oligoribonucleotides, both the rules for designing such interactions and the kinetics of formation of such a product can be impacted by the intramolecular ligand structure.

The rate of nucleation of initial basepair formation between the nucleic acid ligand and oligonucleotide modulator plays a significant role in the formation of the final stable duplex, and the rate of this step is greatly enhanced by targeting the oligonucleotide modulator to single-stranded loops and/or single-stranded 3' or 5' tails present in the nucleic acid ligand. For the optimal formation of the intermolecular duplex to occur, the free energy is ideally favorable to the formation of the intermolecular duplex with respect to formation of the existing intramolecular duplexes within the targeted nucleic acid ligand.

The modulators described herein of the invention are generally oligonucleotides which comprise a sequence complementary to at least a portion of the targeted nucleic acid ligand sequence. For example, the modulator oligonucleotide can comprise a sequence complementary to about 6 nt to 25 nt, 8 nt to 20 nt, or 10 nt to 15 nt of the targeted ligand. The length of the modulator oligonucleotide can be readily optimized using techniques described herein and known to persons having ordinary skill in the art, taking into account the targeted ligand and the effect sought. The oligonucleotide can be made with nucleotides bearing D or L stereochemistry, or a mixture thereof. Naturally occurring nucleosides are in the D configuration.

While the oligonucleotide modulators of the invention include a sequence complementary to at least a portion of a nucleic acid ligand, absolute complementarity is not required. A sequence "complementary to at least a portion of an nucleic acid ligand," referred to herein, is a sequence having sufficient complementarity to be able to hybridize with the nucleic acid ligand. The ability to hybridize can depend on both the degree of complementarity and the length of the nucleic acid. Generally, the larger the hybridizing oligonucleotide, the more base mismatches with a target ligand it can contain and still form a stable duplex (or triplex as the case may, be). One skilled in the art can ascertain a tolerable degree of mismatch by use of standard procedures to determine the melting point of the hybridized complex. The oligonucleotides of the invention can be single-stranded DNA or RNA or chimeric mixtures or derivatives or modified versions thereof.

The modulators can include modifications in both the nucleic acid backbone and structure of individual nucleic acids. In certain embodiments, the modulator is a nucleic acid complementary to at least one loop region in the ligand. In some embodiments, the modulator is an oligonucleotide having at least a sequence that hybridizes at physiological conditions to the fourth loop in the two dimensional structure, and especially an oligonucleotide including a sequence 3'-AUU-5'. In other embodiments, the modulator is an oligonucleotide that hybridizes under physiological conditions to a first loop in the secondary structure of the ligand, and in particular an oligonucleotide including at least a sequence 3'-CUG-5'. Depending on the desired function of the modulator, the modulator can be designed to disrupt or stabilize the secondary and/or tertiary structure of the nucleic acid ligand.

In some embodiments, the modulator is designed to bind to a "suicide position" on the ligand and thereby disrupt the sequence of the ligand. A suicide position is a single stranded portion of the ligand susceptible to enzymatic cleavage. In one exemplary embodiment, the suicide position becomes single stranded and labile upon binding of the modulator to the ligand and can enhance cleavage of the ligand by enzymes in the circulation, such as blood or liver endonucleases. In certain embodiments, the modulator binds to the ligand after which the ligand can no longer interact with its target.

In one exemplary embodiment, the modulator includes a nucleic acid sequence selected from SEQ ID NO:74-88, inclusive.

In some embodiments, a modulator sequence comprises at least one modified nucleotide. For example, a 2'-O-methyl and 2'-fluoro modification, which can include 2'-O-methyl cytosine, 2'-O-methyl uridine, 2'-O-methyl adenosine, 2'-O-methyl guanosine, 2' fluoro cytidine, or 2' fluoro uridine.

Various strategies can be used to determine the optimal site within a nucleic acid ligand for binding by an oligonucleotide modulator. An empirical strategy can be used in which complimentary oligonucleotides are "walked" around the nucleic acid ligand. In accordance with this approach, oligonucleotides (e.g., 2'-O-methyl or 2'-fluoro oligonucleotides) about 15 nucleotides in length can be used that are staggered by about 5 nucleotides on the ligand (e.g., oligonucleotides complementary to 1-15, 6-20, 11-25, etc. of ligand). An empirical strategy can be particularly effective because the impact of the tertiary structure of the nucleic acid ligand on the efficiency of hybridization can be difficult to predict.

Assays described in the Examples that follow can be used to assess the ability of the different oligonucleotides to hybridize to a specific nucleic acid ligand, with particular emphasis on the molar excess of the oligonucleotide required to achieve complete binding of the nucleic acid ligand. The ability of the different oligonucleotide modulators to increase the rate of dissociation of the nucleic acid ligand from, or association of the ligand with, its target molecule can also be determined by conducting standard kinetic studies using, for example, BIACORE assays. Oligonucleotide modulators can be selected such that a 5-50 fold molar excess of oligonucleotide, or less, is required to modify the interaction between the ligand and its target molecule in the desired manner.

Alternatively, the targeted nucleic acid ligand can be modified so as to include a single-stranded tail (3' or 5') in order to promote association with an oligonucleotide modulator. Suitable tails can comprise 1 to 20 nucleotides, 1 to 10 nucleotides, 1 to 5 nucleotides or 3 to 5 nucleotides. Tails may also be modified (e.g., a 2'-O-methyl and 2'-fluoro modification, which can include 2'-O-methyl cytosine, 2'-O-methyl uridine, 2'-O-methyl adenosine, 2'-O-methyl guanosine, 2' fluoro cytidine, or 2' fluoro uridine). Tailed ligands can be tested in binding and bioassays (e.g., as described in the Examples that follow) to verify that addition of the single-stranded tail does not disrupt the active structure of the nucleic acid ligand. A series of oligonucleotides (for example, 2'-O-methyl oligonucleotides) that can form, for example, 1, 2, 3, 4 or 5 base pairs with the tail sequence can be designed and tested for their ability to associate with the tailed ligand alone, as well as their ability to increase the rate of dissociation of the ligand from, or association of the ligand with, its target molecule. Scrambled sequence controls can be employed to verify that the effects are due to duplex formation and not non-specific effects.

In another embodiment, the modulator is a ribozyme or a DNAzyme. Enzymatic nucleic acids act by first binding to a target RNA or DNA. Such binding occurs through the target binding portion of an enzymatic nucleic acid which is held in close proximity to an enzymatic portion of a molecule that acts to cleave the target RNA. Thus, the enzymatic nucleic acid first recognizes and then binds a target RNA or DNA through complementary base-pairing, and once bound to the correct site, acts enzymatically to cut the target RNA, thereby allowing for inactivation of RNA ligands. There are at least five classes of ribozymes that each display a different type of specificity. For example, Group I Introns are about 300 to >1000 nucleotides in size and require a U in the target sequence immediately 5' of the cleavage site and binds 4-6 nucleotides at the 5'-side of the cleavage site. Another class is RNaseP RNA (M1 RNA), which are about 290 to 400 nucleotides in size. A third class is Hammerhead Ribozymes, which are about 30 to 40 nucleotides in size. They require the target sequence UH (where H is not G) immediately 5' of the cleavage site and bind a variable number of nucleotides on both sides of the cleavage site. A fourth class is the Hairpin Ribozymes, which are about 50 nucleotides in size. They require the target sequence GUC immediately 3' of the cleavage site and bind 4 nucleotides at the 5'-side of the cleavage site and a variable number to the 3'-side of the cleavage site. A fifth group is Hepatitis Delta Virus (HDV) Ribozymes, which are about 60 nucleotides in size. DNAzymes are single-stranded, and cleave both RNA and DNA. A general model for the DNAzyme has been proposed, and is known as the "10-23" model. DNAzymes following the "10-23" model have a catalytic domain of 15 deoxyribonucleotides, flanked by two substrate-recognition domains of seven to nine deoxyribonucleotides each.

In another embodiment, the modulator itself is a nucleic acid ligand. In this embodiment, a first ligand is generated that binds to the desired therapeutic target. In a second step, a second ligand that binds to the first ligand is generated using the SELEX process described herein or another process, and modulates the interaction between the therapeutic ligand and the target. In one embodiment, the second ligand deactivates the effect of the first ligand.

In another exemplary embodiment, the modulator is a PNA, MNA, LNA, or PCO based modulator. Nucleobases of the oligonucleotide modulators of the invention can be connected via internucleobase linkages, e.g., peptidyl linkages (as in the case of peptide nucleic acids (PNAs); Nielsen et al. (1991) Science 254, 1497 and U.S. Pat. No. 5,539,082) and morpholino linkages (Qin et al., Antisense Nucleic Acid Drug Dev. 10, 11 (2000); Summerton, Antisense Nucleic Acid Drug Dev. 7, 187 (1997); Summerton et al., Antisense Nucleic Acid Drug Dev. 7, 63 (1997); Taylor et al., J Biol. Chem. 271, 17445 (1996); Partridge et al., Antisense Nucleic Acid Drug Dev. 6, 169 (1996)), or by any other natural or modified linkage. The oligonucleobases can also be Locked Nucleic Acids (LNAs). Nielsen et al., J Biomol Struct Dyn 17, 175 (1999); Petersen et al., J Mol Recognit 13, 44 (2000); Nielsen et al., Bioconjug Chem 11, 228 (2000).

PNAs are compounds that are analogous to oligonucleotides, but differ in composition. In PNAs, the deoxyribose backbone of oligonucleotide is replaced with a peptide backbone. Each subunit of the peptide backbone is attached to a naturally-occurring or non-naturally-occurring nucleobase. PNA often has an achiral polyamide backbone consisting of N-(2-aminoethyl)glycine units. The purine or pyrimidine bases are linked, to each unit via a methylene carbonyl linker (1-3) to target the complementary nucleic acid. PNA binds to complementary RNA or DNA in a parallel or antiparallel orientation following the Watson-Crick base-pairing rules. The uncharged nature of the PNA oligomers enhances the stability of the hybrid PNA/DNA(RNA) duplexes as compared to the natural homoduplexes.

Morpholino nucleic acids are so named because they are assembled from morpholino subunits, each of which contains one of the four genetic bases (adenine, cytosine, guanine, and thymine) linked to a 6-membered morpholine ring. Eighteen to twenty-five subunits of these four subunit types are joined in a specific order by non-ionic phosphorodiamidate intersubunit linkages to give a morpholino oligo.

LNA is a class of DNA analogues that possess some features that make it a prime candidate for modulators of the invention. The LNA monomers are bi-cyclic compounds structurally similar to RNA-monomers. LNA share most of the chemical properties of DNA and RNA, it is water-soluble, can be separated by gel electrophoreses, ethanol precipitated etc (Tetrahedron, 54, 3607-3630 (1998)). However, introduction of LNA monomers into either DNA or RNA oligos results in high thermal stability of duplexes with complementary DNA or RNA, while, at the same time obeying the Watson-Crick base-pairing rules.

Pseudo-cyclic oligonucleobases (PCOs) can also be used as a modulator in the present invention (see U.S. Pat. No. 6,383,752). PCOs contain two oligonucleotide segments attached through their 3'-3' or 5'-5' ends. One of the segments (the "functional segment") of the PCO has some functionality (e.g., complementarity to a target RNA). Another segment (the "protective segment") is complementary to the 3'- or 5'-terminal end of the functional segment (depending on the end through which it is attached to the functional segment). As a result of complementarity between the functional and protective segment segments, PCOs form intramolecular pseudo-cyclic structures in the absence of the target nucleic acids (e.g., RNA). PCOs are more stable than conventional oligonucleotides because of the presence of 3'-3' or 5'-5' linkages and the formation of intramolecular pseudo-cyclic structures. Pharmacokinetic, tissue distribution, and stability studies in mice suggest that PCOs have higher in vivo stability than and, pharmacokinetic and tissue distribution profiles similar to, those of PS-oligonucleotides in general, but rapid elimination from selected tissues. When a fluorophore and quencher molecules are appropriately linked to the PCOs of the present invention, the molecule will fluoresce when it is in the linear configuration, but the fluorescence is quenched in the cyclic conformation. This feature can be used to screen PCO's as potential modulators.

In another exemplary embodiment, the modulators are peptide-based modulators. Peptide-based modulators of nucleic acid ligands represent an alternative molecular class of modulators to oligonucleotides or their analogues. This class of modulators are particularly useful if sufficiently active oligonucleotide modulators of a target nucleic acid ligand cannot be isolated due to the lack of sufficient single-stranded regions to promote nucleation between the target and the oligonucleotide modulator. In addition, peptide modulators provide different bioavailabilities and pharmacokinetics than oligonucleotide modulators. In one exemplary embodiment the modulator is a protamine (Oney et al., 2009, Nat. Med. 15:1224-1228). Protamines are soluble in water, are not coagulated by heat, and comprise arginine, alanine and serine (most also contain proline and valine and many contain glycine and isoleucine). Modulators also include protamine variants (see e.g., Wakefield et al, J. Surg. Res. 63:280 (1996)) and modified forms of protamine, including those described in U.S. Publication No. 20040121443. Other modulators include protamine fragments, such as those described in U.S. Pat. No. 6,624,141 and U.S. Publication No. 20050101532. Modulators also include, generally, peptides that modulate the activity of heparin, other glycosaminoglycans or proteoglycans (see, for example, U.S. Pat. No. 5,919, 761). In one exemplary embodiment, modulators are peptides that contain cationic-NH groups permitting stabilizing charge-charge interactions such as poly-L-lysine and poly-L-ornithine.

Several strategies to isolate peptides capable of binding to and thereby modulating the activity of a target nucleic acid ligand are available. For example, encoded peptide combinatorial libraries immobilized on beads have been described, and have been demonstrated to contain peptides able to bind viral RNA sequences and disrupt the interaction between the viral RNA and a viral regulatory protein that specifically binds said RNA (Hwang et al. Proc. Natl. Acad. Sci. USA, 1999, 96:12997). Using such libraries, modulators of nucleic acid ligands can be isolated by appending a label to the target nucleic acid ligand and incubating together the labeled-target and bead-immobilized peptide library under conditions in which binding between some members of the library and the nucleic acid are favored. The binding of the nucleic acid ligand to the specific peptide on a given bead causes the bead to be "colored" by the label on the nucleic acid ligand, and thus enable the identification of peptides able to bind the target by simple isolation of the bead. The direct interaction between peptides isolated by such screening methods and the target nucleic acid ligand can be confirmed and quantified using any number of the binding assays described to identify modulators of nucleic acid ligands. The ability of said peptides to modulate the activity of the target nucleic acid ligand can be confirmed by appropriate bioassays.

In an additional embodiment, the modulators are oligosaccharide based modulators. Oligosaccharides can interact with nucleic acids. For example, the antibiotic aminoglycosides are products of *Streptomyces* species and interact specifically with a diverse array of RNA molecules such as various ribozymes, RNA components of ribosomes, and HIV-1's TAR and RRE sequences. Thus oligosaccharides can bind to nucleic acids and can be used to modulate the activity of nucleic acid ligands.

In another embodiment, the modulator is a small molecule based modulator. A small molecule that intercalates between the ligand and the target or otherwise disrupts or modifies the binding between the ligand and target can also be used as the therapeutic regulator. Such small molecules can be identified by screening candidates in an assay that measures binding changes between the ligand and the target with and without the small molecule, or by using an in vivo or in vitro assay that measures the difference in biological effect of the ligand for the target with and without the small molecule. Once a small molecule is identified that exhibits the desired effect, techniques such as combinatorial approaches can be used to optimize the chemical structure for the desired regulatory effect.

In a further exemplary embodiment, the modulator is a nucleic acid binding polymer, lipid, nanoparticle or microsphere. In further non-limiting examples, the modulator can be selected from the group consisting of: 1,2-dioleoyl-sn-glycero-3-ethylphosphocholine (EDOPC); dilauroylethylphosphatidylcholine (EDLPC); EDLPC/EDOPC; pyridinium surfactants; dioleoylphosphatidyl-ethanolamine (DOPE); (±)-N-(3-aminopropyl)-N,N-dimethyl-2,3-bis(dodecyloxy)-1-propanaminium bromide (GAP-DLRIE) plus the neutral co-lipid dioleoylphosphatidylethanolamine (DOPE) (GAP-DLRIE/DOPE); (±)-N,N-dimethyl-N-[2-(spermine carboxamido)ethyl]-2,3-bis(dioeyloxy-1-propaniminium petahydrochloride (DOSPA); dilauroylethylphosphatidylcholine (EDLPC); Ethyldimyristoyl phosphatidylcholine (EDMPC); (±)-N,N,N-trimethyl-2,3-bis(z-octadec-9-ene-oyloxy)-1-propanaminium chloride (DOTAP); (±)—N-2-(2-hydroxyethyl)-N,N-dimethyl-2,3-bis(tetradecyloxy)-1-propanaminium bromide (DMRIE); (±)-N,N,N-trimethyl-2,3-bis(z-octadec-9-enyloxy)-1-propanaminium chloride (DOTMA); 5-carboxyspermylglycine dioctadecyl-amide (DOGS); dipalmitoylphosphatidylethanolamine 5-carboxyspermylamide (DPPES); 1,3 dioleoyloxy-2-(6-carboxyspermyl)-propyl-amid (DOSPER); tetramethyltetrapalmitoyl spermine (TMTPS); (tetramethyltetraoleyl spermine (TMTOS); tetramethlytetralauryl spermine (TMTLS); tetramethyltetramyristyl spermine (TMTMS); tetramethyldioleyl spermine (TMDOS); diphytanoylphosphatidyl-ethanolamine (DPhPE); and (±)-N-(3-aminopropyl)-N,N-dimethyl-2,3-bis(dodecyloxy)-1-propanaminium bromide (GAP-DLRIE).

In other embodiments, the modulator is selected from the group consisting of: chitosan; a chitosan derivative; 1,5-dimethyl-1,5-diazaundecamethylene polymethobromide; polyoxyethylene/polyoxypropylene block copolymers; poly-L-lysine; polyamidoamine (PAMAM); β-cyclodextrin-containing polycation (CDP); β-cyclodextrin-containing polycation (imidazole-containing variant) (CDP-Im); polyphosphoramidate polymer (8 kDa, 30 kDa) (PPA-DPA 8 k, PPA-DPA 30 k); polybrene; spermine; PEG-block-PLL-dendrimers; polyethylenimine (PEI); mannose-PEI; transferin-PEI; linera-PEI (1PEI); gelatin; methacrylate/methacrylamide; poly(beta-amino esters); polyelectrolyte complexes (PEC); poly(vinalyamine) (PVA); Collagen; polypropylene imine (PPI); polyallylamine; polyvinylpyridine; aminoacetalized poly(vinyl alcohol); acrylic or methacrylic polymer; Newkome dendrimer; polyphenylene; dimethyldioctadecylammonium bromide (DAB); cetyltrimethylammonium bromide (CTAB); albumin; acid-treated gelatin; polylysine; polyornithine; polyarginine; DEAE-cellulose; DEAE-dextran; and poly(N,N-dimethylaminoethylmethacrylate); and polypropylamine (POPAM).

In one embodiment, the modulator is selected from chitosan and chitasan derivatives. Chitosan derivatives include water soluble chitosan nanoparticles (such as described in U.S. Pat. No. 6,475,995; US Patent Application No. 2006/0013885; Limpeanchob et al, (2006) Efficacy and Toxicity of Amphotericin B-Chitosan Nanoparticles; *Nareusan University Journal* 14(2):27-34). Given the polycationic nature of the chitosan polymer (essentially a very large polyamine polymer composed of repeating glucosamine monomers), chitosan may be used to aggregate and/or encapsulate ligands into a polyelectrolyte complex in vivo following injection into a host. This is based in part on interactions of the primary amines found on chitosan and the phosphodiester backbone of the ligand.

In certain embodiments, the primary amines on the chitosan polymer can be substantially modified to alter the water solubility and charge State. Chitosan derivatives include trimethyl chitosan chloride (TMC), which can be synthesized at different degrees of quaternization; mono-carboxymethylated chitosan (MCC) which is a polyampholytic polymer; glutaraldehyde cross-linked derivative (CSGA); thiolated chitosan (Lee, et al. (2007) *Pharm. Res.* 24:157-67); glycol chitosan (GC), a chitosan derivative conjugated with ethylene glycol (Lee, et al. (2007) *Int J. Pharm.*); [N-(2-carboxybenzyl)chitosan (CBCS) (Lin, et al. (2007) *Carbohydr Res.* 342 (1):87-95); a beta-cyclodextrin-chitosan polymer (Venter, et al. (2006) *Int J Pharm.* 313(1-2):36-42); O-carboxymethylchitosan; N,O-carboxymethyl chitosan; or a chitosan chemically modified by introducing xanthate group onto its backbone.

In one embodiment, empty chitosan nanoparticles are generated and used as modulators. Chitosan or chitosan derivatives of molecular weight range of 10,000 Da to >1,000,000 Da may be used. In certain embodiments, the chitosan is of 500,000 Da or less. In certain embodiments, the chitosan is of 100,000 Da or less. In some embodiments, the compound is between 10,000 and 100,000 Da, between 10,000 and 90,000, between 10,000 and 80,000, between 20,000 and 70,0000, between 30,000 and 70,000, about 30,000, about 40,000, about 50,000 or about 60,000 Da.

In some embodiments, chitosan polymers containing different degrees of deacetylated primary amines are used. In these embodiments, the different degrees of deacetylation alters the charge state of the polymer and thereby the binding properties of the polymer. Upon contact of the chitosan nanoparticle with ligands in the host, ligands may bind with and become trapped on the nanoparticle surface, or enter the nanoparticle and become encapsulated by ionic interactions.

In another embodiment, the modulator is a polyphosphate polymer microsphere. In certain embodiments, the modulator is a derivative of such a microsphere such as poly(L-lactide-co-ethyl-phosphite) or P(LAEG-EOP) and others, as described in U.S. Pat. No. 6,548,302. Such polymers can be produced to contain a variety of functional groups as part of the polymeric backbone. In one example, the polymers may contain quaternary amines with a positive charge at physiologic pH, such that they can complex or encapsulate one or more nucleic acids upon contact. In certain embodiments, the polymers do not contain positive charges.

The present invention also provides methods to identify the modulators of nucleic acid GPVI ligands. Modulators can be identified in general, through binding assays, molecular modeling, or in vivo or in vitro assays that measure the modification of biological function. In one embodiment, the binding of a modulator to a nucleic acid is determined by a gel shift assay. In another embodiment, the binding of a modulator to a nucleic acid ligand is determined by a BIACORE assay.

Standard binding assays can be used to identify and select modulators of the invention. Non-limiting examples are gel shift assays and BIACORE assays. That is, test modulators can be contacted with the nucleic acid ligands to be targeted under test conditions or typical physiological conditions and a determination made as to whether the test modulator in fact binds the ligand. Test modulators that are found to bind the nucleic acid ligand can then be analyzed in an appropriate bioassay (which will vary depending on the ligand and its target molecule, for example coagulation tests) to determine if the test modulator can affect the biological effect caused by the ligand on its target molecule.

The Gel-Shift assay is a well-known technique used to assess binding capability. For example, a DNA fragment containing the test sequence is first incubated with the test protein or a mixture containing putative binding proteins, and then separated on a gel by electrophoresis. If the DNA fragment is bound by protein, it will be larger in size and its migration will therefore be retarded relative to that of the free fragment. For example, one method for a electrophoretic gel mobility shift assay can be (a) contacting in a mixture a nucleic acid binding protein with a non-radioactive or radioactive labeled nucleic acid molecule comprising a molecular probe under suitable conditions to promote specific binding interactions between the protein and the nucleic acid in forming a complex, wherein said probe is selected from the group consisting of dsDNA, ssDNA, and RNA; (b) electrophoresing the mixture; and (c) detecting the complex bound to the membrane by detecting the non-radioactive or radioactive label in the complex.

The BIACORE technology measures binding events on the sensor chip surface, so that the interactant attached to the surface determines the specificity of the analysis. Testing the specificity of an interaction involves simply analyzing whether different molecules can bind to the immobilized interactant. Binding gives an immediate change in the surface plasmon resonance (SPR) signal, so that it is directly apparent whether an interaction takes place or not. SPR-based biosensors monitor interactions by measuring the mass concentration of biomolecules close to a surface. The surface is made specific by attaching one of the interacting partners. Sample containing the other partner(s) flows over the surface: when molecules from the sample bind to the interactant attached to the surface, the local concentration changes and an SPR response is measured. The response is directly proportional to the mass of molecules that bind to the surface.

SPR arises when light is reflected under certain conditions from a conducting film at the interface between two media of different refractive index. In the BIACORE technology, the media are the sample and the glass of the sensor chip, and the conducting film is a thin layer of gold on the chip surface. SPR causes a reduction in the intensity of reflected light at a specific angle of reflection. This angle varies with the refractive index close to the surface on the side opposite from the reflected light. When molecules in the sample bind to the sensor surface, the concentration and therefore the refractive index at the surface changes and an SPR response is detected. Plotting the response against time during the course of an interaction provides a quantitative measure of the progress of the interaction. The BIACORE technology measures the angle of minimum reflected light intensity. The light is not absorbed by the sample: instead the light energy is dissipated through SPR in the gold film. SPR response values are expressed in resonance units (RU). One RU represents a change of 0.0001° in the angle of the intensity minimum, for most proteins, this is roughly equivalent to a change in concentration of about 1 pg/mm$^2$ on the sensor surface. The exact conversion factor between RU and surface concentration depends on properties of the sensor surface and the nature of the molecule responsible for the concentration change.

There are a number of other assays that can determine whether an oligonucleotide or analogue thereof, peptide, polypeptide, oligosaccharide or small molecule can bind to the ligand in a manner such that the interaction with the target is modified. For example, electrophoretic mobility shift assays (EMSAs), titration calorimetry, scintillation proximity assays, sedimentation equilibrium assays using analytical ultracentrifugation (see for eg. www.cores.utah.edu/interaction), fluorescence polarization assays, fluorescence anisotropy assays, fluorescence intensity assays, fluorescence resonance energy transfer (FRET) assays, nitrocellulose filter binding assays, ELISAs, ELONAs (see, for example, U.S. Pat. No. 5,789,163), RIAs, or equilibrium dialysis assays can be used to evaluate the ability of an agent to bind to a nucleic acid ligand. Direct assays in which the interaction between the agent and the nucleic acid ligand is directly determined can be performed, or competition or displacement assays in which the ability of the agent to displace the ligand from its target can be performed (for example, see Green, Bell and Janjic, Biotechniques 30(5), 2001, p 1094 and U.S. Pat. No. 6,306,598). Once a candidate modulating agent is identified, its ability to modulate the activity of a nucleic acid ligand for its target can be confirmed in a bioassay. Alternatively, if an agent is identified that can modulate the interaction of a ligand with its target, such binding assays can be used to verify that the agent is interacting directly with the ligand and can measure the affinity of said interaction.

In another embodiment, mass spectrometry can be used for the identification of a modulator that binds to a nucleic acid ligand, the site(s) of interaction between the modulator and the nucleic acid ligand, and the relative binding affinity of agents for the ligand (see for example U.S. Pat. No. 6,329,146). Such mass spectral methods can also be used for screening chemical mixtures or libraries, especially combinatorial libraries, for individual compounds that bind to a selected target ligand that can be used in as modulators of the ligand. Furthermore, mass spectral techniques can be used to screen multiple target nucleic acid ligands simultaneously against, e.g. a combinatorial library of compounds. Moreover, mass spectral techniques can be used to identify interaction between a plurality of molecular species, especially "small" molecules and a molecular interaction site on a target ligand.

In vivo or in vitro assays that evaluate the effectiveness of a modulator in modifying the interaction between a nucleic acid ligand and a target are specific for the disorder being treated. There are ample standard assays for biological properties that are well known and can be used. Examples of biological assays are provided in the patents cited in this application that describe certain nucleic acid ligands for specific applications.

In some embodiments, a modulator is a small molecule. For example, in certain embodiments, a nucleic acid ligand is linked to a biotin molecule. In those instances, a streptavadin or avidin is administered to bind to and reverse the effects of the ligand (see Savi et. al. *J Thrombosis and Haemostasis,* 6: 1697-1706). Avidin is a tetrameric protein produced in the oviducts of birds, reptiles and amphibians which is deposited in the whites of their eggs. Streptavidin is a tetrameric protein purified from the bacterium *Streptomyces avidinii*. The tetrameric protein contains four identical subunits (homotetramer) each of which can bind to biotin (Vitamin B$_7$, vitamin H) with a high degree of affinity and specificity.

In certain embodiments, a modulator is a cationic molecule. In certain embodiments, the ligand forms a guanine quartet (G-quartet or G-quadruplex) structure. These structures are bound by cationic molecules. In certain embodiments, the molecules are metal chelating molecules. In some embodiments, the modulator is a porphyrin. In some embodiments, the compound is TMPyP4. See Joachimi, et. al. *JACS* 2007, 129, 3036-3037 and Toro, et. al. *Analytical Biochemistry* 2008, Aug. 1, 379 (1) 8-15.

In one embodiment, the modulator has the ability to substantially bind to a nucleic acid ligand in solution at modulator concentrations of less than ten (10.0) micromolar (uM), one (1.0) micromolar (uM), preferably less than 0.1 uM, and more preferably less than 0.01 uM. By "substantially" is meant that at least a 50 percent reduction in target biological activity is observed by modulation in the presence of the a target, and at 50% reduction is referred to herein as an $IC_{50}$ value.

F. OPTIMIZING LIGANDS AND MODULATORS

In order for a ligand to be suitable for use as a therapeutic, the ligand is preferably inexpensive to synthesize, safe for use in a host, and stable in vivo. Wild-type RNA and DNA oligonucleotides are typically not stable in vivo because of their susceptibility to degradation by nucleases. Resistance to nuclease degradation can be greatly increased by the incorporation of modifying groups at the 2'-position.

2'-fluoro or amino groups may be incorporated into oligonucleotide pools from which ligands have been subsequently selected. In the present disclosure, 2'-fluoropyrimidines were used in an in vitro transcription reaction to generate an initial oligonucleotide pool for ligand selection (see Example 1). However, resultant ligands selected from such libraries containing 2'-hydroxyl sugars at each purine position, so while more stable in vivo than a comparable RNA or DNA ligand, require additional optimization. Accordingly, the ligands identified using the methods described herein are subsequently modified in a variety of ways to obtain a ligand which has enhanced function and stability, as well as increased feasibility for large-scale manufacturing processes.

After initial identification of the ligands (via e.g., SELEX) and the modulators (e.g., design based on sequence complementarity), the ligands and modulators can be modified or engineered to improve their desired structure, function and/or stability by a variety of means. These include, but are not limited to, substituting particular sugar residues, changing the composition and size of particular regions and/or structures in the ligand, and designing ligands that can be more effectively regulated by a modulator.

The design and optimization of a nucleic acid ligand involves an appreciation for the secondary structure of the ligand as well as the relationship between the secondary structure and the modulator control. Unlike conventional methods of modifying nucleic acids, the design of the ligands to the GPVI protein may include consideration of the impact of changes to the ligand on the design of potential modulators. If a ligand is modified by truncation, for example, the corresponding modulator should be designed to control the truncated ligand.

The secondary structure of ligands identified through the SELEX process can be predicted by various methods known to persons having ordinary skill in the art. For example, each sequence may be analyzed using a software program such as Mfold (mfold.bioinfo.rpi.edu; see also Zuker, 2003, Nucleic Acids Res. 31:3406-3415 and Mathews, et al., 1999, J. Mol. Biol. 288:911-940). Subsequently, comparative sequence analysis of the various selected sequences can be used to align the sequences based upon conserved consensus secondary structural elements to arrive at a predicted secondary consensus structure for GPVI ligands (see Example 2). An analysis such as that described above allows one to design and test variants of the sequences obtained through SELEX to generate ligands with enhanced function and stability.

GPVI nucleic acid ligands of the present invention can be modified by varying overall ligand length as well as the lengths of the stem and loop structures. For example, ligand truncations may be generated in which a portion of the 5' and/or 3' end of a ligand is deleted from the ligand selected in the SELEX process. To determine the extent of truncations which are tolerated by a ligand, one method used can be to heat anneal an oligonucleotide (e.g. a DNA oligonucleotide) complementary to a 5' or 3' terminal region of the ligand, then compare binding of the ligand with and without the annealed oligonucleotide. If no significant binding difference is observed between the ligand with and the ligand without the annealed oligonucleotide, this suggests that the annealed portion of the ligand is dispensable for binding of the ligand to the target protein. This method can be performed using oligonucleotides which anneal to various lengths of the 5' or 3' ends of the ligand to determine 5' and 3' boundaries which provide a fully functional ligand.

In another embodiment, the design includes decreasing the size of the ligand. In another embodiment, the size of the modulator is changed in relation to the size of the ligand. In yet another embodiment, guanine strings are reduced to less than four guanine, or less than three guanine, or less than two guanine or no guanines. However, the joint effect of these changes must meet the challenge of creating a ligand that provides adequate activity but is easily neutralized by the modulator.

For targeting of a modulator, an improved ligand can also be modified so as to include a single-stranded tail (3' or 5') in order to promote association with an oligonucleotide modulator. Suitable tails can comprise 1 nt to 20 nt, preferably, 1 nt to 10 nt, 1 nt to 5 nt or 3 nt to 5 nt. It is readily understood that such tails may included modified nucleotides as described in more detail below.

Tailed ligands can be tested in binding and bioassays (e.g., as described below) to verify that addition of the single-stranded tail does not disrupt the active structure of the ligand. A series of oligonucleotides (for example, 2'-O-methyl oligonucleotides) that can form, for example, 1, 3 or 5 base-pairs with the tail sequence can be designed and tested for their ability to associate with the tailed ligand alone, as well as their ability to increase the rate of dissociation of the ligand from, or association of the ligand with, its target molecule. Scrambled sequence controls can be employed to verify that the effects are due to duplex formation and not non-specific effects.

Determination of a consensus structure also facilitates engineering of ligands to identify one or more nucleotides which may enhance or decrease ligand structure and function. For example, one may more efficiently identify and test nucleotide additions, deletions and substitutions to specific stem and loop structures (see Example 3).

Knowledge of a consensus secondary structure also allows one to avoid modifications which may be detrimental to ligand structure and function. For example, certain modifications may be conserved within the consensus secondary structure, such a 2'-fluoro within a stem or loop region. In these instances, removal of a 2'-fluoro from the stem or loop of an ligand may result in the loss of activity.

In certain embodiments, the ligands are nucleic acid molecules selected from Tables 1-7, including truncates and substantially homologous sequences thereof. As used herein, in the context of homologous regions, a "substantially homologous" sequence is one that forms the same secondary structure by Watson-Crick base pairing within a particular molecule. In certain embodiments, sequences are "substantially homologous" if they share at least 80%, 85% or more sequence identity, such as 90%, 91%, 92%, 93%, 94%, 95%, 96%, 97%, 98%, or 99% sequence identity to a specified ligand. In the context of a nucleic acid ligand of a specified length, such as 50 or less nucleotides, a homologous sequence can be found in any region that allows Watson-Crick binding to form the same secondary structure, regardless of sequence identity within the specific region.

Ligands may also be designed to have a suicide position, which allows more effective regulation by paired modulators. Upon binding of the ligand by the modulator, the suicide position becomes single stranded and labile, thereby facilitating cleavage of the ligand by enzymes naturally present in the blood, such as blood or liver endonucleases. This provides a means for effective and substantially immediate elimination of the active ligand from circulation.

Chemical Modifications

One problem encountered in the therapeutic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid ligand can increase the in vivo stability of the nucleic acid ligand or to enhance or to mediate the delivery of the nucleic acid ligand. Additionally, certain chemical modifications can increase the affinity of the nucleic acid ligand for its target, by stabilizing or promoting the formation of required structural elements within the nucleic acid ligand or providing additional molecular interactions with the target molecule.

Modifications of the ligands can include, but are not limited to, those which provide chemical groups that incorporate additional charge, polarizability, hydrophobicity, hydrogen bonding, electrostatic interactions, and functionality to the nucleic acid ligand bases or to the ligand as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo dr 5-iodo-uracil, backbone modifications, phosphorothioate or alkyl phosphate modifications, methylations, unusual base-pairing combinations such as the isobases isocytidine and isoguanidine and the like. Modifications can also include 3' and 5' modifications such as capping.

The SELEX method encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX-identified nucleic acid ligands containing modified nucleotides are described in U.S. Pat. No. 5,660,985 that describes oligonucleotides containing nucleotide derivatives chemically modified at the 5- and 2'-positions of pyrimidines. U.S. Pat. No. 5,580,737 describes specific nucleic acid ligands containing one or more nucleotides modified with 2'-amino (2'—$NH_2$), 2'-fluoro (2'-F), and/or 2'-O-methyl (2'-OMe). U.S. Pat. No. 5,756,703, describes oligonucleotides containing various 2'-modified pyrimidines.

The SELEX method encompasses combining selected oligonucleotides with other selected oligonucleotides and non-oligonucleotide functional units as described in U.S. Pat. Nos. 5,637,459 and 5,683,867. U.S. Pat. No. 5,637,459 describes highly specific nucleic acid ligands containing one or more nucleotides modified with 2'-amino (2'-$NH_2$), 2'-fluoro (2'-F), and/or 2'-O-methyl (2'-OMe). The SELEX method further encompasses combining selected nucleic acid ligands with lipophilic or Non-Immunogenic, High Molecular Weight compounds in a diagnostic or therapeutic complex as described in U.S. Pat. No. 6,011,020.

Where the nucleic acid ligands are derived by the SELEX method, the modifications can be pre- or post-SELEX modifications. Pre-SELEX modifications can yield ligands with both specificity for its target and improved in vivo stability. Post-SELEX modifications made to 2'-hydroxyl (2'-OH) nucleic acid ligands can result in improved in vivo stability without adversely affecting the binding capacity of the nucleic acid ligands. In one embodiment, the modifications of the ligand include a 3'-3' inverted phosphodiester linkage at the 3' end of the molecule, and 2' fluoro (2'-F), 2' amino (2'—$NH_2$), 2' deoxy, and/or 2' O methyl (2'-OMe) modification of some or all of the nucleotides.

The ligands described herein were initially generated via SELEX using libraries of transcripts in which the C and U residues were 2'-fluoro substituted and the A and G residues were 2'-OH. While such modifications generate ligand molecules suitable for screening, the high 2' hydroxyl content make them unsuitable for drug development candidates due to the fact that these positions can be very sensitive to nuclease degradation in vivo, limiting the maximal concentration that can be achieved post-parenteral administration as well as their circulating half-life. Accordingly, once functional sequences are identified, such as through the SELEX method, individual residues can be tested for tolerance to substitutions by assessing the effects of these substitutions on ligand structure, function and stability.

In certain embodiments, the nucleic acids making up the ligand include modified sugars and/or modified bases. In certain embodiments, the modifications include stabilizing modifications such as 2'-stabilizing modifications. In one embodiment, 2'-stabilizing modifications can include 2'-fluoro, 2' deoxy or 2'-O-methyl modifications on the sugar ring.

In one embodiment, the design includes decreasing the 2'-hydroxyl content of the ligand or the modulator, or both. In another embodiment, the design includes decreasing the 2'-fluoro content of the ligand or the modulator, or both. In another embodiment, the design includes increasing the 2'-O-methyl content of the ligand or the modulator, or both.

The oligonucleotide can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2α-thiouracil, β-D-mannosylqueosine, 5'-methoxycarboxymethyluracil, 5-methoxyuracil, 2-methylthio-N&isopentenyladenine, uracil oxyacetic acid, wybutoxosine, pseudouracil, queosine, 2-thiocytosine, 5-methyl thiouracil, 2-thiouracil, 4-thiouracil, 5-methyluracil, -uracil-5-oxyacetic acid methylester, uracil oxyacetic acid (v), 5-methyl thiouracil, 3-(3-amino-3-N carboxypropyl) and 2,6-diaminopurine.

The oligonucleotides of the presently described ligands and modulators can comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. In another embodiment, the nucleic acid ligand or modulator of the invention can comprise at least one modified sugar moiety selected from the group including, but not limited to, arabinose, 2-fluoroarabinose, xylulose, hexose, 2'-fluororibose, 2'-O-methylribose, 2'-O-methoxyethylribose, 2'-O-propylribose, 2'-O-methylthioethylribose, 2'-O-diethylaminooxyethylribose, 2'-O-(3- aminopropyl)ribose, 2'-O-(dimethylaminopropyl)ribose, 2'-O-(methylacetamido)ribose, and 2'-O-(dimethylaminoethyloxyethyl)ribose.

The ligand or modulator can comprise at least one modified phosphate backbone selected from the group including, but not limited to, a phosphorothioate, a phosphorodithioate, a phosphoramidothioate, a phosphoramidate, a phosphorodiamidate, a methylphosphonate, an alkyl phosphotriester, and a formacetal or analog thereof.

Figure 13A:
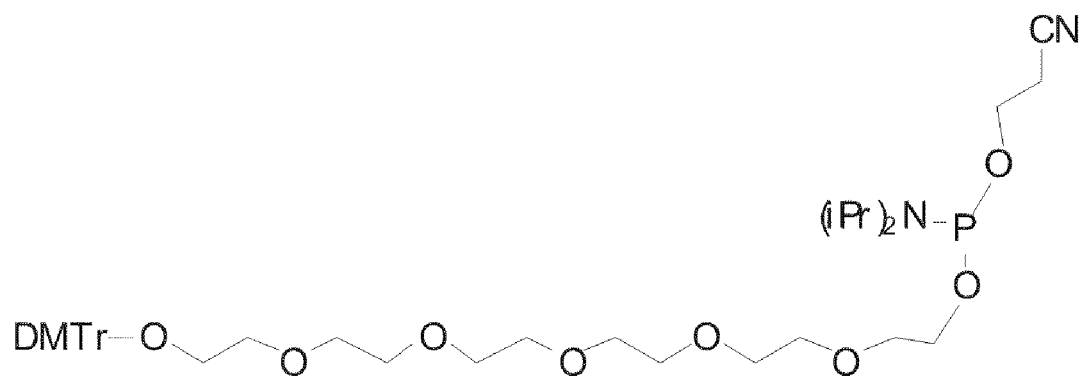
FIG. 13A-B illustrate a hexaethylene glycol spacer phosphoramidite and the spacer phosphoramidite incorporated between two nucleotides in a nucleic acid sequence.
Figure 13B:
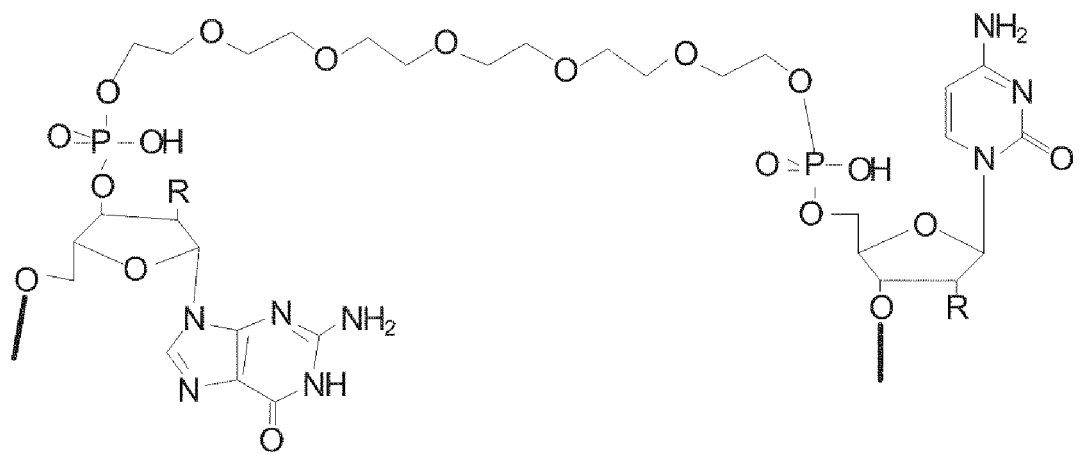

The ligand molecule, which comprises stem and loop structures, may be further stabilized for therapeutic use by the substitution of one or more nucleic acid loop structures with a more stable loop structure. For example, for the GPVI ligands described herein, it was discovered that substitution of Loop 2 with a hexaethylene glycol spacer resulted in GPVI ligands with similar affinity and anti-GPVI ligands with nucleotidyl loop. FIG. 13A illustrates the starting phosphoramidite for a hexaethylene glycol linker used in synthesis. FIG. 13B illustrates the hexaethylene glycol spacer when incorporated between two nucleotides of a nucleic acid ligand.

In pharmaceutical compositions the ligands can be provided in forms, such as salt forms that improve solubility or bioavailability.

Any of the oligonucleotides of the invention can be synthesized by standard methods known in the art, e.g. by use of an automated DNA synthesizer (such as are commercially available from, for example, Biosearch, Applied Biosystems).

Ligands and modifiers are described herein using abbreviations readily understood by a skilled artisan and noted as follows: "rA" is 2'OH A or adenosine; "A" is a 2'-deoxy A or 2'-deoxyadenosine; "mA" is 2'-O-methyl A or 2'-methoxy-2'-deoxyadenine; "rG" is 2'-OH G or guanosine; "G" is a 2'-deoxy G or 2'-dexoyguanosine; "mG" is 2'-O-methyl G or 2'-methoxy-2' dexoyguanosine; "fC" is 2'-fluoro C or 2'-fluoro-2' dexoycytidine; "mC" is 2'-O-methyl C or methoxy-2'-dexoycytidine; "fU" is 2'-fluoro U or 2'-fluoro-uridine; "mU" is 2'-O-methyl U or 2'-methoxy-uridine; and "iT" is inverted 2'H T, (C6L) is a hexylamino linker; (6GLY) is a hexaethylene glycol spacer; (PEG40KGL2-NOF) is an approximately 40 kDa Branched PEG (SUNBRIGHT™ product No. GL2-400GS2), (6FAM) is 6-carboxyfluorescein; (s) is a phosphorothioate linkage between two nucleotides.

Coupling to a Carrier

The GPVI ligands can also include modifications that improve bioavailability or stability. Such modifications can include conjugation to a carrier molecule which may include, but is not limited to a hydrophilic or hydrophobic moiety. One example is polyethylene glycol molecules conjugated to the nucleic acid sequence. Conjugation to, for example, a polymer as described below, can confine distribution to the plasma compartment and increase circulating half-life.

Sugar modifications, as described above, can ensure stability but they do not guarantee adequate pharmacokinetics for nucleic acid ligands to be therapeutically active. In healthy individuals, ligands are cleared from plasma within minutes of IV injection, probably through renal excretion. Keeping intact ligands in the blood from hours to days after injection has been accomplished by conjugating them to larger macromolecules such as polyethylene glycol (PEG). Ligand plasma clearance has also been decreased by embedding them in liposomes.

Therefore, in one embodiment, the GPVI nucleic acid ligand or GPVI ligand modulator can be covalently bound or otherwise attached to a non-immunogenic, high molecular weight compound such as polyethylene glycol (PEG) or other water soluble pharmaceutically acceptable polymer including, but not limited to, polyaminoamines (PAMAM); polysaccharides such as dextran, or polyoxazolines (POZ). The GPVI nucleic acid ligand or GPVI ligand modulator can be associated with the high molecular weight compound through covalent bonds. Where covalent attachment is employed, the high molecular weight compound may be covalently bound to a variety of positions on the ligand or modulator. In some embodiments, the ligand or the modulator can be encapsulated inside a liposome for administration to a host in need thereof.

In one embodiment, the ligand or modulator is attached to polyethylene glycol (PEG). Polyethylene glycols (PEGs) can be conjugated to biologically active compounds to serve as "inert" carriers to potentially (1) prolong the half-life of the compound in the circulation, (2) alter the pattern of distribution of the compound and/or (3) camouflage the compound, thereby reducing its immunogenic potential and protecting it from enzymatic degradation.

The ligand or modulator can attached to the PEG molecule through covalent bonds. For example, an oligonucleotide ligand or modulator can be bonded to the 5'-thiol through a maleimide or vinyl sulfone functionality.

Typically, activated PEG and other activated water-soluble polymers are activated with a suitable activating group appropriate for coupling to a desired site on the therapeutic agent. Representative polymeric reagents and methods for conjugating these polymers to an active agent are known in the art and further described in, e.g., Zalipsky, S., et al., "Use of Functionalized Poly(Ethylene Glycols) for Modification of Polypeptides" in Polyethylene Glycol Chemistry: Biotechnical and Biomedical Applications, J. M. Harris, Plenus Press, New York (1992); and in Zalipsky, Advanced Drug Reviews, 1995, 16:157-182. Such reagents are also commercially available.

For example, in one approach for preparing an amide-linked conjugate, a water soluble polymer bearing an activated ester such as an NHS ester, e.g., mPEG-succinimidyl-α-methylbutanoate, is reacted with an amine group of the active agent to thereby result in an amide linkage between the active agent and the water-soluble polymer. Additional functional groups capable of reacting with reactive amino groups include, e.g., N-hydroxysuccinimidyl esters, p-nitrophenylcarbonates, succinimidylcarbonates, aldehydes, acetals, N-keto-piperidones, maleimides, carbonyl imidazoles, azalactones, cyclic imide thiones, isocyanates, isothiocyanates, tresyl chloride, and halogen formates, among others.

In one embodiment, a plurality of GPVI ligands or GPVI ligand modulators can be associated with a single PEG molecule. The ligands and modulators can be the same or different sequences and modifications. In yet a further embodiment, a plurality of PEG molecules can be attached to each other. In this embodiment, one or more GPVI ligands or GPVI ligand modulators to the same GPVI protein target sequence or different GPVI protein sequence targets can be associated with each PEG molecule. In embodiments where multiple ligands or modulators specific for the same target are attached to PEG, there is the possibility of bringing the same targets in close proximity to each other in order to generate specific interactions between the same targets. Where multiple ligands or modulators specific for different targets are attached to PEG, there is the possibility of bringing the distinct targets in close proximity to each other in order to generate specific interactions between the targets.

Figure 14A:
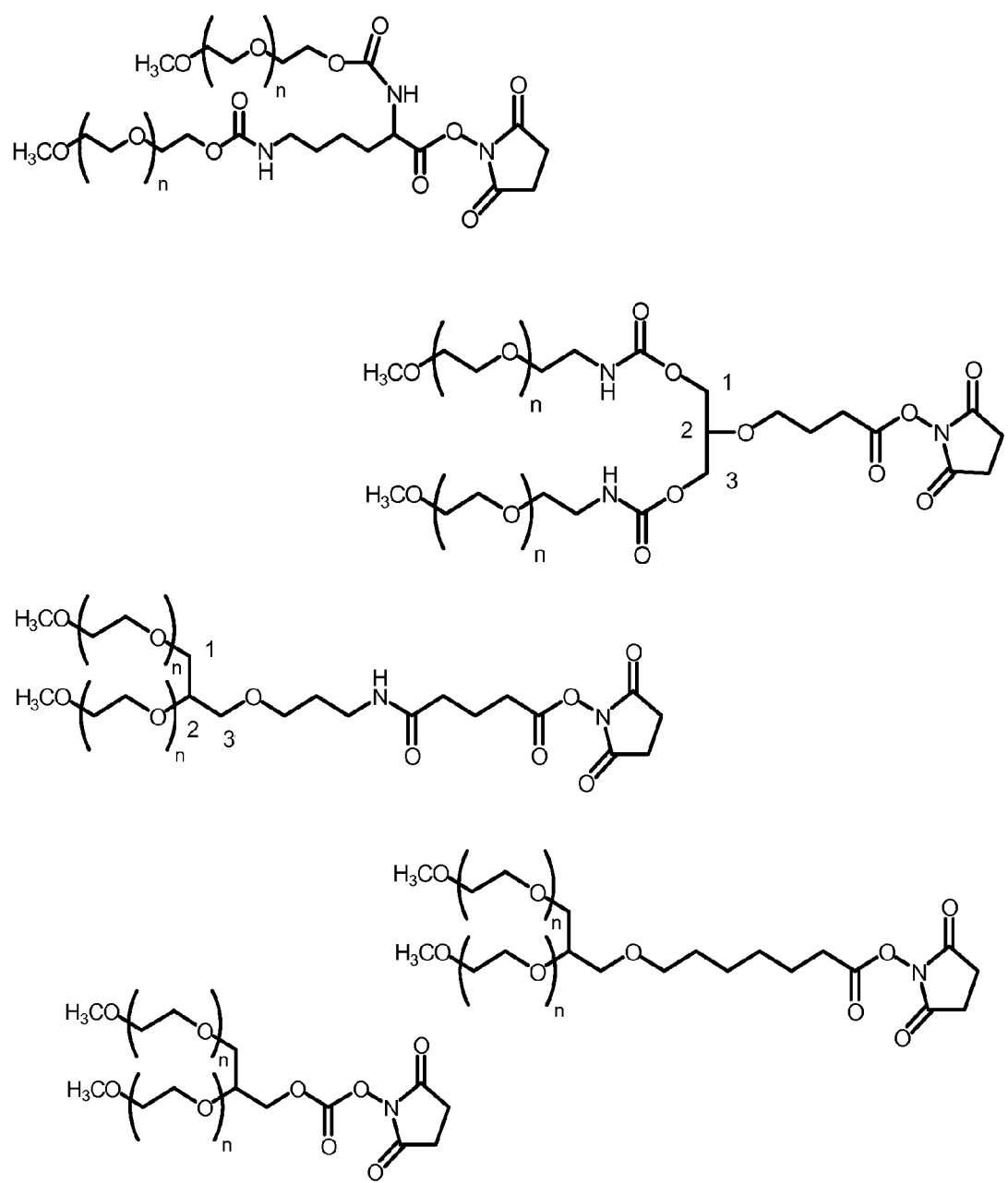
FIGS. 14A-B shows PEG moieties which may be conjugated to a GPVI ligand via a linker and a configuration of a conjugated moiety.
Figure 14B:
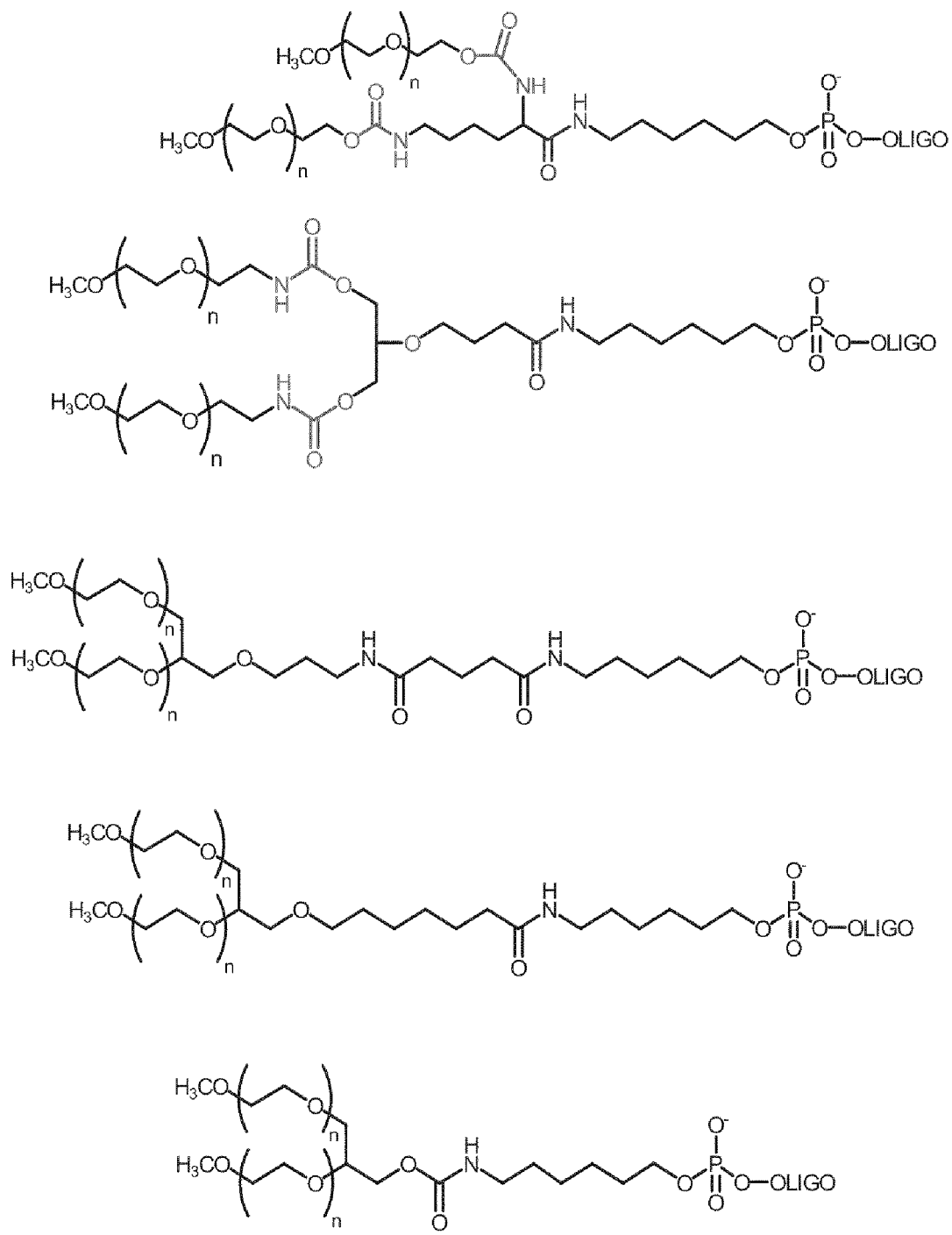

While a variety of linkers and methods for conjugation of hydrophilic moieties such as PEG molecules are well known to persons in the art, several embodiments are provided below. In one embodiment, an amino linker, such as the C 6 hexylamino linker, 6-(trifluoroacetamido)hexanol (2-cyanoethyl-N,N-diisopropyl)phosphoramidite, shown in FIG. 14, can be used to add the hexylamino linker to the 5' end of the synthesized oligonucleotide. Other linker phosphoramidites that may be used to add linkers to the synthesized oligonucleotides are described below:

TFA-amino C4 CED phosphoramidite (available from ChemGenes, cat #CLP-1453) of the structure:

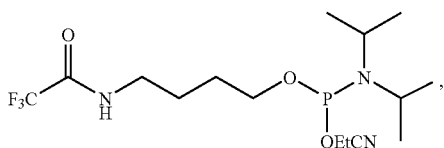

5'-amino modifier C3 TFA (available from Glen Research cat #10-1923-90) of the structure:

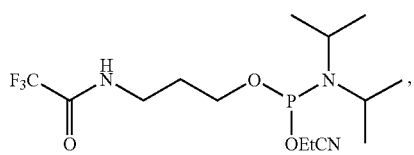

5'-Amino-Modifier C3-TFA

5'-amino modifier 5 (available from Glen Research cat #10-1905-90) of the structure:

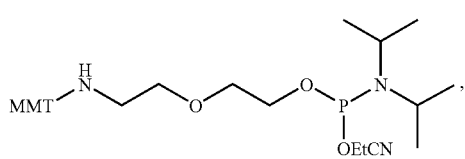

MMT: 4-Monomethoxytrityl

5'-Amino Modifier 5

5'-amino modifier C12 (available from Glen Research cat #10-1912-90) of the structure:

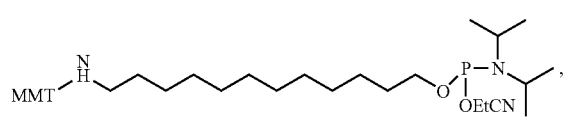

MMT: 4-Monomethoxytrityl

5'-Amino-Modifier C12

5' thiol-modifier C6 (available from Glen Research cat #10-1926-90) of the structure:

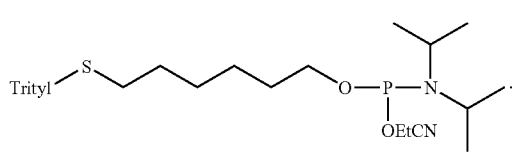

The 5'-thiol modified linker is used with PEG-maleimides, PEG-vinylsulfone, PEG-iodoacetamide and PEG-orthopyridyl-disulfide, for example.

The PEG can range in size from 5 to 200 KD, with typical PEGs used in pharmaceutical formulations in the 10-60 KD range. Linear chain PEGs of up to about 30 KD can be produced. For PEGs of greater than 30 KD, multiple PEGs can be attached together (multi-arm or 'branched' PEGs) to produce PEGs of the desired size. The general synthesis of compounds with a branched, "mPEG2" attachment (two mPEGs linked via an amino acid) is described in Monfardini, et al., Bioconjugate Chem. 1995, 6:62-69. For 'branched' PEGs, i.e. compounds that include more than one PEG or mPEG linked to a common reactive group, the PEGs or mPEGS can be linked together through an amino acid such as a lysine or they can be linked via, for example, a glycerine. For branched PEGs in which each mPEG is about 10, about 20, or about 30 KD, the total mass is about 20, about 40 or about 60 KD and the compound is referred to by its total mass (i.e. 40 KD mPEG2 is two linked 20 kD mPEGs). 40 KD total molecular weight PEGs, that can be used as reagents in producing a PEGylated compound, include, for example, [$N^2$-(monomethoxy 20K polyethylene glycol carbamoyl)-$N^6$-(monomethoxy 20K polyethylene glycol carbamoyl)]-lysine N-hydroxysuccinimide of the structure:

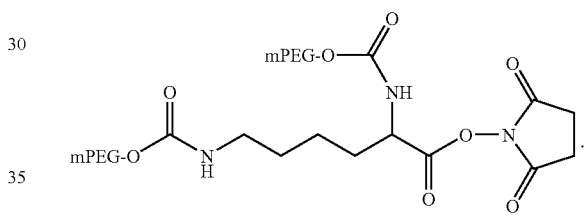

Additional PEG reagents that can be used to prepare stabilized compounds of the invention include other branched PEG N-Hydroxysuccinimide (mPEG-NHS) of the general formula:

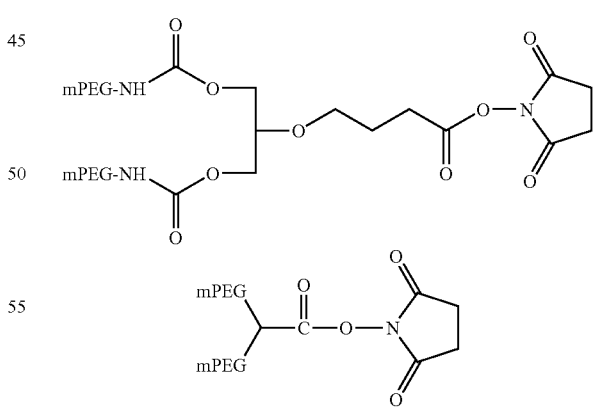

with a 40 KD or 60 KD total molecular weight (where each mPEG is about 20 or about 30 KD). As described above, the branched PEGs can be linked through any appropriate reagent, such as an amino acid, and in certain embodiments are linked via lysine residues or glycerine residues.

They can also include non-branched mPEG-Succinimidyl Propionate (mPEG-SPA), of the general formula:

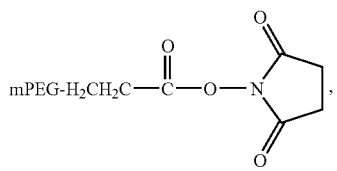

in which mPEG is about 20 KD or about 30 KD. In a specific embodiment, the reactive ester is —O—CH2CH2-CO2-NHS.

The reagents can also include a branched PEG linked through glycerol, such as the Sunbright™ series from NOF Corporation, Japan. Specific, non-limiting examples of these reagents are:

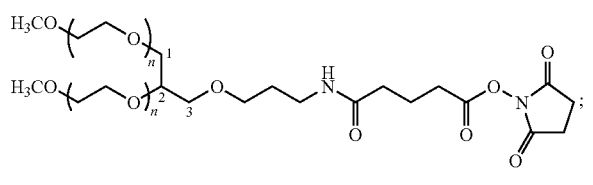

(SUNBRIGHT GL2-400GS2)

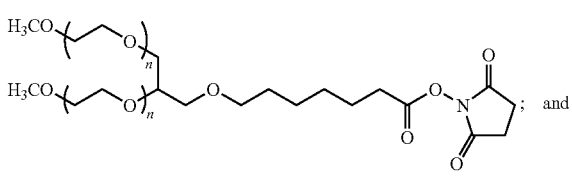

(SUNBRIGHT GL2-400HS)

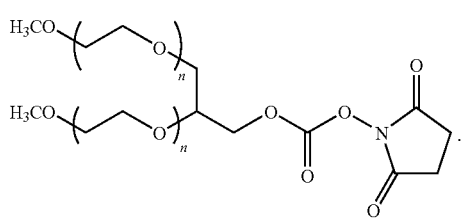

(SUNBRIGHT GL2-400TS)

The reagents can also include non-branched Succinimidyl alpha-methylbutanoate (mPEG-SMB) of the general formula:

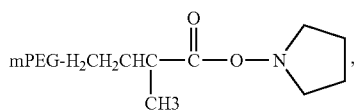

in which mPEG is between 10 and 30 KD. In a subembodiment, the reactive ester is —O—CH$_2$CH$_2$CH(CH$_3$)—CO$_2$—NHS. Compounds of this structure are sold by Nektar Therapeutics as catalog numbers cat #2M4K0R01.

PEG reagents can also include nitrophenyl carbonate linked PEGs, such as of the following structure:

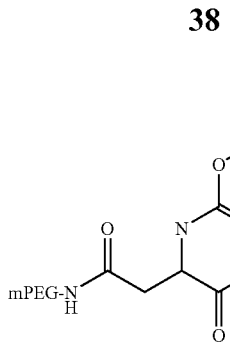

Compounds of this structure are commercially available, for example from Sunbio, Inc. Compounds including nitrophenyl carbonate can be conjugated to primary amine containing linkers. In this reaction, the O-nitrophenyl serves as the leaving group, leaving a structure [mPEG]$_n$-NH—CO—NH-linker-ligand.

PEGs with thiol-reactive groups that can be used with a thiol-modified linker, as described above, include compounds of the general structure:

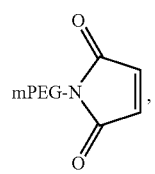

in which mPEG is about 10, about 20 or about 30 KD. Additionally, the structure can be branched, such as

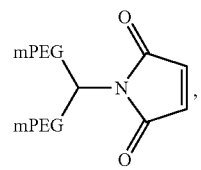

in which each mPEG is about 10, about 20, or about 30 KD and the total mass is about 20, about 40, or about 60 KD. Branched PEGs with thiol reactive groups that can be used with a thiol-modified linker, as described above, include compounds in which the branched PEG has a total molecular weight of about 40 or 60 KD (where each mPEG is 20 or 30 KD). PEG reagents can also be of the following structure:

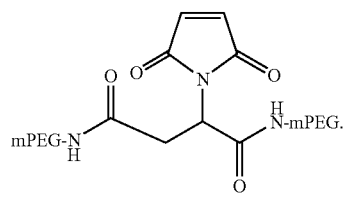

PEG-maleimide pegylates thiols of the target compound in which the double bond of the maleimic ring breaks to connect with the thiol. The rate of reaction is pH dependent and, in one embodiment, is carried out between pH 6 and 10, or between pH 7 and 9 or about pH 8.

In one embodiment, a plurality of GPVI ligand modulators can be associated with a single PEG molecule. The modulator can be to the same or different GPVI nucleic acid ligands. In embodiments where there are multiple modulators to the same ligand, there is an increase in avidity due to multiple binding interactions with the ligand. In yet a further embodiment, a plurality of PEG molecules can be attached to each other. In this embodiment, one or more modulators to the same nucleic acid ligand or different ligands can be associated with each PEG molecule. This also results in an increase in avidity of each modulator to its target.

In one embodiment, the nucleic acid ligand or its modulator can be covalently attached to a lipophilic compound such as cholesterol, dialkyl glycerol, or diacyl glycerol. The lipophilic compound or non-immunogenic, high molecular weight compound can be covalently bonded or associated through non-covalent interactions with a ligand or modulator(s). Attachment of the ligand or oligonucleotide modulator to lipophilic or non-immunogenic high molecular weight compounds can be done directly or with the utilization of linkers or spacers.

In embodiments where direct covalent attachment is employed, the lipophilic compound or non-immunogenic high molecular weight compound may be covalently bound to a variety of positions on the ligand or modulator, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus.

In embodiments where the ligand or modulator is attached to a lipophilic, or a non-immunogenic high molecular weight compound through a linker or spacer, the lipophilic compound or non-immunogenic high molecular weight compound may be attached to the ligand or modulator using, for example, a six carbon amino linker.

In another embodiment, one or more phosphate groups may be included between the linker and the nucleic acid sequence.

Additional suitable linkers and spacers for attaching the ligand or modulator to a lipophilic compound or to a non-immunogenic high molecular weight compound are described in U.S. Pat. No. 7,531,524, incorporated herein by reference.

Oligonucleotides of the invention can be modified at the base moiety, sugar moiety, or phosphate backbone, for example, to improve properties such as stability of the molecule and affinity for the intended target.

G. METHODS TO TREAT PLATELET-MEDIATED DISORDERS

Platelets contain two physiologically important collagen receptors, GPVI and the integrin $\alpha_2\beta_1$. Of these, platelet activation in response to collagen is mediated through GPVI. Activation of platelets by the interaction of collagen with GPVI leads to release of both dense and alpha-granule contents from platelets. Granule constituents include a number of platelet agonists as well as pro-inflammatory cytokines, growth factors, adhesion molecules and other proteins including: ATP, GTP, ADP, GDP, polyphosphate, CD63, LAMP2, serotonin, platelet factor 4, $\beta$-thromboglobulin, MIP-1$\alpha$, RANTES, MCP-3, CCL17, CXCL1, CXCL5, IL-8, BFGF, EGF, HGF, insulin-like growth factor 1, TGF-$\beta$, VEGF-A, VEGF-C, PDGF, P-Selectin, vWF, thrombospondin, fibrinogen, integrins $\alpha_{II}\beta_3$ and $\alpha_v\beta_3$, fibronectin, albumin, $\alpha_1$-trypsin, Gas6, histidine-rich glycoprotein, high molecular weight kininogen, and amyoid beta-protein precursor. Thus, platelet activation via the GPVI interaction with collagen locally creates a pro-inflammatory environment capable of stimulating a wide range of nearby cell types.

The interaction of GPVI with collagen is also required for platelet adhesion to the diseased or damaged vessel wall. Finally, the activation of GPVI by collagen triggers platelet aggregation. GPVI activation by collagen plays an important role in hemostasis when vessel damage exposes vascular collagen, thus leading to formation of a platelet plug. While the role of platelets in thrombosis is well understood and is mediated generally by interaction of GPVI with collagen types I and III present in the sub-endothelial matrix and enriched in atherosclerotic plaques, more recent data indicate that the pro-inflammatory responses of platelets upon activation can underlie a myriad of disease states in addition to thrombotic diseases, including atherosclerosis, diabetic vascular disease, rheumatoid arthritis and scleroderma. For example, the interaction of GPVI with collagen can lead to disease states when the expression of GPVI is abnormally high, or when platelets are exposed to collagen at pathophysiologic levels, or when platelets are exposed to collagen in an abnormal distribution. Accordingly, provided herein are methods for the treatment of platelet-mediated diseases or disorders using therapeutically effective amounts of GPVI ligands. These GPVI ligands can function by binding to and inhibiting platelet activation.

To understand diseases in which anti-GPVI therapies can produce a therapeutic effect, the specificity of GPVI for the various collagen types found in the body need only be understood, as platelet activation by collagen requires the collagen be capable of interacting with GPVI. There are 29 different types of collagen. Of these, 9 have been identified to be expressed in the vasculature, including types I, III, IV, V, VI, VIII, XII, XIII and XIV. Additionally, of these, 7 are fibrillar and able to assemble into stable triple helices and higher-order fibrous structures, including types I, II, III, IV, V, XI, XXIV and XXVII (Nieswandt et al., Blood, 2003, 102:449-461; Herr et al., J. Biol. Chem., 2009, 284:19781-19785). It has been shown that fibril forming collagens, types I, II, III and IV, support platelet activation, aggregation and adhesion, while the non-fibrillar collagens, types VI, VII and VIII, induce only weak adhesion with no platelet aggregation. Thus, collagen types I-IV can interact with GPVI to specifically activate platelets. Additionally, GPVI has been shown to specifically bind collagen types I-IV (Jung et al., Platelets, 2008; 19:32-42). Thus, diseases in which high expression of collagen types I-IV, or in which abnormal localization or presentation of these collagen types to platelets occur, can be treated with GPVI ligands.

The structural requirements for GPVI binding by collagen and collagen-related peptides is well understood (see Example 6; also Smethurst et al., J. Biol. Chem., 2007, 282: 1296-1304; Smethurst et al., Blood, 2004, 103:903-911; Horii et al., Blood, 2008:936-942). One of the primary recognition sites of GPVI within collagen fibrils is the tripeptide sequence GPO. In addition, the collagen binding grooves in GPVI are separated by roughly 5.5 nm. Therefore, other collagen types which contain GPO repeats, and which form fibrillar structures capable of displaying GPO repeats at unit distance of ~5.5 nm such that they are capable of binding GPVI dimers, are expected to activate platelets via GPVI, leading to diseases treatable with GPVI ligands.

GPVI is typically expressed at low to moderate levels on platelets; with a typical receptor number of ~1200/platelet. However, increased levels of GPVI expression can make platelets hyper-reactive to collagen, and thus predispose individuals to a disease, or directly cause a disease state mediated by the platelet-collagen interaction. Overexpression of GPVI has been linked to the onset of thrombotic vascular diseases, including transient ischemic attacks (TIA) and acute coronary syndromes (Bigalke et al., Thromb. Res., 2010:125: e184-189; Bigalke et al., Int. J. Cardiol., 2009, Jan. 11 epub; Bigalke et al., Clin. Res. Cardiol., 2010, 99:227-233). Therefore, treatment of cerebrovascular events such as TIA and stroke, or treatment of acute coronary syndromes with GPVI ligands, can yield a therapeutic effect.

Common molecular mechanisms underlie the role of platelets in hemostasis and inflammatory reactions. For example, in the presence of vascular endothelial damage such as in diabetes and in atherothrombotic vascular disease, there is a high level of GPVI platelet activation. This results in the release of cytokines and activation, localization and maturation of white blood cells. The generation and perpetuation of this process in the presence of atherosclerotic vascular disease also leads to the adhesion of platelets to the endothelial surface, destabilizing plaques and leading to further vascular injury. This combination of events can result in ischemia in the vessel. Thus, a therapeutic such as a GPVI ligand, which prevents or reduces unwanted activation of platelets, can be used to treat a variety of diseases known to be associated with, for example, upregulation of GPVI expression on platelets or increased activation of platelets by increased exposure to collagen.

Diabetes is associated with enhanced collagen-mediated platelet activation, and GPVI expression is significantly higher in individuals with diabetes as compared to those without (Cabeza et al., Diabetes, 2004, 53:2117-2121). High GPVI expression in diabetics contributes significantly to the thromboischemic complications associated with diabetes, and thus anti-GPVI therapies can yield a therapeutic effect in the treatment of diabetic related thromboischemic diseases. Activation of GPVI significantly enhances surface expression of CD40L. CD40L is a potent platelet-derived cytokine involved in thrombosis and atherosclerosis. Furthermore, CD40L overexpression in GPVI-activated platelets enhances endothelial surface expression of CD62P, $\alpha v \beta 3$, intercellular adhesion molecule 1, and secretion of monocyte chemoattractant protein 1. These results indicate that the function of collagen receptor GPVI is altered in type 2 diabetes and can play an important role in diabetic atherothrombotic complications and localized vascular disease.

Accordingly, GPVI ligands can be used to treat a variety of platelet-mediated disorders commonly associated with diabetes. In one embodiment, a method of treating a subject suffering from diabetes is provided, comprising administration of a GPVI ligand. Treating high-risk diabetic patients with GPVI ligands can reduce or prevent diabetes-associated disorders in these patients. These disorders include, but are not limited to, diabetic retinopathy, diabetic vasculopathy, atherosclerosis, ischemic stroke, and chronic renal failure. Treatment of diabetics with GPVI ligands can also reduce or inhibit microthrombus formation in these patients.

Also provided is a method for treating subjects suffering from platelet-mediated inflammatory disorders such as rheumatoid arthritis (RA) or other inflammatory arthritis disorders. Recent studies have shown that people who suffer from RA and other forms of inflammatory arthritis have increased levels of platelet microparticles in their joint fluids (Boilard et al., Science, 2010, 327:580-583). Platelet microparticles are pro-inflammatory and elicit an inflammatory response from surrounding cells (eg. synovial fibroblasts). For example, binding of collagen type IV to GPVI results in the release of IL-1 and IL-8.

Mechanistic studies in mice link the pro-inflammatory platelet state to GPVI activation. The absence of GPVI in knockout mouse models prevents the recruitment of proinflammatory cells and thus the recruitment and maturation of white blood cells in the synovium and extracellular matrix.

Joint inflammation leads to interaction of platelets with collagen in joint extracellular matrix, leading to amplification of inflammation via GPVI-mediated platelet activation of nearby cells and manifestation of RA/inflammatory arthritis conditions treatable by GPVI ligands. Accordingly, GPVI ligands can provide therapeutic use in the amelioration, reduction or prevention of inflammatory diseases such as RA or other inflammatory arthritides including, but not limited to, gout, psoriatic arthritis, reactive arthritis, viral or post-viral arthritis and spondylarthritis.

GPVI ligands can also be used to treat subjects suffering from scleroderma, or systemic sclerosis. Scleroderma appears to occur as an autoimmune response that produces swelling (inflammation) in the muscles and joints, associated with overproduction of collagen. Microvascular injury is one of the major pathogenic processes involved in systemic sclerosis or scleroderma. Interaction of the platelet type I and III collagen receptor (GPVI) with its respective ligand in the exposed subendothelial stroma as a result of ongoing microvascular injury in systemic sclerosis patients results in platelet activation and aggregation with the release of pro-inflammatory mediators, which contribute to vascular damage and inflammation (Chiang et al., Thrombosis, 2006, 117: 299-306). In systemic sclerosis, vascular lesions are characterized by an arteriolar-capillary perivasculitis with mononuclear cell infiltration that leads to arterial intimal proliferation and obliteration of arterioles and capillaries with attrition of endothelial cells and basal lamina. A recurring pattern of injury to the endothelial cells or basal lamina, or both, is characteristic of systemic sclerosis. Additionally, these events are driven by the overproduction and accumulation of collagen in body tissues, leading to extensive hardening and scarring of tissues throughout the body. Accordingly, the use of GPVI ligands can provide therapeutic relief from a disease such as scleroderma or systemic sclerosis which is associated with increased levels of collagen and platelet-mediated microvascular injury. A method of treating a subject suffering from scleroderma by administering a therapeutically effective amount of a GPVI ligand is provided herein.

The GPVI ligands disclosed herein can also be used to treat subjects diagnosed with cancer. Recent studies suggest that GPVI mediates tumor metastasis (see, e.g., Jain et al., J. Thromb. Haemostasis, 2009, 7:1713-1717). Using an in vivo experimental metastasis assay, Jain et al., show that GPVI knockout mice exhibited a significant decrease in tumor metastasis as compared to wildtype control mice. Accordingly, in one embodiment, a method for inhibiting, reducing or preventing metastasis in a subject diagnosed as having a primary cancerous tumor is provided, wherein the subject is administered a therapeutically effective amount of a GPVI ligand.

Methods, pharmaceutical compositions and uses of the GPVI nucleic acid ligands described herein are also provided as modulatable anti-platelet agents for use in disorders or treatment regimes requiring anti-platelet therapy. In certain embodiments, the treatment is a surgical intervention. The methods can include administering the GPVI nucleic acid ligand to a host in need thereof, wherein the host is suffering from, or at risk of suffering from, an occlusive thrombotic disease or disorder of the coronary, cerebral or peripheral vascular system.

In one embodiment, the GPVI ligand inhibits initiation of platelet activation. In other embodiments, the GPVI ligand inhibits platelet activation and the resultant platelet pro-inflammatory response. In other embodiments, the GPVI ligand inhibits platelet adhesion. In other embodiments, the GPVI ligand inhibits platelet aggregation. In yet a further embodiment, the GPVI ligand inhibits thrombin generation.

In one embodiment, the host has or is at risk of having an occlusive thrombotic disease of the coronary, cerebral and peripheral vascular systems. In certain other embodiments, the host is preparing to undergo or undergoing a surgical intervention, or has undergone a surgical intervention that puts the host at risk of an occlusive thrombotic event. In other embodiments, the host has received a vessel graft to enable hemodialysis, which is at risk of occluding due to interactions between the vessel and platelets.

In certain embodiments a method of treating or preventing formation of a vascular event, in particular a thrombotic or thromboembolitic event is provided including administering a GPVI nucleic acid ligand of the invention to a host in need thereof.

In one embodiment, the GPVI nucleic acid ligand is provided for extended periods of time. In this instance, a GPVI ligand modulator may only be used in emergency situations, for example, if treatment leads to hemorrhage, including intracranial or gastrointestinal hemorrhage. In another embodiment, the modulator is administered when emergency surgery is required for patients who have received GPVI nucleic acid ligand treatment. In another embodiment, the modulator is administered to control the concentration of the GPVI nucleic acid ligand and thereby the duration and intensity of treatment. In another embodiment, the GPVI nucleic acid ligand is provided as a platelet anesthetic during a cardiopulmonary bypass procedure. In another embodiment, the GPVI nucleic acid ligand is administered to provide a period of transition off of or on to oral anti-platelet medications, and the modulator is used to reverse the GPVI nucleic acid ligand once therapeutic levels of the oral anti-platelet agent are established.

H. PHARMACEUTICAL COMPOSITIONS

The GPVI nucleic acid ligands or GPVI ligand modulators taught herein can be formulated into pharmaceutical compositions that can include, but are not limited to, a pharmaceutically acceptable carrier, diluent or excipient. The precise nature of the composition will depend, at least in part, on the nature of the ligand and/or modulator, including any stabilizing modifications, and the route of administration. Compositions containing the modulator can be designed for administration to a host who has been given a GPVI nucleic acid ligand to allow modulation of the activity of the ligand, and thus regulate anti-platelet activity of the administered GPVI nucleic acid ligand.

The design and preparation of pharmaceutical or pharmacological compositions will be known to those of skill in the art in light of the present disclosure. Typically, such compositions can be prepared as injectables, either as liquid solutions or suspensions; solid forms suitable for solution in, or suspension in, liquid prior to injection; as tablets or other solids for oral administration; as time release capsules, as liquids for oral administration; as elixirs, syrups, suppositories, gels, or in any other form used in the art, including eye drops, creams, lotions, salves, inhalants and the like. The use of sterile formulations, such as saline-based washes, by surgeons, physicians or health care workers to treat a particular area in the operating field may also be particularly useful. Compositions can also be formulated for delivery via microdevice, microparticle or sponge.

Pharmaceutically useful compositions comprising a GPVI nucleic acid ligand or GPVI ligand modulator of the present invention can be formulated at least in part by the admixture of a pharmaceutically acceptable carrier. Examples of such carriers and methods of formulation can be found in Remington: The Science and Practice of Pharmacy, 20$^{th}$ edition (Lippincott Williams & Wilkins, 2000) and Ansel et al., Pharmaceutical Dosage Forms and Drug Delivery Systems, 6$^{th}$ Ed. (Media, Pa.: Williams & Wilkins, 1995).

Suitable pharmaceutical excipients include stabilizers, antioxidants, osmolality adjusting agents, buffers, and pH adjusting agents. Suitable additives include physiologically biocompatible buffers (e.g., tromethamine hydrochloride), additions of chelants (such as, for example, EDTA, DTPA or DTPA-bisamide) or calcium chelate complexes (as for example calcium DTPA, CaNaDTPA-bisamide), or, optionally, additions of calcium or sodium salts (for example, sodium chloride, calcium chloride, calcium ascorbate, calcium gluconate or calcium lactate). Pharmaceutical compositions of the invention can be packaged for use in liquid form, or can be lyophilized.

To form a pharmaceutically acceptable composition suitable for effective administration, such compositions will contain an effective amount of the nucleic acid ligand or modulator. Such compositions can contain admixtures of more than one compound. The compositions typically contain about 0.1% weight percent (wt %) to about 50 wt %, about 1 wt % to about 25 wt %, or about 5 wt % to about 20 wt % of the active agent (ligand or modulator).

Pharmaceutical compositions for parenteral injectable administration, including subcutaneous, intramuscular or intravenous injections and infusions are provided herein. For parenteral administration, aseptic suspensions and solutions are desired. Isotonic preparations that generally contain suitable preservatives are employed when intravenous administration is desired. The pharmaceutical compositions may be sterilized and/or contain adjuvants, such as preserving, stabilizing, wetting or emulsifying agents, solution promoters, salts for regulating the osmotic pressure and/or buffers. Liquid, particularly injectable compositions can, for example, be prepared by dissolving, dispersing, etc. The active compound is dissolved in or mixed with a pharmaceutically pure solvent such as, for example, water, buffered water, saline, 0.4% saline, 0.3% glycine, hyaluronic acid, aqueous dextrose, glycerol, ethanol, and the like, to thereby form the injectable solution or suspension. Additionally, solid forms suitable for dissolving in liquid prior to injection can be formulated.

To aid dissolution of an agent into an aqueous environment, a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. Nonionic detergents that could be included in the formulation as surfactants include, but are not limited to, lauromacrogol 400, polyoxyl 40 stearate, polyoxyethylene hydrogenated castor oil 10, 50 and 60, glycerol monostearate, polysorbate 20, 40, 60, 65 and 80, sucrose fatty acid ester, methyl cellulose, carboxymethyl cellulose and any of the pluronic detergents such as Pluronic F68 and/or Pluronic F127 (e.g., see Strappe et al. Eur. J. of Pharm. Biopharm., 2005, 61:126-133). Surfactants could be present in the formulation of a protein or derivative either alone or as a mixture in different ratios.

For oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation; starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms used in oral administration, the active drug component can be combined in suitably flavored suspending or dispersing agents such as the synthetic and natural gums, for example, tragacanth, acacia, methyl-cellulose and the like. Other dispersing agents that can be employed include glycerin and the like.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl ether propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. Active agents administered directly (e.g., alone) or in a liposomal formulation are described, for example, in U.S. Pat. No. 6,147,204.

The compounds of the present invention can also be coupled with soluble polymers as targetable drug carriers. Such polymers can include polyvinyl-pyrrolidone, pyran copolymer, polyhydroxypropylmethacryl-amide-phenol, polyhydroxy-ethylaspartamidephenol, or polyethyl-eneoxidepolylysine substituted with palmitoyl residues. Furthermore, the compounds of the present invention can be coupled (preferably via a covalent linkage) to a class of biodegradable polymers useful in achieving controlled release of a drug, for example, polyethylene glycol (PEG), polylactic acid, polyepsilon caprolactone, polyoxazolines, polyhydroxy butyric acid, polyorthoesters, polyacetals, polydihydro-pyrans, polycyanoacrylates and cross-linked or amphipathic block copolymers of hydrogels. Cholesterol and similar molecules can be linked to the nucleic acid ligands to increase and prolong bioavailability.

Lipophilic compounds and non-immunogenic high molecular weight compounds with which the modulators of the invention can be formulated for use in the present invention and can be prepared by any of the various techniques presently known in the art or subsequently developed. Typically, they are prepared from a phospholipid, for example, distearoyl phosphatidylcholine, and may include other materials such as neutral lipids, for example, cholesterol, and also surface modifiers such as positively charged (e.g., sterylamine or aminomannose or aminomannitol derivatives of cholesterol) or negatively charged (e.g., diacetyl phosphate, phosphatidyl glycerol) compounds. Multilamellar liposomes can be formed by the conventional technique, that is, by depositing a selected lipid on the inside wall of a suitable container or vessel by dissolving the lipid in an appropriate solvent, and then evaporating the solvent to leave a thin film on the inside of the vessel or by spray drying. An aqueous phase is then added to the vessel with a swirling or vortexing motion which results in the formation of MLVs. UVs can then be formed by homogenization, sonication or extrusion (through filters) of MLV's. In addition, UVs can be formed by detergent removal techniques. In certain embodiments of this invention, the complex comprises a liposome with a targeting nucleic acid ligand(s) associated with the surface of the liposome and an encapsulated therapeutic or diagnostic agent. Preformed liposomes can be modified to associate with the nucleic acid ligands. For example, a cationic liposome associates through electrostatic interactions with the nucleic acid. Alternatively, a nucleic acid attached to a lipophilic compound, such as cholesterol, can be added to preformed liposomes whereby the cholesterol becomes associated with the liposomal membrane. Alternatively, the nucleic acid can be associated with the liposome during the formulation of the liposome.

In another embodiment, a stent or medical device may be coated with a formulation comprising a GPVI ligand or GPVI ligand modulator according to methods known to skilled artisans.

Therapeutic kits are also envisioned. The kits comprises the reagents, active agents, and materials that may be required to practice the above methods. The kits will generally contain, in suitable container means, a pharmaceutically acceptable formulation of a GPVI ligand and/or a GPVI ligand modulator. The kit may have a single container means, and/or it may have distinct container means for each compound or each reaction mixture or step.

I. METHODS FOR ADMINISTRATION

Modes of administration of the GPVI ligands and/or GPVI ligand modulators of the present invention to a host include, but are not limited to, parenteral (by injection or gradual infusion over time), intravenous, intradermal, intra-articular, intra-synovial, intrathecal, intra-arterial, intracardiac, intramuscular, subcutaneous, intraorbital, intracapsular, intraspinal, intrasternal, topical, transdermal patch, via rectal, vaginal or urethral suppository, peritoneal, percutaneous, nasal spray, surgical implant, internal surgical paint, infusion pump or via catheter. In one embodiment, the agent and carrier are administered in a slow release formulation such as an implant, bolus, microparticle, microsphere, nanoparticle or nanosphere. In one embodiment, the GPVI nucleic acid ligand is delivered via subcutaneous injection or deposition including subcutaneous infusion (such as by osmotic pumps).

In one embodiment, the GPVI nucleic acid ligand is delivered via subcutaneous administration and the modulator is delivered by subcutaneous or intravenous administration.

The therapeutic compositions comprising ligands and modulators of the present invention may be administered intravenously, such as by injection of a unit dose. The term "unit dose" when used in reference to a therapeutic composition of the present invention refers to physically discrete units suitable as unitary dosage for the host, each unit containing a predetermined quantity of active material calculated to produce the desired therapeutic effect in association with the required diluent; i.e., carrier or vehicle.

Additionally, one approach for parenteral administration employs the implantation of a slow-release or sustained-released systems, which assures that a constant level of dosage is maintained.

Local administration, for example, to the interstitium of an affected joint, is also provided. Local administration can be achieved b injection, such as from a syringe or other article of manufacture containing a injection device such as a needle. The rate of administration from a syringe can be controlled by controlled pressure over desired period of time to distribute the contents of the syringe. In another example, local administration can be achieved by infusion, which can be facilitated by the use of a pump or other similar device.

Representative, non-limiting approaches for topical administration to a vascular tissue are also provided and include (1) coating or impregnating a blood vessel tissue with a gel comprising a nucleic acid ligand, for delivery in vivo, e.g., by implanting the coated or impregnated vessel in place of a damaged or diseased vessel tissue segment that was removed or by-passed; (2) delivery via a catheter to a vessel in which delivery is desired; (3) pumping a composition into a vessel that is to be implanted into a patient. Alternatively, the compounds can be introduced into cells by microinjection, or by liposome encapsulation.

Also provided is administration of the GPVI ligands to a subject by coating medical devices such as stents with pharmaceutical compositions containing the ligand. Methods for coating to allow appropriate release and administration of the ligand are known to those having ordinary skill in the art.

Optimum dosing regimens for the compositions described herein can be readily established by one skilled in the art and can vary with the modulator, the patient and the effect sought. The effective amount can vary according to a variety of factors such as the individual's condition, weight, sex, age and amount of nucleic acid ligand administered. Other factors include the mode of administration.

Generally, the compositions will be administered in dosages adjusted for body weight, e.g., dosages ranging from about 1 µg/kg body weight to about 100 mg/kg body weight. More typically, the dosages will range from about 0.1 mg/kg to about 20 mg/kg, and more typically from about 0.5 mg/kg to about 10 mg/kg, or about 1.0 to about 5.0 mg/kg, or about 1.0 mg/kg, about 2.0 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg or about 10.0 mg/kg. Typically, the dose initially provides a plasma concentration of drug about 0.002 µg/ml to about 2000 µg/ml of drug, more typically from about 2.0 µg/ml to about 400 µg/ml, and more typically from about 10 µg/ml to 200 µg/ml, or about 20 µg/ml to about 100 µg/ml drug, about 20 µg/ml, about 40 µg/ml, about 60 µg/ml, about 80 µg/ml, about 100 µg/ml, about 120 µg/ml, about 140 µg/ml, about 160 µg/ml, about 180 µg/ml, or about 200 µg/ml.

When administering a modulator to a host which has already been administered the ligand, the ratio of modulator to ligand can be adjusted based on the desired level of inhibition of the ligand. The modulator dose can be calculated based on correlation with the dose of ligand. In one embodiment, the weight-to-weight dose ratio of modulator to ligand is 1:1. In other embodiments, the ratio of modulator to ligand is greater than 1:1 such as 2:1 or about 2:1, 3:1 or about 3:1, 4:1 or about 4:1, 5:1 or about 5:1, 6:1 or about 6:1, 7:1 or about 7:1, 8:1 or about 8:1, 9:1 or about 9:1, 10:1 or about 10:1 or more. In other embodiments, the dose ratio of modulator to ligand is less than about 1:1 such as 0.9:1 or about 0.9:1, 0.8:1 or about 0.8:1, 0.7:1 or about 0.7:1, 0.6:1 or about 0.6:1, 0.5:1 or about 0.5:1, 0.45:1 or about 0.45:1, 0.4:1 or about 0.4:1, 0.35:1 or about 0.35:1, 0.3:1 or about 0.3:1, 0.25:1 or about 0.25:1, 0.2:1 or about 0.2:1, 0.15:1 or about 0.15:1, 0.1:1 or about 0.1:1 or less than 0.1:1 such as about 0.005:1 or less. In some embodiments, the ratio is between 0.5:1 and 0.1:1, or between 0.5:1 and 0.2:1, or between 0.5:1 and 0.3:1. In other embodiments, the ratio is between 1:1 and 5:1, or between 1:1 and 10:1, or between 1:1 and 20:1.

GPVI nucleic acid ligands of the present invention can be administered intravenously in a single daily dose, an every other day dose, or the total daily dosage can be administered in several divided doses. Ligand and/or modulator administration may be provide once per day (q.d.), twice per day (b.i.d.), three times per day (t.i.d.) or more often as needed. Thereafter, the modulator is provided by any suitable means to alter the effect of the nucleic acid ligand by administration of the modulator. Nucleic acid ligands of the present invention can be administered subcutaneously twice weekly, weekly, every two weeks or monthly. In some embodiments, the ligands or modulators are administered less often than once per day. For example, ligand administration may be carried out every other day, every three days, every four days, weekly, or monthly.

In one embodiment, co-administration or sequential administration of other agents can be desirable. For combination treatment with more than one active agent, where the active agents are in separate dosage formulations, the active agents can be administered concurrently, or they each can be administered at separately staggered times.

The compositions are administered in a manner compatible with the dosage formulation, and in a therapeutically effective amount. The quantity to be administered depends on the host to be treated, capacity of the host's system to utilize the active ingredient, and degree of therapeutic effect desired. Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are provided.

EXAMPLES

Example 1

Identification of Nucleic Acid Ligands to GPVI

The SELEX method was used to obtain ligands which bind the extracellular domain of GPVI as described and illustrated in FIG. 1 below.

A starting candidate DNA library was generated by heat annealing and snap-cooling 1 nmole of template DNA oligo and 1.5 nmoles of 5' DNA primer oligo. The sequence of the DNA template oligo for designing the candidate mixture are: 5'-TCTCGGATCC TCAGCGAGTC GTCTG($N_{40}$)CCGCA TCGTCCTCCC TA-3'(SEQ ID NO:4) ($N_{40}$ represents 40 contiguous nucleotides synthesized with equimolar quantities of A, T, G and C), the 5' primer oligo and 3' primer oligo are, respectively, 5'-GGGGGAATTC TAATACGACT CACTATAGGG AGGACGATGC GG-3' (SEQ ID NO:5) (T7 promoter sequence is underlined), and 5'-TCTCGGATCC TCAGCGAGTC GTCTG-3' (SEQ ID NO:6). The reaction was filled in with Exo⁻ Klenow, stopped by addition of EDTA to a final concentration of 2 mM, and extracted with PCI (phenol:chloroform:isoamyl alcohol (25:24:1)) and then chloroform:isoamyl alcohol (24:1). The extract was desalted, concentrated, and unincorporated nucleotides removed with an Amicon 10 spin column. The DNA template was utilized in a transcription reaction to generate a 2'-fluoropyrimidine starting library. In vitro transcription conditions were 40 mM Tris-HCl pH 8.0, 4% PEG-800, 12 mM MgCl₂, 1 mM spermidine, 0.002% Triton, 5 mM DTT, 1 mM rGTP, 1 mM rATP, 3 mM 2'F-CTP, 3 mM 2'F-UTP, 8 μg/mL inorganic pyrophosphatase, 0.5 μM DNA library, and Y639F mutant T7 polymerase. Transcriptions were incubated overnight at 37° C., DNase treated, chloroform:isoamyl alcohol (24:1) extracted twice, concentrated with an Amicon 10 spin column, and gel purified on a 12% denaturing PAGE gel. RNA was eluted out of the gel, and buffer exchanged and concentrated with TE (10 mM Tris pH 7.5, 0.1 mM EDTA) washes in an Amicon 10 spin column.

The GPVI selection started with a complex library of ~$10^{14}$ different 2'-fluoropyrimidine RNA sequences. The complex RNA pool was precleared against a biotin-PEG6-His$_6$ peptide, immobilized on magnetic streptavidin beads. The precleared RNA was bound to the purified recombinant extracellular domain of C-term His$_6$ tagged GPVI protein (SEQ ID NO:3). Purified histidine-tagged GPVI extracellular domain protein was obtained from R&D Systems (Minneapolis, Minn.), Catalog No. 3627-GP, and encompassed residues Gln21-Lys267.

Initial GPVI ligand selection was performed in binding buffer "E," and stringency was increased in later rounds to binding buffer "F." Binding buffer E consists of 20 mM HEPES pH 7.4, 50 mM NaCl, 2 mM CaCl$_2$, and 0.01% BSA. Binding buffer F consists of 20 mM HEPES pH 7.4, 150 mM NaCl, 2 mM CaCl$_2$, and 0.01% BSA. Protein-RNA complexes were partitioned over a 25 mm nitrocellulose disc with washing. The bound RNA was extracted off the nitrocellulose disc with incubation in PCI (25:24:1). Tris-EDTA buffer was added and the aqueous phase extracted, followed by a chloroform:isoamyl alcohol (24:1) extraction. The resultant bound RNA was ethanol precipitated. One quarter of the precipitated RNA was heat annealed to the 3' primer and reverse transcribed utilizing AMV RT. The entire RT reaction was utilized in PCR with 5' and 3' primers and standard PCR conditions to generate DNA template for the next round of RNA generation. Specific conditions for each round of selection are shown in FIG. 2. After Round 6, the selection was split into two arms, designated "E2" and "EF." The E2 selection had Rounds 1-8 performed in binding buffer E, and Rounds 9-10 performed in binding buffer F. The EF selection had Rounds 1-6 performed in binding buffer E, and Rounds 7-10 performed in binding buffer F.

Figure 3:
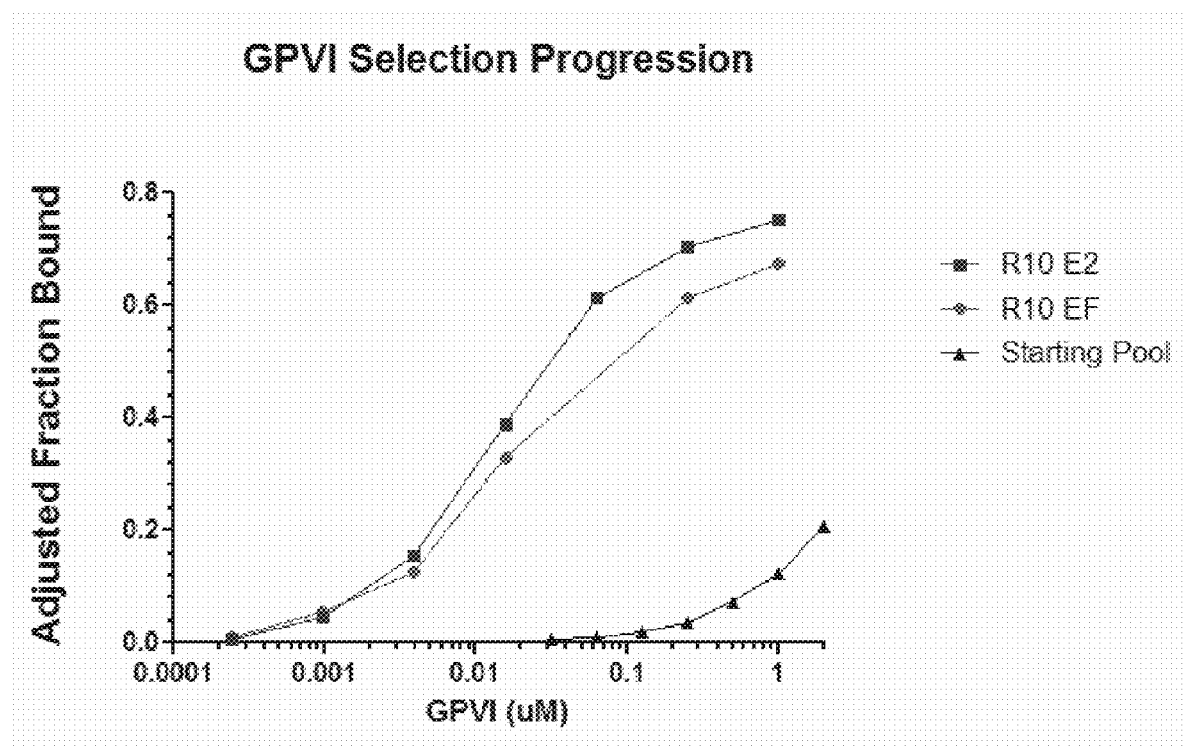
FIG. 3 shows the binding curves of trace $^{32}$P end-labeled libraries enriched in nucleic acid ligands to GPVI.

Enrichment of the ligand libraries for GPVI was monitored in direct binding studies utilizing radiolabeled ligand RNA from respective rounds of SELEX and soluble GPVI. Binding studies were performed with trace $P^{32}$ end-labeled RNA added to serial dilutions of GPVI in Binding Buffer F. To prepare radiolabeled RNAs for binding studies, one hundred picomoles of RNA was dephosphorylated with Bacterial Alkaline Phopshatase at 50° C. for 1 hour. The reaction was phenol:chloroform:isoamyl alcohol (25:24:1) extracted, chloroform:isoamyl:alcohol (24:1) extracted, and ethanol precipitated. Three pmoles of dephosphorylated RNA was end labeled with T4 Polynucleotide Kinase with supplied buffer, and 20 μCi of γ-$P^{32}$-ATP and subsequently cleaned with a Biorad MicroBio Spin P-30 spin column. End-labeled RNA was diluted to a final concentration of 2000 cpm/μL and heat denatured at 65° C. for 5 minutes. RNA and GPVI dilutions were equilibrated at 37° C. prior to use. RNA (5 μL) was added to varying concentrations of GPVI (15 μL) at 37° C. and incubated together for 5 to 15 minutes. The complexed RNA/GPVI protein mixture was then loaded over a Protean BA85 nitrocellulose membrane, overlayed on a Genescreen Plus Nylon membrane, in a 96 well vacuum manifold system with washing. The membranes were exposed to a phosphorimager screen, scanned, and quantitated with a Molecular Dynamics Storm 840 Phosphorimager. The fraction bound was calculated by dividing the counts on the nitrocellulose by the total counts and adjusting for the background. Results for binding of enriched ligand libraries from round 10 E2 and round 10 EF of the SELEX as compared to the GPVI-naïve starting ligand library are shown in FIG. 3.

Example 2

Sequencing and Identification of a Structural Family of GPVI Nucleic Acid Ligands The final PCR products representing anti-GPVI enriched ligand libraries from Round 10 of the SELEX experiments described in Example 1 were digested with EcoR1 and BamH1, cleaned with a purification kit, and directionally cloned into linearized pUC19 vector. Bacterial colonies were streaked for single clones and 5 mL overnight cultures were inoculated from single colonies. Plasmid DNA was prepared from single colonies using Qiagen Plasmid Mini Prep kits. Forty plasmids from each SELEX experiment were sequenced utilizing a vector primer. DNA sequences derived from the random region are shown in FIG. 4. Analysis of these sequences identified 6 unique sequences, which are labeled as "A" through "F" in FIG. 4. The corresponding unique DNA sequences of the full-length ligand clones are shown in Table 1 below, whereas sequences representing the random region are provided in Table 2.

TABLE 1

Full-Length DNA Ligands Identified via SELEX

| Name | Sequence | Group | SEQ ID NO. |
|---|---|---|---|
| EF-1 | GGGAGGACGATGCGGCAATCGAAGCTGCATCCAGCGTAAG CCTTCCAGGGATCGTCAGACGACTCGCTGAGGATCCGAGA | A | 22 |
| EF-2 | GGGAGGACGATGCGGTGCCAAAACACCCGTCTTGCATAAG CCTCCTACGGCAACTCAGACGACTCGCTGAGGATCCGAGA | B | 23 |
| EF-3 | GGGAGGACGATGCGGATCACACCGCGTCTTGCGTAAGCCT CCTACTAACGGATCGCAGACGACTCGCTGAGGATCCGAGA | C | 24 |
| E2-6 | GGGAGGACGATGCGGATAGACCGCGTCTGGCATAAGCCTC CAAACACTCTGATCCCAGACGACTCGCTGAGGATCCGAGA | D | 25 |
| EF-22 | GGGAGGACGATGCGGATTCAACCCGCCTCTGGCATAAGCC TACCCATCGTGATTGTCAGACGACTCGCTGAGGATCCGAGA | E | 26 |

TABLE 1-continued

Full-Length DNA Ligands Identified via SELEX

| Name | Sequence | Group | SEQ ID NO. |
|---|---|---|---|
| EF-31 | GGGAGGACGATGCGGTCTAAGCTGCGTCTGGCATAAGCCTCACCTACTCGATACTCAGACGACTCGCTGAGGATCCGAGA | F | 27 |

TABLE 2

Random Regions of A-F

| Name | Sequence | Group | SEQ ID NO. |
|---|---|---|---|
| EF-1 | CAATCGAAGCTGCATCCAGCGTAAGCCTTCCAGGGATCGT | A | 11 |
| EF-2 | TGCCAAAACACCCGTCTTGCATAAGCCTCCTACGGCAACT | B | 14 |
| EF-3 | ATCACACCGCGTCTTGCGTAAGCCTCCTACTAACGGATCG | C | 7 |
| E2-6 | ATAGACCGCGTCTGGCATAAGCCTCCAAACACTCTGATCC | D | 15 |
| EF-22 | ATTCAACCCGCCTCTGGCATAAGCCTACCCATCGTGATTGT | E | 9 |
| EF-31 | TCTAAGCTGCGTCTGGCATAAGCCTCACCTACTCGATACT | F | 12 |

Representation of these unique ligands as full-length RNA is shown in Table 3, and as RNA sequences indicating the sites of incorporation of the 2'-fluorpyrimidine nucleotides used in the SELEX experiment in Table 4 (f indicates a 2'-fluorpyrimidine modification and r indicates a non-modified ribonucleotide). Full-length refers to sequences resulting from the SELEX process, comprising sequences derived from both the random portion of the ligand library used in the SELEX process as well as sequences from the fixed-sequence portions flanking the random region.

TABLE 3

Full-Length RNA Sequences

| Name | RNA Sequence | Group | SEQ ID NO. |
|---|---|---|---|
| EF-1-RNA | GGGAGGACGAUGCGGCAAUCGAAGCUGCAUCCAGCGUAAGCCUUCCAGGGAUCGUCAGACGACUCGCUGAGGAUCCGAGA | A | 28 |
| EF-2-RNA | GGGAGGACGAUGCGGUGCCAAAACACCCGUCUUGCAUAAGCCUCCUACGGCAACUCAGACGACUCGCUGAGGAUCCGAGA | B | 29 |
| EF-3-RNA | GGGAGGACGAUGCGGAUCACACCGCGUCUUGCGUAAGCCUCCUACUAACGGAUCGCAGACGACUCGCUGAGGAUCCGAGA | C | 30 |
| E2-6-RNA | GGGAGGACGAUGCGGAUAGACCGCGUCUGGCAUAAGCCUCCAAACACUCUGAUCCCAGACGACUCGCUGAGGAUCCGAGA | D | 31 |
| EF-22-RNA | GGGAGGACGAUGCGGAUUCAACCCGCCUCUGGCAUAAGCCUACCCAUCGUGAUUGUCAGACGACUCGCUGAGGAUCCGAGA | E | 32 |
| EF-31-RNA | GGGAGGACGAUGCGGUCUAAGCUGCGUCUGGCAUAAGCCUCACCUACUCGAUACUCAGACGACUCGCUGAGGAUCCGAGA | F | 33 |

TABLE 4

Full-Length RNA Sequences with Modifications

| Name | Modified Sequence* | Group | SEQ ID NO. |
|---|---|---|---|
| EF-1-modified | rGrGrGrArGrGrAfCrGrAfUrGfCrGrGfCrArAfUfCrGrArArGfCfUrGfCrAfUfCfCrArGfCrGfUrArArGfCfCfUfUfCfCrArGrGrGr | A | 28 |

TABLE 4-continued

Full-Length RNA Sequences with Modifications

| Name | Modified Sequence* | Group | SEQ ID NO. |
|---|---|---|---|
| | AfUfCrGfUfCrArGrAfCrGrAfCfUfCrGfCfUrGrArGrGrAfUfCf CrGrArGrA | | |
| EF-2-modified | rGrGrGrArGrGrAfCrGrAfUrGfCrGrGrUrGfCfCrArArArAfCrA fCfCfCrGfUfCfUfUrGfCrAfUrArArGfCfCfUfCfCfUrAfCrGrGf CrArAfCfUfCrArGrAfCrGrAfCfUfCrGfCfUrGrArGrGrAfUfCf CrGrArGrA | B | 29 |
| EF-3-modified | rGrGrGrArGrGrAfCrGrAfUrGfCrGrGrAfUfCrAfCrAfCfCrGfCr GfUfCfUfUrGfCrGfUrArArGfCfCfUfCfCfUrAfCfUrArAfCrGr GrAfUfCrGfCrArGrAfCrGrAfCfUfCrGfCfUrGrArGrGrAfUfCf CrGrArGrA | C | 30 |
| E2-6-modified | rGrGrGrArGrGrAfCrGrAfUrGfCrGrGrAfUrArGrAfCfCrGfCrG fUfCfUrGrGfCrAfUrArArGfCfCfUfCfCrArArAfCrAfCfUfCfUr GrAfUfCfCfCrArGrAfCrGrAfCfUfCrGfCfUrGrArGrGrAfUfCf CrGrArGrA | D | 31 |
| EF-22-modified | rGrGrGrArGrGrAfCrGrAfUrGfCrGrGrAfUfUfCrArAfCfCfCrGf CfCfUfCfUrGrGfCrAfUrArArGfCfCfUrAfCfCfCrAfUfCrGfUr GrAfUfUrGfUfCrArGrAfCrGrAfCfUfCrGfCfUrGrArGrGrAfUf CfCrGrArGrA | E | 32 |
| EF-31-modified | rGrGrGrArGrGrAfCrGrAfUrGfCrGrGfUfCfUrArArGfCfUrGfC rGfUfCfUrGrGfCrAfUrArArGfCfCfUfCrAfCfCfUrAfCfUfCrGr AfUrAfCfUfCrArGrAfCrGrAfCfUfCrGfCfUrGrArGrGrAfUfCf CrGrArGrA | F | 33 |

*SEQ ID NOs refer to the unmodified versions of the ligands described in the column titled, "Modified Sequence"
rG = 2'Ribo G;
rA = 2'Ribo A;
fC = 2'-Fluoro C;
fU = 2'-Fluoro U Further examination of these six sequences identified a conserved primary sequence shared by each of the clones consisting of (A/G)UAA flanked on each side by the sequence GC (eg., GC(A/G)UAAGC), indicating these six unique sequences were members of a related family.

Screening of sequences for potential secondary structure was conducted utilizing the mfold server (mfold.bioinfo.rpi.edu). A description of these methods is found on the server site as well as in M. Zuker (2003) "Mfold web server for nucleic acid folding and hybridization prediction." *Nucleic Acids Res.* 31 (13), 3406-15 and D. H. Mathews, et al. (1999) "Expanded Sequence Dependence of Thermodynamic Parameters Improves Prediction of RNA Secondary Structure" *J. Mol. Biol.* 288, 911-940. Subsequently, comparative sequence analysis of the unique sequences was used to align the sequences based upon conserved consensus secondary structural elements to arrive at the predicted secondary structure of the anti-GPVI ligands (see FIG. 5 and FIG. 8).

The anti-GPVI ligands shared a consensus secondary structure consisting of 3 stems (S1-S3) and 4 loops (L1-L4), with the conserved (A/G)UAA sequence within Loop 4, and the flanking GC sequences forming a paired region to comprise Stem 3. Solving the consensus secondary structure of the anti-GPVI ligand family identified additional conserved structural elements, as depicted in FIG. 5. The size and sequence of Loop 1 was conserved, with Loop 1 consisting of 3 nucleotides of the sequence GAC. The size and sequence of Loop 3 was also conserved, with Loop 3 consisting of 2 nucleotides, most often consisting of the sequence UU, or UG, although CA was present in one member of the family. Stem 1 consisted of 4-5 basepairs, whereas the length of Stem 2 was longer, typically consisting of 7-8 basepairs. Loop 2 was more variable in size, ranging from 4-7 nucleotides in length.

The affinity of each of the anti-GPVI ligands for GPVI was determined by direct binding studies using radiolabeled trace ligand RNA and soluble GPVI, per the binding methodology described above in Example 1. The affinity of the anti-GPVI ligands for GPVI was high, and ranged from a $K_d$ of ~11 nM to ~50 nM, with the rank potency of the affinity for GPVI of EF-2≈EF-3≈E2-6≈EF-22≈EF-31>>EF-1. Interestingly, ligand EF-1, which contains the sequence CA in loop 3, exhibited the lowest affinity for GPVI, consistent with the importance of a loop 3 sequence of UU or UG for high affinity GPVI binding.

Example 3

Truncation and Mutational Probing of Anti-GPVI Ligand Structure

The conserved secondary structure of the anti-GPVI ligands presented in FIG. 5 allows reliable predictions as to the minimal sequence required to form this structure and bind with high affinity to GPVI. Initial experiments were aimed at defining the 5' and 3' boundary sequence requirements for maintaining an ligand having the desired structure and function.

Figure 6:
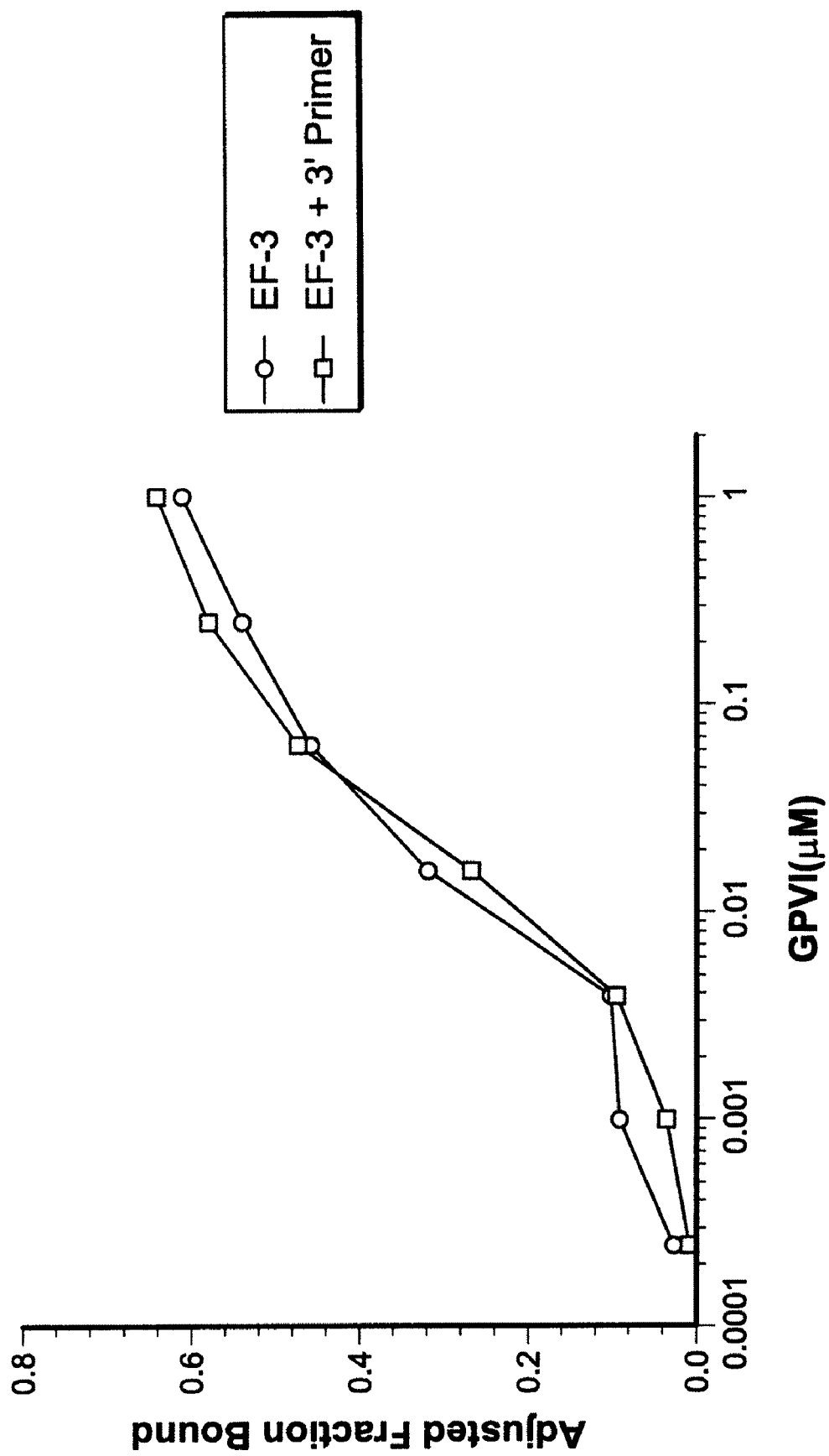
FIG. 6 is a graph of the binding of the EF-3 GPVI ligand to GPVI, with or without annealing of a 3' primer to EF-3 to mask the 3' fixed region of EF-3 during protein interaction.

The consensus secondary structure presented in FIG. 5 indicates that regions of the ligand derived from the 3' fixed region of the ligand library are likely dispensable for GPVI binding. The importance of the 3' fixed region derived sequence on interaction with GPVI was tested by heat annealing the complementary DNA 3' primer onto the $P^{32}$ end-labeled RNA identified above, equilibrating, and performing binding studies (as described above in Example 1). The results are shown in FIG. 6. The binding of the ligand with and without the annealed primer was comparable, suggesting this region is dispensable for binding to the GPVI protein, as predicted by the consensus structure presented in FIG. 5.

Truncated compounds for several of the anti-GPVI ligands containing the 5' and 3' required sequence boundaries for Stem 1 as predicted by the consensus structure presented in FIG. 5 were prepared (Table 5), and their affinity for GPVI determined. The "RB ID" is a unique identifier that refers to the ligand having the sequence with specific modifications noted in the column titled, "Modified Sequence." The "SEQ ID NO:" refers to the corresponding nucleic acid sequence (DNA and/or RNA) without modifications.

TABLE 5

GPVI Ligand Truncations and Binding Activity

| Name | SEQ ID NO: | RB ID | Binding | Modified Sequence |
|---|---|---|---|---|
| EF-1 | 28 | RB424 | + | rGrGrGrArGrGrAfCrGrAfUrGfCrGrGfCrArAfUfCrGrArArGfCfUrGfCrAfUfCfCrArGfCrGfUrArArGfCfCfUfUfCfCrArGrGrGrAfUfCrGfUfCrArGrAfCrGrAfCfUfCrGfCfUrGrArGrGrAfUfCfCrGrArGrA |
| EF-1 T1 | 34 | RB426 | + | rGrGrGrArGrGrAfCrGrAfUrGfCrGrGfCrArAfUfCrGrArArGfCfUrGfCrAfUfCfCrArGfCrGfUrArArGfCfCfUfUfCfC |
| EF-2 | 29 | RB427 | +++ | rGrGrGrArGrGrAfCrGrAfUrGfCrGrGfUrGfCfCrArArArAfCrAfCfCfCrGfUfCfUfUrGfCrAfUrArArGfCfCfUfCfUrAfCrGrGfCrArAfCfUfCrArGfAfCrGrAfCfUfCrGfCfUrGrArGrGrAfUfCfCrGrArGrA |
| EF-2 T1 | 35 | NA | +++ | rGrGrGrArGrGrAfCrGrAfUrGfCrGrGfUrGfCfCrArArArAfCrAfCfCfCrGfUfCfUfUrGfCrAfUrArArGfCfCfUfCfUrAfCrGrGfCrArAfCfU |
| EF-2 T2 | 36 | RB428 | +++ | rGrGrGrArGrGrAfCrGrAfUrGfCrGrGfUrGfCfCrArArArAfCrAfCfCfCrGfUfCfUfrGfCrAfUrArArGfCfCfCfUfCfCfU |
| EF-2-T2 mut3 | 37 | NA | ND | rGrGrGrArGrGrAfCrGrAfUrGfCrGrGfUrGfCfCrArArArAfCrAfCfCfCrGfUfC<u>rArAr</u>GfCrAfUrArArGfCfCfUfCfCfU |
| EF-2-T2 mut4 | 38 | NA | ND | rGrGrGrArGrGrAfCrGrAfUrGfCrGrGfUrGfCfCrArArArAfCrAfCfCfCrGfUfCfUfUrGfCrAfU<u>fUfU</u>rGfCfCfUfCfCfU |
| EF-2-T2 mut5 | 39 | NA | ND | rGrGrGrArGrGrAfCrGrAfUrGfCrGrGfUrGfCfCrArArArAfCrAfCfCfCrGfUfCfUfUrGfCrAfU<u>rGrGr</u>GfCfCfUfCfCfU |
| EF-3 | 30 | RB429 | +++ | rGrGrGrArGrGrAfCrGrAfUrGfCrGrGrAfUfCrAfCrAfCfCrGfCrGfUfCfUfUrGfCrGfUrArArGfCfCfUfCfCfUrAfCfUrArAfCrGrGrAfUfCrGfCrArGrAfCrGrAfCfUfCrGfCfUrGrArGrGrAfUfCfCrGrArGrA |
| EF-3 T2 | 40 | RB430 | +++ | rGrGrGrArGrGrAfCrGrAfUrGfCrGrGrAfUfCrAfCrAfCfCrGfCrGfUfCfUfUrGfCrGfUrArArGfCfCfUfCfCfU |
| EF-3 T3 | 41 | RB445 | + | rGrGrGrArGrGrAfCrGfUrGfCrGrGrAfUfCrAfCrAfCfCrGfCrGfCfUfUrGfCrGfUrArArGfCfCfUfCfCfC |
| EF-3 T4 | 42 | RB446 | +++ | rGrGrGrArGrGrAfCrGrGfCrGrGrAfUfCrAfCrAfCfCrGfCfCfUfUrGfCrGfUrArArGfCfCfUfCfCfC |
| EF-3 T5 | 43 | RB447 | +++ | rGrGrGrArGrGrAfCrGrGfCrGrAfUfCrAfCrAfCfCrGfCfCfUfUrGfCrGfUrArArGfCfCfUfCfCfC |
| EF-3 T2 mut3 | 44 | NA | ND | rGrGrGrArGrGrAfCrGrAfUrGfCrGrGrAfUfCrAfCrAfCfCrGfCrGfUfC<u>rArAr</u>GfCrGfUrArArGfCfCfUfCfCfU |
| EF-3 T2 mut4 | 45 | NA | ND | rGrGrGrArGrGrAfCrGrAfUrGfCrGrGrAfUfCrAfCrAfCfCrGfCrGfUfCfUfUrGfCrGf<u>UfUfU</u>rGfCfCfUfCfCfU |
| EF-3 T2 mut5 | 46 | NA | ND | rGrGrGrArGrGrAfCrGrAfUrGfCrGrGrAfUfCrAfCrAfCfCrGfCrGfUfCfUfUrGfCrGf<u>UrGrGr</u>GfCfCfUfCfCfU |
| EF-3 T2 mut6 | 47 | NA | ++ | rGrGrGrArGrGrAfCrGrAfUrGfCrGrGrAfUfCrAfCrAfCfCrGfCrGfUfCfU<u>rAr</u>GfCrGfUrArArGfCfCfUfCfCfU |
| EF-3 T2 mut7 | 48 | NA | ND | rGrGrGrArGrGrAfCrGrAfUrGfCrGrGrAfUfCrAfCrAfCfCrGfCrGfUfC<u>rAf</u>UrGfCrGfUrArArGfCfCfUfCfCfU |

TABLE 5-continued

GPVI Ligand Truncations and Binding Activity

| Name | SEQ ID NO:RB ID | Bind-ing | Modified Sequence |
|---|---|---|---|
| EF-3 T5 mut8 | 49 NA | +++ | rGrGrGrArGrGrAfCrGrGfCrGrAfUfCrAfCrAfCrGfCfCfU<u>rGr</u>GfCrGfUrArArGfCfCfUfCfCfC |
| EF-3 T5 mut9 | 50 NA | +++ | rGrGrGrArGrGrAfCrGrGfCrGrAfUfCrAfCrAfCrGfCfCfUfUrGfC<u>rAf</u>UrArArGfCfCfUfCfCfC |
| EF-3 T5 mut10 | 51 NA | +++ | rGrGrGrArGrGrAfCrGrGfCrGrAfUfCrAfCrAfCrGfCfCfU<u>rGr</u>GfC<u>rAf</u>UrArArGfCfCfUfCfCfC |
| E2-6 | 31 RB431 | +++ | rGrGrGrArGrGrAfCrGrAfUrGfCrGrGrAfUrArGrAfCfCrGfCrGfUfCfUrGrGfCrAfUrArArGfCfCfUfCfCrArArAfCrAfCfUfCfUrGrAfUfCfCfCrArGrAfCrGrAfCfUfCrGfCfUrGrArGrGrAfUfCfCrGrAr GrA |
| E2-6 T1 | 52 RB432 | +++ | rGrGrGrArGrGrAfCrGrAfUrGfCrGrGrAfUrArGrAfCfCrGfCrGfUfCfUrGrGfCrAfUrArArGfCfCfUfCfC |
| EF-22 | 32 RB433 | +++ | rGrGrGrArGrGrAfCrGrAfUrGfCrGrGrAfUfUfCrArAfCfCfCrGfCfCfUfCfUrGrGfCrAfUrArArGfCfCfUrAfCfCfCrAfUfCrGfUrGrAfUfUrGfUfCrArGrAfCrGrAfCfUfCrGfCfUrGrArGrGrAfUfCfCrGrAr GrA |
| EF-22 T1 | 53 RB434 | +++ | rGrGrGrArGrGrAfCrGrAfUrGfCrGrGrAfUfUfCrArAfCfCfCrGfCfCfUfCfUrGrGfCrAfUrArArGfCfCfUrAfCfCfC |
| EF-31 | 33 RB435 | +++ | rGrGrGrArGrGrAfCrGrAfUrGfCrGrGrGfUfCfUrArArGfCfUrGfCrGfUfCfUrGrGfCrAfUrArArGfCfCfUfCrAfCfCfUrAfCfUfCrGrAfUrAfCfUfCrArGrAfCrGrAfCfUfCrGfCfUrGrArGrGrAfUfCfCrGrAr GrA |
| EF-31 T1 | 54 RB436 | +++ | rGrGrGrArGrGrAfCrGrAfUrGfCrGrGrGfUfCfUrArArGfCfUrGfCrGfUfCfUrGrGfCrAfUrArArGfCfCfUfCrAfCfCfUrAfCfU |
| EF-31 T2 | 55 RB439 | +++ | rGrGrGrArGrGrAfCrGrAfUrGfCrGrGrGfUfCfUrArArGfCfUrGfCrGfUfCfUrGrGfCrAfUrArArGfCfCfUfCrAfCfC |
| EF-31 T3 | 56 RB440 | +++ | rGrGrGrArGrGrAfCrGrAfUrGfCrGrGrGfUfCfUrArArGfCfUrGfCrGfUfCfUrGrGfCrAfUrArArGfCfCfUfCfCfC |
| EF-31 T4 | 57 RB441 | + | rGrGrGrArGrGrAfCrGfUrGfCrGrGfUfCfUrArArGfCfUrGfCrGfCfUrGrGfCrAfUrArArGfCfCfUfCfC |
| EF-31 T5 | 58 RB442 | +++ | rGrGrGrArGrGrAfCrGrGfCrGrGfUfCfUrArArGfCfUrGfCfCfUrGrGfCrAfUrArArGfCfCfUfCfCfC |
| EF-31 T6 | 59 RB443 | +++ | rGrGrGrArGrGrAfCrGrGfCrGfUfCfUrArArGfCrGfCfCfUrGrGfCrAfUrArArGfCfCfUfCfCfC |
| EF-31 T7 | 60 RB444 | +++ | rGrGrGrArGrGrAfCrGrGfCrGfCfUrArAfCrGfCfCfUrGrGfCrAfUrArArGfCfCfUfCfCfC |
| EF-31 T8 | 61 NA | + | rGrGrGrArGrGrAfCrGrGfCfCfUrArArGfCfCfUrGrGfCrAfUrArArGfCfCfUfCfCfC |

All RNAs were in vitro transcribed from either PCR generated or Klenow generated templates?
SEQ ID NOs refer to the unmodified versions of the ligands described in the column titled, "Modified Sequence"
rG = 2'Ribo G;
rA = 2'Ribo A;
fC = 2'-Fluoro C;
fU = 2'-Fluoro U
Underlined nucleotides note introduced changes
++++ $K_d$ less than 10 nM
+++ $K_d$ 10 nM-24 nM
++ $K_d$ 25 nM-40 nM
+ $K_d$ > 40 nM
ND Binding not detected
NA Not Assigned Binding data for several representative truncates are shown in FIG. 7. Consistent with the consensus 5' and 3' boundaries predicted by the secondary structure defined in FIG. 5, EF-1 T1, EF2 T2, EF-3 T2, E2-6 T1, EF-22 T1, and EF-31 T2 bound GPVI with a $K_d$ equivalent to the respective full-length parent ligand, confirming the predicted boundaries of the 5' and 3' end are sufficient to form Stem 1 and functional anti-GPVI ligands (See Table 5).

The consensus structure presented in FIG. 5 suggests that Stem 2 may contain more basepairs than are required to form a stable stem structure. Furthermore, the conservation of the size and sequence of Loop 1, which is derived from the 5' fixed region of the starting ligand library, combined with the size of Stem 2 and lack of conservation in the length or sequence of Loop 2, suggest that Stem 2 and Loop 2 may have, in part, a spacing function to properly present Loop 1. Based on these insights, it may be possible to reduce the size of Stem 2 while retaining high affinity binding to GPVI. Therefore, additional truncates were prepared to determine the minimal size of Stem 2 required for high affinity binding to GPVI (See FIGS. 8A, B, C for secondary structure representations and Table 5 for sequence identifiers). EF-3 T4 and T5, and EF-31 T5, T6 and T7 bound GPVI with a $K_d$ equivalent to the respective full-length parent ligand, confirming that a Stem 2 as short as 4 basepairs in length is sufficient for high affinity binding to GPVI. These results are entirely consistent with a role for Stem 2 and Loop 2 in properly presenting the GAC sequence of Loop 1. Additionally, truncates EF-3 T3 and EF-31 T4, which deleted the A-U basepair at the $2^{nd}$ position from the base of Stem 2, both exhibited reduced binding as compared to the respective full-length parent ligand. Examination of the Stem 2 composition for these truncates as compared to the Stem 2 composition for the truncates listed above, which did not exhibit reduced GPVI affinity, revealed that truncates EF-3 T3 and EF-31 T4 uniquely positioned a U-G at this position within Stem 2, as opposed to a G-C basepair or the A-U basepair present in the parental sequences. This indicates that a purine-pyrimidine pair may be required at the $2^{nd}$ basepair from the base of Stem 2 for high affinity GPVI binding, a feature conserved in the consensus secondary structure of the anti-GPVI ligands presented in FIG. 5.

The consensus secondary structure of the anti-GPVI ligands presented in FIG. 5 shows primary sequence conservation within Loops 1, 3 and 4, and no conservation in the size or sequence content of Loop 2. Mutations and substitutions were constructed within these loops to evaluate the functional importance of the observed conservation, or lack thereof, in these loop sequences (see Table 5 above; the underlined portions indicate mutated residues).

The conserved UU found within Loop 3 of EF-2 T2 or EF-3 T2 was mutated to AA (EF-2 T2mut3 and EF-3 T2mut3, See FIG. 9 for secondary structure representations), resulting in complete loss of measurable binding to GPVI, consistent with the importance of a UU or UG sequence for Loop 3 as predicted by the consensus secondary structure presented in FIG. 5. The conserved UU located within Loop 3 in EF-3 T2 was also mutated to UA (EF-3 T2mut6) and AU (EF-3 T2mut7). Consistent with the consensus structure of the anti-GPVI ligands, mutation of the first U of Loop 3 to A resulted in loss of measurable binding to GPVI, while mutation of the second U of Loop 3 to A resulted in a slight decrease in affinity for GPVI. Thus, a Loop 3 sequence of UA, like UU or UG, supports high affinity binding of anti-GPVI ligands to GPVI, and is consistent with the observed conservation of Loop 3 as 5'-YD-3', where Y represents a pyrimidine and a U is highly favored as the pyrimidine in Loop 3, and D represents U or G or A (not C).

The conserved GUAA of EF-3 T2 and AUAA of EF-2 T2 within Loop 4 were mutated to GUUU (EF-3 T2mut4) and AUUU (EF-2 T2mut4) respectively, as well as to GUGG (EF-3 T2mut5) and AUGG (EF-2 T2mut5) (See FIG. 9 for secondary structure representations). Both sets of substitutions resulted in complete loss of measurable GPVI binding, consistent with the importance of the Loop 4 sequence of AUAA or GUAA to GPVI binding as predicted by the consensus secondary structure presented in FIG. 5. To further verify the importance of the conserved sequences within Loops 3 and 4, Loop 3 of EF-3 T2 was converted to UG (EF-3 T2mut8), as found in the EF-22, E2-6 and EF-31 sequences, which resulted in no significant change in affinity for GPVI, consistent with the conserved structure of the anti-GPVI ligands presented in FIG. 5. Additionally, Loop 4 of EF-3 T2 was converted to AUAA (EF-3 T2 mut9) as found in EF-2, EF-22, E2-6 and EF-31, which resulted in no significant change in affinity for GPVI, consistent with the conserved structure of the anti-GPVI ligands presented in FIG. 5. Finally, simultaneous conversion of EF-3 T2 Loop 3 to UG and Loop 4 to AUAA (EF-3 T2mut10), as found in EF-22, E2-6 and EF-31, resulted in no significant change in affinity for GPVI, consistent with the conserved structure of the anti-GPVI ligands presented in FIG. 5.

Synthetic anti-GPVI ligands with single-point mutations in Loop 1 (RB470-RB472, see Table 6 below) were produced, converting the Loop 1 sequence to CAC, GUC, and GAG respectively. Each substitution resulted in complete loss of measurable GPVI binding, consistent with the importance of the Loop 1 sequence of GAC to GPVI binding as predicted by the consensus secondary structure presented in FIG. 5.

Loop 2 exhibited no apparent conservation in length or sequence composition, but rather, may have served a role as a spacer in the isolated ligands, to enable presentation within Loop 1 of the GAC sequence derived from the 5' fixed sequence of the ligand library used in SELEX. This would predict that a nucleotide composition of Loop 2 is not required for high affinity binding to GPVI. Consistent with this prediction, substitution of Loop 2 of EF-31 T7 (RB466) with a hexaethylene glycol spacer (See FIG. 13A-B) resulted in no loss of affinity for GPVI, as compared to the parent ligand (RB448). Binding data for RB 466 are presented in FIG. 10.

Example 4

Further Truncation and Optimization of the 2' Sugar Modification and Phosphodiester Backbone of Anti-GPVI Ligand Ligands isolated from 2'-fluorpyrimidine/2'-hydroxypurine libraries exhibit sufficient nuclease stability for in vitro screening. However, the high 2'-hydroxyl content make them unsuitable for drug development candidates due to the fact that these positions can be very sensitive to nuclease degradation in vivo, limiting the maximal concentration that can be achieved post parenteral administration as well as their circulating half-life. Therefore, we sought to optimize the anti-GPVI ligands by further stabilization of the backbone by substitution of 2'-O-methyl nucleotides for 2'-hydroxyl nucleotides, or by substitution of 2'-deoxy nucleotides for 2'-hydroxyl nucleotides, with modification of the ligand backbone by phosphorothioate substitution as needed to preserve affinity for GPVI while enhancing nuclease stability. Additional substitutions of 2'-O-methyl nucleotides for 2'-fluoro nucleotides were also made to further improve stability, reduce cost of manufacturing, and reduce the level of potential impurities that can arise during heating of 2'-fluorouridine-containing oligonucleotides during manufacturing processes. Finally, "capping" of the 5' and 3' ends, which prevents exonuclease degradation of oligonucleotides, was also attempted to further enhance in vivo stability. Conservation of the minimal required sequence amongst the anti-GPVI ligands was quite high, and in general, their affinities for GPVI were similar. Ligand EF-31 T7 represented a minimal anti-GPVI ligand with high GPVI affinity and a reduced length of Loop 2, and was therefore chosen as a parent molecule for further optimization of the anti-GPVI ligands for nuclease stability and GPVI binding.

Capping of the 3' end of EF-31 T7 was accomplished by synthesis of the ligand from a CPG-support loaded with inverted deoxythymidine, to create a 3'-3' linkage (RB448) at the 3' end of the ligand. This modification was well tolerated, and was therefore used in all synthetically produced modifications to this ligand. RB448 (SEQ ID NO:62) has the sequence:

rGrGrGrArGrGrAfCrGrGfCrGfCfUrArAfCrGfCfCfUrGrGfCrA fUrArArGfCfCfUfCfCfCiT, wherein "r" represents a ribonucleic acid, "f" represents a 2'-fluoro nucleotide, and "iT" represents the inverted deoxythymidine.

Initial substitutions of 2'Omethyl nucleotides for 2'hydroxyl and 2'fluoro nucleotides were synthesized within Stems 1, 2 and 3, and tested for binding to GPVI in direct binding assays as described in Example 1. Results of the binding assays are presented in Table 6 below. Substitution of most (RB452) or all (RB453) of the 2'-hydroxyls with 2'-O-methyls within Stem 1 was well tolerated, with an all 2'-O-methyl composition of Stem 1 resulting in an increase in affinity for GPVI as compared to the parent compound (RB448), consistent with the conserved secondary structure of the anti-GPVI ligands. Substitution of the 2'-hydroxyls with 2'-O-methyls within the upper 2 basepairs of Stem 2 (RB455) was also well tolerated, consistent with the conserved secondary structure and truncation data, which indicates several combinations of basepair modifications in the upper portion of Stem 2 can be present within an anti-GPVI ligand and support high affinity binding to GPVI. Finally, substitution of the 2'-hydroxyl-2'-fluoro G-C basepair with a 2'-O-methyl G-C basepair in Stem 3 (RB462) resulted in a significant increase in affinity for GPVI. This substitution is expected to increase the stability of Stem 3, and is consistent with the consensus secondary structure of the anti-GPVI ligands, in which Stem 3 is predicted to be a short, 2 basepair stem.

Figure 10:
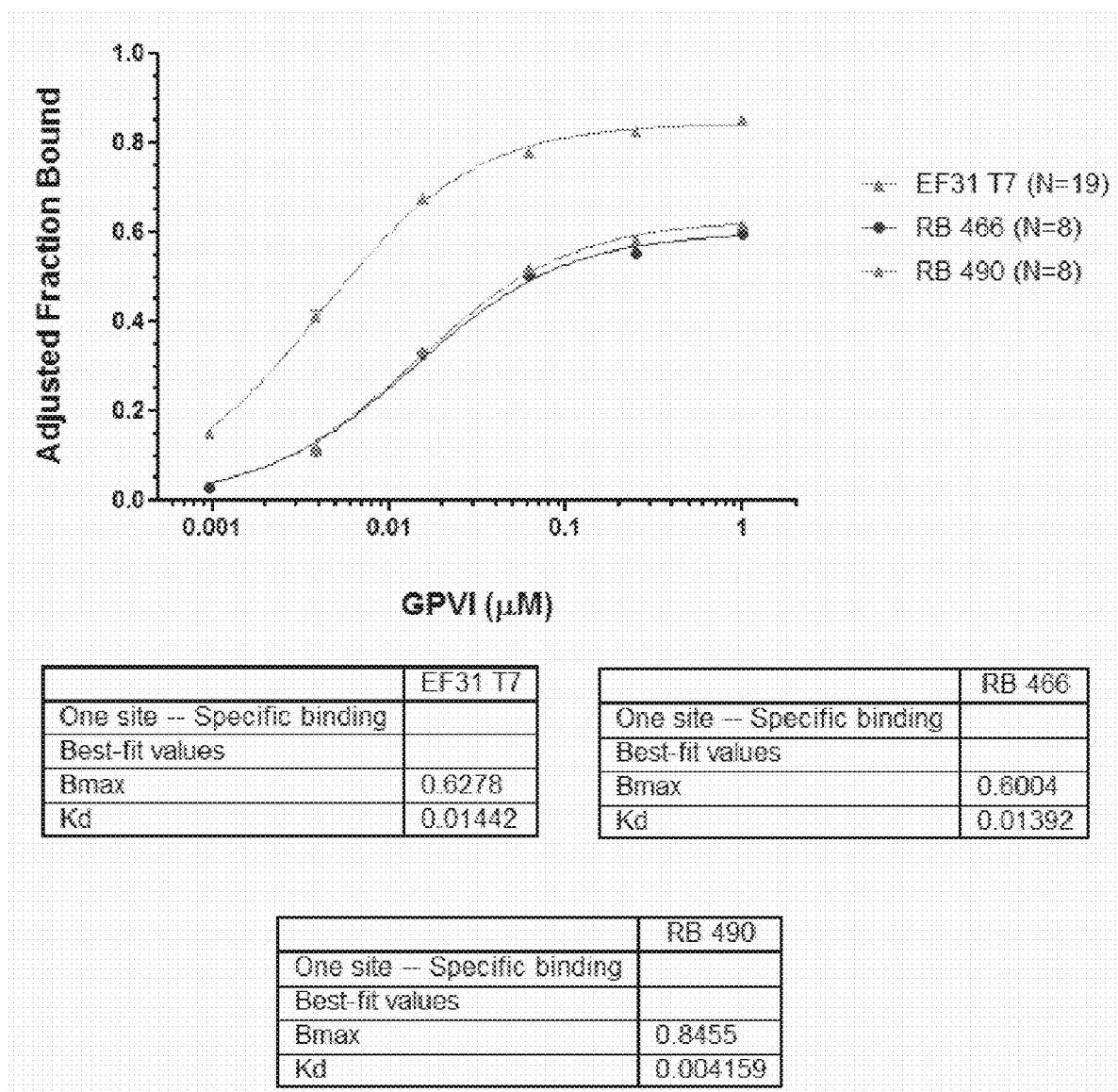
FIG. 10 shows results of GPVI binding assays for GPVI nucleic acid ligand variants.
Figure 11A:
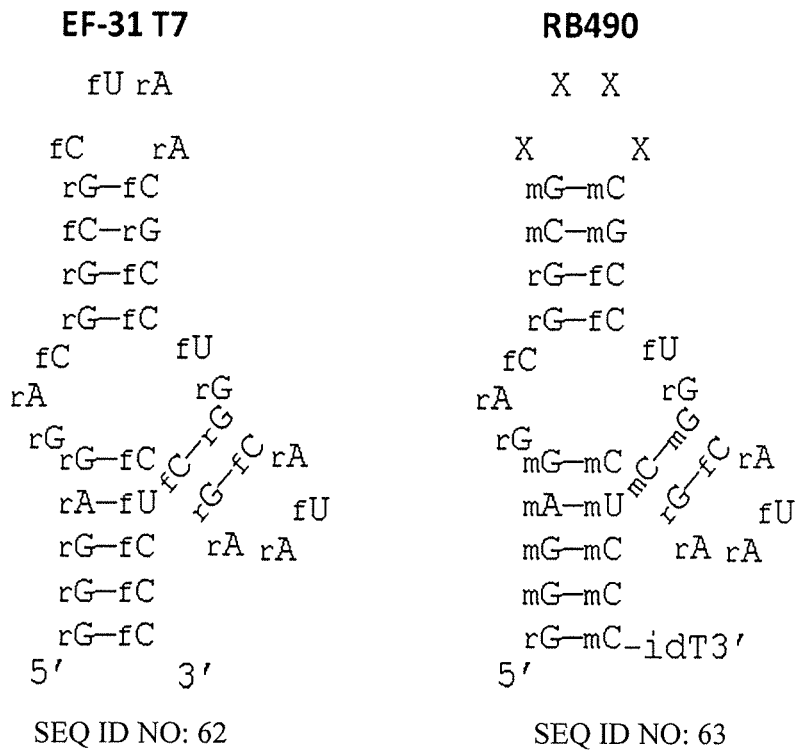
FIG. 11 shows predicted secondary structure and sugar substitutions of various GPVI nucleic acid ligands. SEQ ID NOs refer to the base sequence (without modifications) of a GPVI ligand.
Figure 11B:
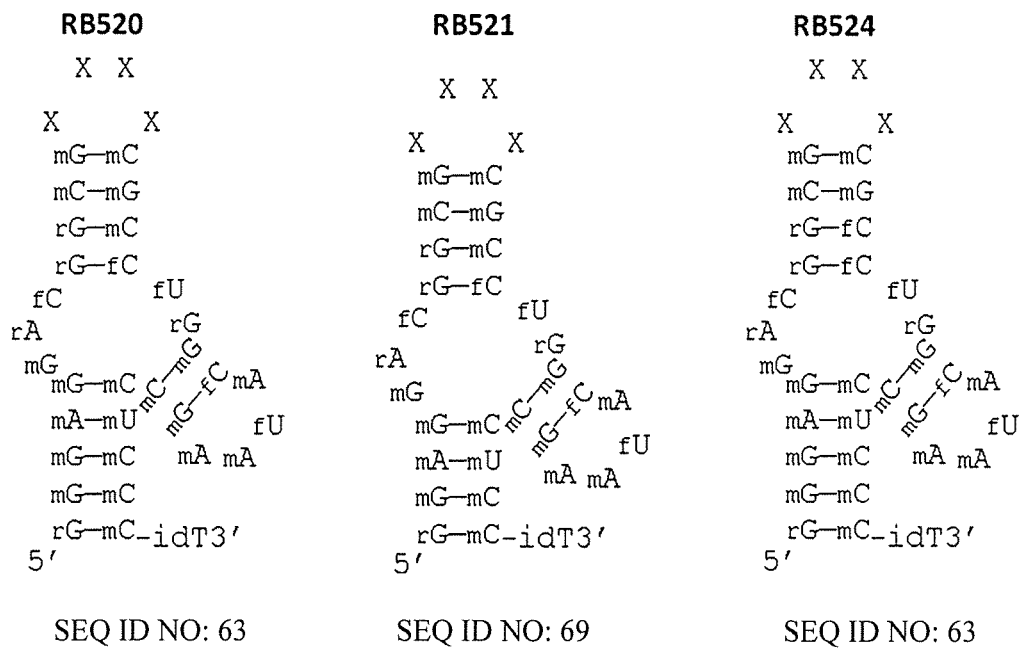

A composite molecule consisting of the substitutions within RB453, RB455, RB462 and RB466 was next synthesized (RB490) and tested for binding to GPVI in direct binding assays (See FIG. 10). Consistent with the affinity of compositions containing the individual sets of substitutions, RB490 bound GPVI with significantly greater affinity than the starting parent compound, with a $K_d$ for GPVI of ~4-5 nM as compared to ~14-15 nM for RB448. Subsequently, RB490 served as the parent compound for further optimization of the anti-GPVI ligand. It should be noted that, although the 2'-O-methyl substitution at the first residue of the molecule (G at position 1) is well tolerated, this modification greatly reduces the efficiency of 5' end-labeling of these compositions with $P^{32}$, and therefore this residue was left as a 2'-hydroxyl for the evaluation of the majority of the remaining modifications tested to facilitate direct binding studies. Secondary structure representations noting the sugar modifications for key composite compositions discussed within can be found in FIG. 11A-D.

Because the 5' half of Stem 2 is derived from the 5' fixed region of the ligand library used in the SELEX studies, the sequence composition of the stem sequence may be a less reliable guide for the likelihood of tolerability of substitutions for the 2'-hydroxyl or 2'-fluoro nucleotides in the bottom two basepairs of this stem than in sequences derived from the random region of the ligand library. Therefore, individual 2'-O-methyl for 2'-hydroxyl and 2'-fluoro substitutions were synthesized for the two G-C basepairs at the base of Stem 2 (RB497, 498, 499, and 500). 2'-O-methyl for 2'-hydroxyl substitutions were well tolerated for the G in the G-C basepair at the terminal position of Stem 2 (RB497), but the 2'-O-methyl for 2' fluoro substitution for the C of this basepair (RB498) was not well tolerated. Substitution of 2'-O-methyl for 2'-hydroxyl and for 2'-fluoro sugars was well tolerated for both the G and C in the G-C basepair in the second position of Stem 2 (RB499 and RB500), although a modest reduction in affinity was noted for the 2'-O-methyl substitution for the G (RB499).

Several of the consensus secondary structure predictions for the anti-GPVI ligands suggested that Stem 1 could be as short as 4 basepairs. Consistent with the consensus secondary structure, deletion of one of the G-C basepairs within Stem 1 was well-tolerated (RB507), with no loss of affinity as compared to the parental composition RB490.

Modification of the first G-C basepair within Stem 3 to a basepair containing 2'-O-methyl sugars (RB462) resulted in increased affinity as compared to a composition with a 2'-hydroxyl-2'-fluoro G-C basepair at that position. In contrast, 2'-O-methyl substitution of the sugars in the C-G basepair within Stem 3 resulted in loss of measurable GPVI affinity (RB463). Therefore, to further investigate the optimal sugar modification pattern for Stem 3, single substitutions of 2'-O-methyl for 2'-fluoro and 2'-hydroxyl sugars were made, respectively, for the C-G basepair of Stem 3 (RB501 and RB502). Substitution of a 2'-O-methyl for 2'-hydroxyl sugar in the G of this C-G basepair was well tolerated, with no apparent loss of affinity for GPVI (RB502), whereas the 2'-O-methyl for 2'-fluoro substitution in the C of this C-G basepair resulted in loss of measurable GPVI affinity (RB501), indicating this substitution within RB463 was the cause of the loss of GPVI binding observed with this composition. Overall, the preferred sugar modification pattern of Stem 2 is consistent with the anti-GPVI ligand consensus structure, and indicates the presence of the C within this C-G basepair of Stem 3 is conserved at the level of the sugar modification, stem formation, and primary sequence.

The sequence of Loop 4 is highly conserved within the anti-GPVI ligands, and therefore individual 2'-O-methyl substitutions were made for the sugars at each of these positions within Loop 4 (RB503, RB504, RB505 and RB506). 2'-O-methyl substitutions were well tolerated at each of these positions, with substitution of 2'-O-methyl for 2'-hydroxyl sugars at each A within Loop 4 yielding compositions with affinity for GPVI equivalent to the parent composition RB490 (RB503, RB505 and RB506), whereas the 2'-O-methyl for 2'-fluoro sugar substitution at the U within Loop 4 (RB504) resulted in a modest loss of GPVI affinity. Nonetheless, because the 2'-fluoro sugar modification affords significant nuclease resistant, the U within this loop was maintained as a 2'-fluoro nucleotide.

Mutational analysis (See Example 3, RB470, RB471 and RB472) demonstrated the importance of the GAC sequence within Loop 1 for high affinity binding to GPVI. Therefore, individual 2'-O-methyl and 2'-deoxy substitutions for the sugars at each of the positions within Loop 1 were synthesized to determine the preferred sugar modification pattern of the Loop 1 nucleotides (RB491, RB492, RB493, RB494, RB495, and RB496). 2'-O-methyl for 2'-hydroxyl substitution of the G within Loop 1 was well tolerated (RB491), within an affinity for GPVI equivalent to the parental composition RB490, and subsequently the 2'-deoxy substitution at this position was not tested (RB494). Substitution of 2'-deoxy for 2'-hydroxyl at the A within Loop 2 (RB495) was better tolerated than substitution of a 2'-O-methyl at this position (RB492), with an affinity for GPVI approximately equivalent to the parental composition RB490. Substitution of either 2'-O-methyl or 2'-deoxy sugars for the 2'-fluoro sugar of the C within Loop 2 resulted in modest loss of GPVI affinity, and therefore was not further pursued. Consistent with individual sugar substitutions within Loop 1, a composition with Loop 1 consisting of 2'-O-methyl G, 2'-deoxy A, and 2'-fluoro C (RB519) bound GPVI with higher affinity than a composition with Loop 1 consisting of 2'-O-methyl G, 2'-O-methyl A, and 2'-fluoro C (RB518).

Composite molecules consisting of substitutions within RB491, RB502, RB503, RB505 and RB506 (RB520) and consisting of substitutions within RB491, RB502, RB503, RB505, RB506 and RB507 (RB521) were synthesized to verify that incorporation of each of these substitutions within a single composition was well tolerated. As expected from the individual substitutions, RB520 and RB521 (same sugar substitution pattern as RB520 but with a 4 basepair Stem 1), bound GPVI with a $K_d$ similar to binding of RB490 to GPVI (approximately 6 nM vs 4-5 nM for RB490). Similarly, a composite consisting of these substitutions, but with a 2'-fluoro at the $2^{nd}$ G-C basepair of Stem 2 (RB524) also bound GPVI with high affinity.

RB524 contained 4 remaining 2' hydroxyl residues within the central core of the molecule (defined by the top of Stem 1, Loop 1, the base of Stem 2, Loop 3, Stem 3, and Loop 4). To determine optimal sugar substitution patterns for the remaining 2'-hydroxyl residues in the context of the highly modified RB524 composition, single, pair-wise and multiple sugar substitutions previously studied independently were synthesized in the RB524 background. Inclusion of a Loop 1 sequence of 2'-O-methyl G, 2'-deoxy A and 2'-fluoro C in conjunction with a 2'-deoxy substitution at the G in the terminal G-C basepair of Stem 2 into the RB524 background (RB526) resulted in a composition which retained high affinity binding to GPVI, with only two remaining 2'-hydroxyls. Subsequently, as expected from previous analysis of the length of Stem 1, deletion of a G-C basepair within the RB526 context (RB537) resulted in a composition that maintained high affinity GPVI binding. Substitution of a 2'-O-methyl for the 2'-hydroxy sugar at the G of Loop 3 (RB538) in the 537 background also resulted in a composition that maintained high affinity GPVI binding. Finally, substitution of a 2'-deoxy for the lone 2'-hydroxyl remaining at the G of the $2^{nd}$ G-C basepair within Stem 2 of RB538 (RB540) was well tolerated, yielding a composition fully-substituted at the 2' position of the sugars with a $K_d$ for GPVI of approximately 15 nM.

Figure 12:
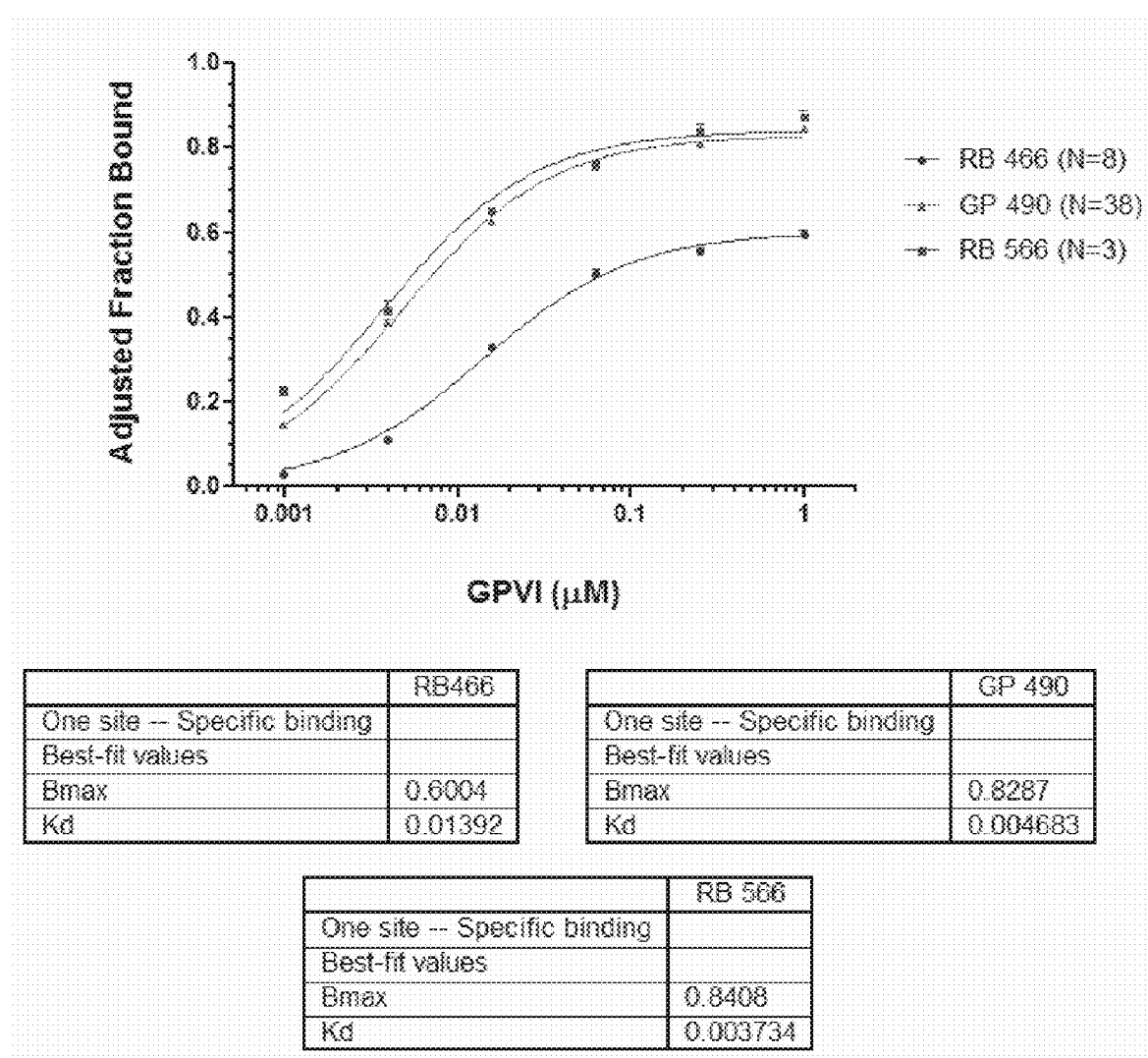
FIG. 12 shows results of GPVI binding assays for GPVI nucleic acid ligand variants.

Functional studies (See Example 6) indicated that there was a good correlation between affinity for GPVI and inhibition of collagen or CRP-induced platelet aggregation. Additionally, the ability of the anti-GPVI ligands to block CRP-induced platelet aggregation suggested that the ligands may bind to a region of the collagen binding domain overlapping or near to the CRP-binding site on GPVI. The collagen binding site on GPVI has a net positive charge, and a large electropositive surface. Therefore, phosphorothioate substitutions were made within RB540 in the regions consisting of 2'-deoxy substitutions within Loop 1 and Stem 2, as phosphorothioate substitutions increase the net electronegativity of oligonucleotides; and thereby may lead to increase affinity of the ligands for GPVI. Additionally, phosphorothioate substitutions in the context of 2'-deoxy sugar-containing residues may afford additional protection from nuclease degradation. Individual phosphorothioate substitutions were made flanking the A and C of Loop 1, and the G's of the terminal 2 basepairs of Stem 2 (RB546, RB547, RB548, RB549, RB550) in the RB540 background. Substitution of single phosphorothiates between the two G's at the base of Stem 2 (RB549) or 3' to the $2^{nd}$ G of Stem 2 (RB550) enhanced the affinity of the ligands for GPVI. Inclusion of both of these phosphorothioate substitutions into a composite anti-GPVI ligand (RB566) further enhanced the affinity of the ligand for GPVI, resulting in an ligand exhibiting a slightly enhanced affinity for GPVI as compared to RB490, with a $K_d$ for GPVI of approximately 2-4 nM, and a greatly enhanced affinity as compared to RB540 (see FIG. 12).

In addition to the extent of nuclease stabilization, distribution and half-life of ligands post parenteral administration is greatly impacted by their molecular weight. Conjugation of ligands to high molecular weight carriers, such as high molecular weight polyethylene glycol (PEG), limit the distribution of an ligand to mainly the plasma compartment, leading to higher $C_{max}$ per dose unit, and greatly limit renal filtration of the ligand, and thus greatly enhance the ligand's in vivo potency and circulating half-life. Given that a control agent may be administered to finely tune the potency and half-life of an anti-GPVI ligands (see Example 8), anti-GPVI ligands were conjugated to a high molecular weight carrier to provide the greatest potential half-life with distribution mainly limited to the plasma compartment. PEGylation of ligands can be achieved by conjugation of the PEG to a unique site on the ligand, added by incorporation of a site-specific linker to the ligand during synthesis. Therefore, the impact of linker addition and PEG conjugation to RB540, RB549 and RB566 was assessed. 5' hexylamino-linker containing compositions of these respective ligands (RB542, RB560 and RB567) bound GPVI with affinities equivalent to the non-linker containing parent compositions. It should be noted that, for compositions containing either a 5' linker or a 5' linker and PEG, the sugar at G of position 1 of the ligand was 2'-O-methyl. Additionally, as incorporation of a linker to the 5' end of the ligand prevents labeling of the 5' end with $P^{32}$, affinity of linker and PEG modified ligands was done via competition binding against the cognate radiolabeled parent ligand, using essentially the methods outlined in Example 1. Conjugation of a branched 40 KDa PEG to the respective linker containing ligands (RB569, RB570, RB571) resulted in an approximately 1.2 to 1.7 fold decrease in GPVI affinity as compared to the non-linker, or linker only, containing parent compositions (eg. RB566 for RB571). Thus, RB571, which consists of the RB566 composition (with a 2'-O-methyl G at position 1) conjugated to a 40 KDa PEG, exhibits a $K_d$ for GPVI of approximately 5 nM.

TABLE 6

Modified GPVI Ligands

| RB ID | Modified Sequence | Binding | SEQ ID NO |
|---|---|---|---|
| RB448 | rGrGrGrArGrGrAfCrGrGfCrGfCfUrArAfCrGfCfCfUrGrGfCrAfUrArArGfCfCfUfCfCfCiT | +++ | 62 |
| RB450 | mGmGrArGrGrAfCrGrGfCrGfCfUrArAfCrGfCfCfUrGrGfCrAfUrArArGfCfCfUfCmCmCiT | ND | 62 |

TABLE 6-continued

Modified GPVI Ligands

| RB ID | Modified Sequence | Binding | SEQ ID NO |
|---|---|---|---|
| RB451 | mGmGmGrArGrGrAfCrGrGfCrGfCfUrArAfCrGfCfCfUrGrGfCrAfUrArArGfCfCfUmCmCmCiT | ND | 62 |
| RB452 | mGmGmGmArGrGrAfCrGrGfCrGfCfUrArAfCrGfCfCfUrGrGfCrAfUrArArGfCfCmCmCmCiT | +++ | 62 |
| RB453 | mGmGmGmAmGrGrAfCrGrGfCrGfCfUrArAfCrGfCfCfUrGrGfCrAfUrArArGfCmCmUmCmCiT | ++++ | 62 |
| RB454 | rGrGrGrArGmGmAmCrGrGfCfUrArAfCrGfCfCfUrGrGfCrAfUrArArGfCfCfUfCfCfCiT | ND | 62 |
| RB455 | rGrGrGrArGrGrAfCrGrGmCmCfCfUrArAmCmGfCfCfUrGrGfCrAfUrArArGfCfCfUfCfCfCiT | +++ | 62 |
| RB456 | rGrGrGrArGrGrAfCrGmGmCmGfCfUrArAmCmGmCfCfUrGrGfCrAfUrArArGfCfCfUfCfCfCiT | ND | 62 |
| RB459 | rGrGrGrArGrGrAfCrGrGfCrGfCfUrArAfCrGfCfCmUrGrGfCrAfUrArArGfCfCfUfCfCfCiT | dead | 62 |
| RB460 | rGrGrGrArGrGrAfCrGrGfCrGfCfUrArAfCrGfCfCfUmGrGfCrAfUrArArGfCfCfUfCfCfCiT | +++ | 62 |
| RB461 | rGrGrGrArGrGrAfCrGrGfCrGfCfUrArAfCrGfCfCmUmGrGfCrAfUrArArGfCfCfUfCfCfCiT | dead | 62 |
| RB462 | rGrGrGrArGrGrAfCrGrGfCrGfCfUrArAfCrGfCfCfUrGmGfCrAfUrArArGmCfCfUfCfCfCiT | ++++ | 62 |
| RB463 | rGrGrGrArGrGrAfCrGrGfCrGfCfUrArAfCrGfCfCfUrGrGmCrAfUrArAmGfCfCfUfCfCfCiT | dead | 62 |
| RB466 | rGrGrGrArGrGrAfCrGrGfCrG(6GLY)fCrGfCfCfUrGrGfCrAfUrArArGfCfCfUfCfCfCiT | +++ | 63 |
| RB469 | (6FAM)rGrGrGrArGrGrAfCrGrGfCrGfCfUrArAfCrGfCfCrArArGfCrAfUrArArGfCfCfUfCfCfCiT | dead(**) | 64 |
| RB470 | rGrGrGrArGfCrAfCrGrGfCrG(6GLY)fCrGfCfCfUrGrGfCrAfUrArArGfCfCfUfCfCfCiT | dead | 65 |
| RB471 | rGrGrGrArGrGfUfCrGrGfCrG(6GLY)fCrGfCfCfUrGrGfCrAfUrArArGfCfCfUfCfCfCiT | dead | 66 |
| RB472 | rGrGrGrArGrGrArGrGfCrG(6GLY)fCrGfCfCfUrGrGfCrAfUrArArGfCfCfUfCfCfCiT | dead | 67 |
| RB473 | mGrGrGrArGrGrAfCrGrGfCrG(6GLY)fCrGfCfCfUrGrGfCrAfUrArArGfCfCfUfCfCfCiT | ND | 63 |
| RB478 | (6FAM)rGrGrGrArGrGrAfCrGrGfCrG(6GLY)fCrGfCfCfUrGrGfCrAfUrArArGfCfCfUfCfCfCiT | +++(**) | 63 |
| RB480 | rGrGrGrArGrGrAfCrGrGfCrG(6GLY)fCrGfCfCfUfUrGrGfCrAfUrArArGfCfCfUfCfCfCiT | +++ | 68 |
| RB482 | rGrGrGrArGrGrAfCrGrGmCmG(6GLY)mCmGfCfCfUrGrGfCrAfUrArArGfCfCfUfCfCfCiT | ND | 63 |
| RB485 | mGmGmGmAmGrGrAfCrGrGfCrG(6GLY)fCrGfCfCfUrGrGfCrAfUrArArGfCmCmCmCmCiT | ND | 63 |
| RB487 | mGmGmGmAmGrGrAfCrGrGmCmG(6GLY)mCmGfCfCfUrGrGfCrAfUrArArGfCmCmUmCmCmCiT | ND | 63 |
| RB488 | rGmGmGmAmGrGrAfCrGrGmCmG(6GLY)mCmGfCfCfUrGrGfCrAfUrArArGfCmCmUmCmCmCiT | ++++ | 63 |
| RB490 | rGmGmGmAmGrGrAfCrGrGmCmG(6GLY)mCmGfCfCfUrGmGfCrAfUrArArGmCmCmUmCmCmCiT | ++++ | 63 |
| RB491 | rGmGmGmAmGmGrAfCrGrGmCmG(6GLY)mCmGfCfCfUrGrGfCrAfUrArArGmCmCmUmCmCmCiT | ++++ | 63 |
| RB492 | rGmGmGmAmGrGmAfCrGrGmCmG(6GLY)mCmGfCfCfUrGrGfCrAfUrArArGmCmCmUmCmCmCiT | +++ | 63 |
| RB493 | rGmGmGmAmGrGrAmCrGrGmCmG(6GLY)mCmGfCfCfUrGrGfCrAfUrArArGmCmCmUmCmCmCiT | +++ | 63 |
| RB494 | rGmGmGmAmGGrAfCrGrGmCmG(6GLY)mCmGfCfCfUrGmGfCrAfUrArArGmCmCmUmCmCmCiT | ND | 63 |
| RB495 | rGmGmGmAmGrGAfCrGrGmCmG(6GLY)mCmGfCfCfUrGmGfCrAfUrArArGmCmCmUmCmCmCiT | ++++ | 63 |
| RB496 | rGmGmGmAmGrACrGrGmCmG(6GLY)mCmGfCfCfUrGmGfCrAfUrArArGmCmCmUmCmCmCiT | +++ | 63 |
| RB497 | rGmGmGmAmGrGrAfCmGrGmCmG(6GLY)mCmGfCfCfUrGmGfCrAfUrArArGmCmCmUmCmCmCiT | ++++ | 63 |
| RB498 | rGmGmGmAmGrGrAfCrGmGmCmG(6GLY)mCmGfCmCfUrGmGfCrAfUrArArGmCmCmUmCmCmCiT | ++ | 63 |
| RB499 | rGmGmGmAmGrGrAfCrGmGmCmG(6GLY)mCmGfCfCfUrGmGfCrAfUrArArGmCmCmUmCmCmCiT | +++ | 63 |
| RB500 | rGmGmGmAmGrGrAfCrGrGmCmG(6GLY)mCmGfCfCmCfUrGmGfCrAfUrArArGmCmCmUmCmCmCiT | ++++ | 63 |
| RB501 | rGmGmGmAmGrGrAfCrGrGmCmG(6GLY)mCmGfCfCfUrGmGmCrAfUrArArGmCmCmUmCmCmCiT | dead | 63 |
| RB502 | rGmGmGmAmGrGrAfCrGrGmCmG(6GLY)mCmGfCfCfUrGmGfCrAfUrArAmGmCmCmUmCmCmCiT | ++++ | 63 |
| RB503 | rGmGmGmAmGrGrAfCrGrGmCmG(6GLY)mCmGfCfCfUrGmGfCmAfUrArArGmCmCmUmCmCmCiT | ++++ | 63 |
| RB504 | rGmGmGmAmGrGrAfCrGrGmCmG(6GLY)mCmGfCfCfUrGmGfCrAmUrArArGmCmCmUmCmCmCiT | +++ | 63 |

TABLE 6-continued

Modified GPVI Ligands

| RB ID | Modified Sequence | Binding | SEQ ID NO |
|---|---|---|---|
| RB505 | rGmGmGmAmGrGrAfCrGrGmCmG(6GLY)mCmGfCfCfUrGmGfCrAfUmArAmGmCmCmUmCmCmCiT | ++++ | 63 |
| RB506 | rGmGmGmAmGrGrAfCrGrGmCmG(6GLY)mCmGfCfCfUrGmGfCrAfUrAmAmGmCmCmUmCmCmCiT | ++++ | 63 |
| RB507 | rGmGmAmGrGrAfCrGrGmCmG(6GLY)mCmGfCfCfUrGmGfCrAfUrArArGmCmCmUmCmCmCiT | ++++ | 69 |
| RB508 | (C6L)rGmGmGmAmGrGrAfCrGrGmCmG(6GLY)mCmGfCfCfUrGmGfCrAfUrArAmGmCmCmUmCmCmCiT | ++++ | 63 |
| RB509 | rGmGmGmAmGrGrAfCrGrGmCmG(6GLY)mCmGfCfCfUrGmGfCAfUrArArGmCmCmUmCmCmCiT | ND | 63 |
| RB510 | rGmGmGmAmGrGrAfCrGrGmCmG(6GLY)mCmGfCfCfUrGmGfCrATrArArGmCmCmUmCmCmCiT | ND | 70 |
| RB511 | rGmGmGmAmGrGrAfCrGrGmCmG(6GLY)mCmGfCfCfUrGmGfCrAfUArArGmCmCmUmCmCmCiT | ND | 63 |
| RB512 | rGmGmGmAmGrGrAfCrGrGmCmG(6GLY)mCmGfCfCfUrGmGfCrAfUrAArGmCmCmUmCmCmCiT | ND | 63 |
| RB517 | rGmGmGmAmGmGmAmCrGrGmCmG(6GLY)mCmGfCfCfUrGmGfCrAfUrArArGmCmCmUmCmCmCiT | + | 63 |
| RB518 | rGmGmGmAmGmGmAfCrGrGmCmG(6GLY)mCmGfCfCfUrGmGfCrAfUrArArGmCmCmUmCmCmCiT | +++ | 63 |
| RB519 | rGmGmGmAmGmGmGAfCrGrGmCmG(6GLY)mCmGfCfCfUrGmGfCrAfUrArArGmCmCmUmCmCmCiT | ++++ | 63 |
| RB520 | rGmGmGmAmGrGrAfCrGrGmCmG(6GLY)mCmGmCfCfUrGmGfCmAfUmAmAmGmCmCmUmCmCmCiT | ++++ | 63 |
| RB521 | rGmGmAmGmGrAfCrGrGmCmG(6GLY)mCmGmCfCfUrGmGfCmAfUmAmAmGmCmCmUmCmCiT | ++++ | 69 |
| RB522 | rGmGmGmAmGmGmAfCrGrGmCmG(6GLY)mCmGmCfCfUrGmGfCmAfUmAmAmGmCmCmUmCmCmCiT | ++ | 63 |
| RB523 | rGmGmGmAmGmGmAfCmGrGmCmG(6GLY)mCmGmCfCfUrGmGfCmAfUmAmAmGmCmCmUmCmCmCiT | + | 63 |
| RB524 | rGmGmGmAmGrGrAfCrGrGmCmG(6GLY)mCmGfCfCfUrGmGfCmAfUmAmAmGmCmCmUmCmCmCiT | +++ | 63 |
| RB525 | rGmGmGmAmGmGAfCmGrGmCmG(6GLY)mCmGfCfCfUrGmGfCmAfUmAmAmGmCmCmUmCmCmCiT | ++ | 63 |
| RB526 | rGmGmGmAmGmGAfCGrGmCmG(6GLY)mCmGfCfCfUrGmGfCmAfUmAmAmGmCmCmUmCmCmCiT | +++ | 63 |
| RB527 | rGmGmGmAmGmGmAfCmGrGmCmG(6GLY)mCmGfCfCfUrGmGfCmAfUmAmAmGmCmCmUmCmCmCiT | + | 63 |
| RB528 | rGmGmGmAmGmGmAfCGrGmCmG(6GLY)mCmGfCfCfUrGmGfCmAfUmAmAmGmCmCmUmCmCmCiT | + | 63 |
| RB531 | rGmGmGmAmGmGAfCGrGmCmG(6GLY)mCmGfCfCfUmGmGfCmAfUmAmAmGmCmCmUmCmCmCiT | +++ | 63 |
| RB532 | rGmGmGmAmGmGAfCGrGmCmG(6GLY)mCmGfCfCfUmGmGfCmGfUmAmAmGmCmCmUmCmCmCiT | +++ | 71 |
| RB533 | rGmGmGmAmGmGAfCGrGmCmG(6GLY)mCmGfCfCfUfUmGmGfCmAfUmAmAmGmCmCmUmCmCmCiT | +++ | 68 |
| RB534 | rGmGmGmAmGmGAfCGrGmCmG(6GLY)mCmGfCfCfUfUmGmGfCmGfUmAmAmGmCmCmUmCmCmCiT | +++ | 72 |
| RB535 | rGmGmGmAmGmGAfCGrAmCmG(6GLY)mCmGfUfCfUrGmGfCmAfUmAmAmGmCmCmUmCmCmCiT | +++ | 73 |
| RB536 | rGmGmGmAmGmGAfCmGrAmCmG(6GLY)mCmGfUfCfUrGmGfCmAfUmLmAmGmCmCmUmCmCmCiT | + | 73 |
| RB537 | rGmGmAmGmGAfCGrGmCmG(6GLY)mCmGfCfCfUrGmGfCmAfUmAmAmGmCmCmUmCmCiT | ++++ | 69 |
| RB538 | rGmGmAmGmGAfCGrGmCmG(6GLY)mCmGfCfCfUmGmGfCmAfUmAmAmGmCmCmUmCmCiT | +++ | 69 |
| RB540 | rGmGmAmGmGAfCGGmCmG(6GLY)mCmGfCfCfUmGmGfCmAfUmAmAmGmCmCmUmCmCiT | +++ | 69 |
| RB541 | (C6L)mGmGmAmGmGAfCGrGmCmG(6GLY)mCmGfCfCfUmGmGfCmAfUmAmAmGmCmCmUmCmCiT | ND | 69 |
| RB542 | (C6L)mGmGmAmGmGAfCGGmCmG(6GLY)mCmGfCfCfUmGmGfCmAfUmAmAmGmCmCmUmCmCiT | +++ | 69 |
| RB546 | rGmGmAmGmG(s)AfCGGmCmG(6GLY)mCmGfCfCfUmGmGfCmAfUmAmAmGmCmCmUmCmCiT | +++ | 69 |
| RB547 | rGmGmAmGmGA(s)fCGGmCmG(6GLY)mCmGfCfCfUmGmGfCmAfUmAmAmGmCmCmUmCmCiT | +++ | 69 |
| RB548 | rGmGmAmGmGAfC(s)GGmCmG(6GLY)mCmGfCfCfUmGmGfCmAfUmAmAmGmCmCmUmCmCiT | +++ | 69 |
| RB549 | rGmGmAmGmGAfCG(s)GmCmG(6GLY)mCmGfCfCfUmGmGfCmAfUmAmAmGmCmCmUmCmCiT | ++++ | 69 |
| RB550 | rGmGmAmGmGAfCGG(s)mCmG(6GLY)mCmGfCfCfUmGmGfCmAfUmAmAmGmCmCmUmCmCiT | ++++ | 69 |
| RB551 | rGmGmAmGmGAfCrGGmCmG(6GLY)mCmGfCfCfUmGmGfCmAfUmAmAmGmCmCmUmCmCiT | +++ | 69 |
| RB552 | rGmGmAmGmG(s)AfCrGGmCmG(6GLY)mCmGfCfCfUmGmGfCmAfUmAmAmGmCmCmUmCmCiT | +++ | 69 |

TABLE 6-continued

Modified GPVI Ligands

| RB ID | Modified Sequence | Binding | SEQ ID NO |
|---|---|---|---|
| RB553 | rGmGmAmGmGA(s)fCrGGmCmG(6GLY)mCmGfCfCfUmGmGfCmAfUmAmAmGmCmCmUmCmCiT | +++ | 69 |
| RB554 | rGmGmAmGmGAfC(s)rGGmCmG(6GLY)mCmGfCfCfUmGmGfCmAfUmAmAmGmCmCmUmCmCiT | ++++ | 69 |
| RB555 | rGmGmAmGmGAfCrG(s)GmCmG(6GLY)mCmGfCfCfUmGmGfCmAfUmAmAmGmCmCmUmCmCiT | ++++ | 69 |
| RB556 | rGmGmAmGmGAfCrGG(s)mCmG(6GLY)mCmGfCfCfUmGmGfCmAfUmAmAmGmCmCmUmCmCiT | ++++ | 69 |
| RB560 | (C6L)mGmGmAmGmGAfCG(s)GmCmG(6GLY)mCmGfCfCfUmGmGfCmAfUmAmAmGmCmCmUmCmCiT | ++++ | 69 |
| RB561 | rGmGmAmGmGAfC(s)G(s)GmCmG(6GLY)mCmGfCfCfUmGmGfCmAfUmAmAmGmCmCmUmCmCiT | ++++ | 69 |
| RB562 | (C6L)mGmGmAmGmGAfC(s)G(s)GmCmG(6GLY)mCmGfCfCfUmGmGfCmAfUmAmAmGmCmCmUmCmCiT | ND | 69 |
| RB566 | rGmGmAmGmGAfCG(s)G(s)mCmG(6GLY)mCmGfCfCfUmGmGfCmAfUmAmAmGmCmCmUmCmCiT | ++++ | 69 |
| RB567 | (C6L)mGmGmAmGmGAfCG(s)G(s)mCmG(6GLY)mCmGfCfCfUmGmGfCmAfUmAmAmGmCmCmUmCmCiT | ++++ | 69 |
| RB569 | (PEG40KGL2-NOF)(C6L)mGmGmAmGmGAfCG(s)GmCmG(6GLY)mCmGfCfCfUmGmGfCmAfUmAmAmGmCmCmUmCmCiT | ++++ | 69 |
| RB570 | (PEG40KGL2-NOF)(C6L)mGmGmAmGmGAfCGGmCmG(6GLY)mCmGfCfCfUmGmGfCmAfUmAmAmGmCmCmUmCmCiT | +++ | 69 |
| RB571 | (PEG40KGL2-NOF)(C6L)mGmGmAmGmGAfCG(s)G(s)mCmG(6GLY)mCmGfCfCfUmGmGfCmAfUmAmAmGmCmCmUmCmCiT | ++++ | 69 |

++++ Kd less than 10 nM
+++ Kd 10 nM-24 nM
++ Kd 25-40 nM
+ Kd > 40 nM
dead No Binding
ND Not Determined
(**)Compound assayed functionally
All ligands described in the column titled, "Modified Sequence" are modified versions of SEQ ID NO: 62 (RB448)
rG = 2'Ribo G;
rA = 2'Ribo A;
mG = 2'O-Methyl G;
mA = 2'O-Methyl A;
mC = 2'O-Methyl C;
mU = 2'O-Methyl U;
fC = 2'Fluoro C;
fU = 2'Fluoro U;
G = 2'Deoxy G;
A = 2'Deoxy A;
iT-inverted deoxythymidine;
(s)-phosphorothioate linkage;
(C6L) = hexylamino linker;
(6GLY) = hexaethylene glycol linker ((incorporated using 9-O-Dimethoxytrityl-triethylene glycol,1-[(2-cyanoethyl)-(N,N-diisopropyl)]-phosphoramidite);
(PEG40KGL2-NOF) = 40 kDa Branched PEG (SUNBRIGHT GL2-400GS2 product);
(6FAM): 6-carboxyfluorescein The "RB ID" is a unique identifier that refers to the ligand having the sequence with specific modifications noted in the column titled, "Modified Sequence."
The "SEQ ID NO:" refers to the corresponding nucleic acid sequence (DNA and/or RNA) without modifications.

Example 5

Methods for Evaluating Antiplatelet Activity, Specificity of Activity, and Modulation of Activity of Anti-GPVI Ligands A. Collagen-Induced Platelet Aggregation (CIPA) Assay in PRP and WP 1. Platelet Rich Plasma Preparation (PRP) and Aggregation Studies:

Human platelet-rich plasma (PRP) was prepared from fresh whole blood collected in 60 ml syringes using 0.3 mM PPACK in saline (9:1 blood:anticoagulant saline mix; Biomol Cat #PI1117) as an anticoagulant. The blood was centrifuged at low speed centrifugation (250×g) in 50 ml conical tubes for 16 minutes. The platelet rich plasma separated from the blood cells by centrifugation was removed using 10 ml serological pipettes and platelet poor plasma (PPP) was prepared from leftover blood by high speed centrifugation at 2200×g for 10 minutes. The PPP was removed and saved for the light transmission aggregometry (LTA) blank.

Platelet aggregation in PRP was monitored using 450 μL of PRP (plus 25 μL of Saline) at 37° C. (stirred at 1200 rpm) in a Chrono-Log (Havertown, Pa.) lumi-aggregometer for 6 minutes. Aggregation is initiated using 25 μL of collagen as agonist. 500 μL of platelet-poor plasma (PPP) is used as baseline in the aggregometer. For screening anti-GPVI ligands for the ability to block CIPA, 450 μL of PRP is incubated with 25 μt of solution containing the anti-GPVI ligand, at a concentration to yield the desired final concentration, for 3 minutes at 37° C. in the aggregometer cell with constant stirring at 1200 rpm before addition of the agonist collagen. Platelet aggregation is initiated by the addition of indicated concentrations of collagen (Equine Tendon Collagen Fibril Type-1; Chronolog, Cat #385) to yield a percent aggregation between 70-90%, and the light transmission is continuously recorded for 4-6 min.

2. Washed Platelet Preparation (WP) and Aggregation Studies:

Human washed platelets were prepared essentially as described by Mustard et al. (1972; Br. J. Haematol 22, 193-204). Briefly, human blood was collected into one-sixth volume of acid/citrate/dextrose (ACD) buffer (85 mM sodium citrate, 65 mM citric acid, and 110 mM glucose), placed in a water bath at 37° C. for 30 minutes then centrifuged at 250×g for 16 minutes at room temperature. Platelet-rich plasma was removed and centrifuged at 2200×g for 13 minutes at room temperature then resuspended in 40 mL of HEPES-buffered Tyrode's solution (136.5 mM NaCl, 2.68 mM KCl, 1 mM $MgCl_2$, 2 mM $CaCl_2$, 12 mM $NaHCO_3$, 0.43 mM $NaH_2PO_4$, 5.5 mM glucose, 5 mM HEPES pH 7.4, 0.35% bovine serum albumin) containing 10 U/mL heparin and 5 μM (final concentration) prostaglandin $I_2$ ($PGI_2$). The platelet suspension was incubated in a 37° C. water bath for 10 minutes, 5 μM (final concentration) $PGI_2$ added and the mixture centrifuged at 1900×g for 8 minutes. The resulting pellet was resuspended in 40 mL of HEPES-buffered Tyrode's solution containing 5 μM (final concentration) $PGI_2$ and then incubated for 10 minutes in a 37° C. water bath, and centrifuged at 1900×g for 8 minutes. The pellet is resuspended at a density of $3 \times 10^8$ platelets/mL in HEPES-buffered Tyrode's solution containing 0.1 U/mL potato apyrase and incubated in a 37° C. water bath for 1 hr prior to use in aggregometry studies.

Collagen-induced WP platelet aggregation was determined by measuring the transmission of light through a 0.5 ml suspension of stirred (1200 rpm) washed platelets (425 ul washed platelets, 25 μl fibrinogen, 25 μl of inhibitors or controls and 25 μA of collagen) in a lumi-aggregometer at 37° C. (Chrono-Log Corp. Havertown, Pa.). The baseline of the instrument was set using 0.5 ml of Hepes-buffered Tyrode's solution. Prior to aggregation measurements, the platelet suspension was supplemented with 1 mg/ml fibrinogen. Platelet aggregation was initiated by the addition of indicated concentrations of Collagen (Equine Tendon Collagen Fibril Type-1; Chronolog, Cat #385) to yield a percent aggregation between 70-90%, and the light transmission was continuously recorded for at least 6 min. For screening anti-GPVI ligands or controls (various mutants of ligands) for the ability to block CIPA, anti-GPVI ligands were added to the platelet suspension at a concentration to yield the desired final concentration, and incubated for 3 min before addition of collagen, and the response was recorded for 4-6 min after collagen addition.

The potency of collagen was determined for each donor from the maximal extent of percentage aggregation obtained from a dose response curve using 2× serial dilution of 4 μg/ml of collagen in saline, and a challenge concentration was determined. The ability of anti-GPVI ligands to inhibit CIPA was tested in both WP and PRP preparations as described above, using a broad range of anti-GPVI ligand concentrations (2 μM-7.8 nM).

B. CRP Induced Platelet Aggregation (CRPIPA) Assay in WP and PRP

Cross-linked collagen related peptide, CRP-XL [(GPO)$_{10}$], is a selective, potent agonist of GPVI (Farndale et al., J. Thromb Haemost 2004; 2: 561-573; Smethurst P A et al., J. Biol. Chem. 2007; 282: 1296-1304) which can be used to specifically trigger platelet aggregation via the GPVI receptor in both PRP and WP aggregation assays.

The potency of CRP-XL was determined for each donor from the maximal extent of percentage aggregation obtained from a dose response curve using 2× serial dilution of 400 ng/ml of CRP-XL in saline, and a challenge concentration was determined. The ability of anti-GPVI ligands to inhibit CRPIPA was tested in both WP and PRP preparations as described above, using a broad range of anti-GPVI ligand concentrations (2 μM-7.8 nM).

C. Percent Reduction of Collagen or CRP-Induced Platelet Aggregation and $IC_{50}$ Determination Percent reduction of collagen or CRP induced platelet aggregation by anti-GPVI ligands was calculated taking the maximum extent of platelet aggregation of given challenge collagen or CRP concentration as 100 percent and plotted using GraphPad Prism.

When a broad range of concentrations of anti-GPVI ligands were tested (usually from 1 nM to 1 uM concentration), an $IC_{50}$ value was also obtained. $IC_{50}$ values represent the concentration of ligand necessary to inhibit by 50% the aggregation elicited by a given concentration of collagen or CRP.

D. In vitro Flow Based Platelet Adhesion Assay in Whole Blood for Anti-GPVI Ligand activity using Bioflux™ 200 (Fluxion Biosciences, Inc.,)

1. Preparation of the Test Plate with Collagen Coating:

For the flow experiments, Bioflux 48 well plates (P/N 0009-0013) were routinely used. The plates were primed with 0.02M acetic acid for 5 min at 5 dyn/cm$^2$, and then 25 μg/ml of diluted fibrillar collagen (Chrono-Log P/N 385) in 0.02M acetic acid was perfused from the inlet well for 10 min at 5 dyn/cm$^2$. The flow was stopped and the plate incubated at room temp for 1 hour. The collagen was washed with PBS at 5 dyn/cm$^2$ for 10 min. The collagen coated plate was then blocked by completely filling the outlet well (1 ml) with PBS+5% BSA w/v and perfusing the solution into the channel at 5 dyn/cm$^2$ for 15 min. The flow was stopped and the plate was incubated for an additional 10 minutes at room temp. Excess PBS+BSA was removed from all wells and the plate was kept at room temperature for same day use or kept at 4° C. in PBS+BSA (up to two weeks).

2. Whole Blood Preparation for Perfusion and the Flow Experiment:

The blood was drawn from healthy volunteers into PPACK (0.3 mM)/CTI (60 μg/ml) anticoagulant into 60 mL syringes using a 19$^{3/4}$" gauge needle. The blood was immediately fluorescently labeled with 4 μM Calcein-AM (Invitrogen P/N C3100MP) for 1 hr at 37° C. (Calcein-AM was added to the blood very gently by inverting the tube a few times to mix and the blood was used within 3.5 hrs of draw). The experiment was initiated by adding 200 μL of labeled blood on top of the outlet well and perfusion begun immediately using 20 dyn/cm$^2$ whole blood flow settings at 37° C. using Bioflux™ software. The data (fluorescence images of platelet aggregates) was collected using a time lapse fluorescence inverted microscope (Zeiss 200M Axiovert Microscope attached to an Axiocam Charged-Coupled Device camera and Axiovision software) every 6 seconds for a total duration of 6 minutes. For test articles (anti-GPVI ligands, control ligands or control antibodies) 200 μL, of labeled blood was incubated with the indicated concentrations of ligands (or buffer-F; in 10 μL volume) for 4 minutes at room temperature before addition to the outlet well. The tagged image file (tiff) formatted images were used to calculate fluorescence intensity using Bioflux Montage™ software and then the data was exported to Microsoft excel and plotted using Graphpad Prism. Data was normalized to the fluorescent signal observed in the control chamber at the time at which the control chamber was occluded by fluorescent platelet aggregates (defined as the maximum platelet response), which typically occurred between 3-4 minutes in the absence of an anti-GPVI ligand.

E. ADP Induced Platelet Aggregation (AIPA) Assay, TRAP Induced Platelet. Aggregation (TIPA), Arachidonic Acid Induced Platelet Aggregation (AAIPA) Assay, and Ristocetin Induced Platelet Aggregation (RIPA) Assay for Evaluation of Anti-GPVI Ligand Specificity for GPVI The specificity of the anti-GPVI ligands for GPVI was determined by assessing their effect on induction of platelet aggregation by agonists whose function is mediated through other well-characterized platelet receptors. For these studies, human PRP and WP preparations were used as needed to assess the activity of the various agonists. ADP was used as a specific agonist of the $P2Y_{12}$ and $P2Y_1$ teceptors, TRAP as an agonist of PAR-1, Arachidonic Acid as an agonist of the thromboxane A2 (TXA2) receptor and Ristocetin as an agonist of the vWF-GP1bα interaction. The potency of each agonist (ADP, TRAP, Arachidonic Acid, and Ristocetin) is determined from the maximal extent of percentage aggregation obtained from a dose response curve for the respective agonist, and a challenge concentration is determined to target $EC_{70-90}$% for each respective agonist.

1. Specificity Determination of the Anti-GPVI Nucleic Acid Ligands by AIPA and TIPA in WP.

For evaluating the potential interaction of anti-GPVI ligands with $P2Y_{12}$ and $P2Y_1$, a challenge concentration of 5 µM ADP was typically used to stimulate platelet aggregation, and for evaluating their potential interaction with PAR-1, a challenge concentration of 2.5 µM TFLLRN (TRAP) was typically used to stimulate platelet aggregation (the specific challenge agonist concentration for each experiment is determined based on the agonist dose response curve for each donor). ADP and TRAP-induced platelet aggregation was determined in WP preparations as described above. Specific inhibitors for each receptor were used as positive controls to demonstrate that inhibition of the target receptor was detectable in the assays. SCH79797 (Tocris Biosciences) was used as the positive control for PAR-1 antagonism, and INS50589 (Inspire Pharmaceuticals) was used as the positive control for $P2Y_{12}$ antagonism.

2. Specificity Determination of the GPVI Nucleic Acid Ligands by RIPA in PRP:

For evaluating the potential interaction of anti-GPVI ligands with vWF or GP1bα, a challenge concentration of 1.0-2.0 mg/mL Ristocetin (Sigma Cat #R7752) was used to stimulate platelet aggregation (the specific challenge agonist concentration for each experiment is determined based on the agonist dose response curve for each donor). Ristocetin-induced platelet aggregation is determined in PRP preparations as described above. HIP1 antibody to GP1bα (or isotype IgG control, Axxora Bio; 25 µg/ml final) was used as a positive control to demonstrate that inhibition of the target receptor GP1bα was detectable in the assays.

3. Specificity Determination of the GPVI Nucleic Acid Ligands by AAIPA in PRP:

For evaluating the potential for interaction of the anti-GPVI ligands with TXA2 receptor, a challenge concentration of 0.25-0.5 mg/ml Arachidonic Acid (Helena Biosciences; Cat #5364) was used to stimulate platelet aggregation (the specific challenge agonist concentration for each experiment is determined based on the agonist dose response curve for each donor). Arachidonic Acid-induced platelet aggregation is determined in PRP preparations as described above.

F. Collagen and CRP-Induced Platelet Aggregation Assays for Testing of Nucleic Acid Modulators of Anti-GPVI Ligands in WP and PRP:

Collagen and CRP-induced platelet aggregation was carried out in WP and PRP preparations as described above. For evaluation of the ability of nucleic acid modulators to reverse the inhibition of platelet aggregation by anti-GPVI ligands, anti-GPVI ligand concentration were tested at their $IC_{95-100}$ (the ligand concentration necessary to inhibit by 95-100% the aggregation elicited by a given concentration of challenge agonist). Platelet aggregation studies were performed as described above, except that after initial incubation of the platelet preparation with the anti-GPVI ligand, varying amounts of modulator were added, targeting a molar excess of modulator to ligand ranging from 8:1 to 0.5:1, and incubated together for 10 minutes before addition of agonist.

G. Durability Study of Anti-GPVI Ligand Reversal by Nucleic Acid Modulators in WP:

For evaluating the durability of reversal of anti-GPVI activity by nucleic acid modulators, RB490 (final concentration 0.25 µM) and RB515 (final concentration 0.75 µM) were added to a total volume 4 ml of WP suspension at 37° C. (order and timing of addition as described above for evaluating nucleic acid modulators), 450 µL aliquots of the WP suspension mixture were removed at indicated time points (0, 0.16, 0.5, 1, 1.5, 2, 2.5, 3, and 3.5 hrs), and collagen-induced platelet aggregation performed. To demonstrate the activity of the WP suspension, activity of RB490, and lack of interference by RB515 over the duration of this incubation, separate incubations were conducted over the 3.5 hr time period in which buffer alone, RB490 alone or RB515 alone were added to WP suspensions, and collagen-induced platelet aggregation determined.

Example 6

Inhibition of Collagen and CRP-Induced Platelet Function by Anti-GPVI Ligands

GPVI, expressed exclusively on platelets, is the major platelet collagen receptor. GPVI is required for stable platelet adhesion, and the interaction of GPVI with collagen is one of the most potent activators of platelets, triggering both inside-out activation of the platelet integrins $\alpha_2\beta_1$ and $\alpha_{IIb}\beta_3$, as well as secretion of platelet granule contents (which in turn activates nearby circulating platelets). In humans, deficiency of GPVI causes a loss of platelet activation in response to collagen, and in vitro, a loss of platelet aggregation in response to collagen. The predicted structure of the GPVI extracellular domain includes two Ig-like domains comprising the collagen-binding domain (CBD), followed by a heavily O-glycosylated stalk. Typical among LRC receptors, GPVI associates with the FcR γ-chain co-receptor. GPVI signaling is mediated indirectly through the γ-chain of FcR and directly through the GPVI cytoplasmic domain. The quaternary structure of fibrous collagen is required for GPVI activation, and collagen-mediated activation can be recapitulated by the cross-linked collagen-related peptide (CRP-XL), which consists of tripeptide repeats of the sequence $(GPO)_n$, where G is glycine, P is proline, and O is hydroxyproline.

The crystal structure of the CBD of GPVI, consisting of residues Q1-T183, has been solved (Horii et al, Blood 108; 2006, p 936-942). Structural data along with mutagenesis data, provides detailed insight into the molecular interaction between collagen and GPVI, and between CRP-XL and GPVI. Such studies also facilitate understanding of the mechanisms of GPVI activation. The CBD domain consists of the two Ig-like domains, C2-1 and C2-2 (where C2-1 is N-terminal and C2-2 C-terminal), oriented 90° apart. The GPVI CBD formed a dimer in the crystal structure with the C2-2 domains of respective CBDs interacting to form a back-to-back dimer. CRP and collagen each bind, in part, within a shallow groove on C2-1. This groove is unique to GPVI among LRC receptors, resulting from an 11-residue deletion in GPVI as compared to other LRC receptors. The floor of this binding groove is formed by several hydrophobic residues (L53, F54, P56, L62, and Y66 and the aliphatic portion of K41), with several polar (S43, S44, Q48, Q50, and S61) and basic (K41, R46, K59 and R166) residues around the periphery. Residues implicated directly in collagen or CRP binding fall into two clusters. The primary region is composed of basic residues on the surface of C2-1, including K41, K59, R60 and R166. The second cluster of residues implicated in CRP or collagen binding are located at the distal end of C2-1, and include L36 (implicated in collagen but not CRP binding), and V34 and the N-glycan attached to N72, which are implicated in both collagen and CRP binding. Consistent with mutational analysis, computational docking of CRP to the CBD of GPVI shows the CRP binding groove is located within the primary cluster of basic residues, with direct interaction with K41 and R166, and within bonding distance of the side chains of K59 and R60.

Each GPVI dimer contains two collagen binding grooves, one within each C2-1 subunit of the respective CBDs. Native collagen fibers are composed of a pseudo-hexagonal array of parallel CRP-like triple helices separated by 1.3 to 1.4 nm, an arrangement conserved in crystal structures of soluble CRP peptides. The collagen binding-grooves within a GPVI dimer are essentially parallel and separated by approximately 5.5 nm, the distance between n and n+4 helices in a collagen fiber. The geometric compatibility of the binding grooves with collagen helices would allow the GPVI dimer to bind simultaneously to 2 helices within a collagen fiber, and similarly to CRP-XL. Thus, the geometry of the CRP-XL peptides mimics that of native collagen, and enables the use of CRP-XL as a discrete probe of the CBD of GPVI.

Figure 15:
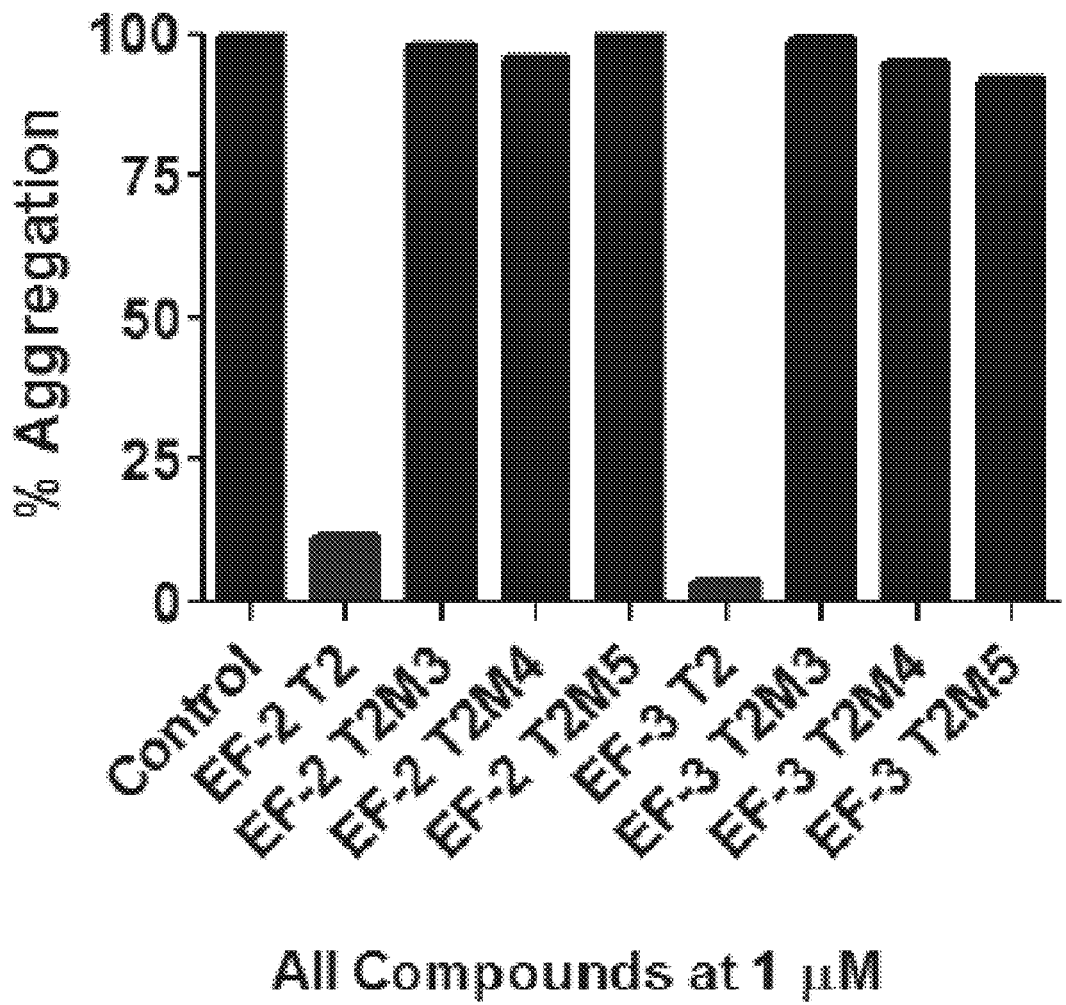
FIG. 15 is a graph of collagen-induced platelet aggregation expressed as a percentage of control for EF-2 and EF-3 GPVI ligand truncation variants as compared to variants containing inactivating point mutations.

To initially assess the ability of anti-GPVI ligands to block GPVI function, ligands EF-2 T2 and EF-3 T2 (See FIG. 9) were evaluated for their ability to block collagen-induced platelet activation in WP preparations, as described in Example 5. As a control for any potential non-specific effects of ligands on collagen-induced platelet aggregation, non-GPVI binding mutant ligands, EF-2 T2 M3-M5 and EF-3 T2 M3-M5 (See FIG. 9) were included in initial screens as a specificity control. As shown in FIG. 15, both EF-2 T2 and EF-3 T2 effectively blocked collagen-induced platelet aggregation, whereas inactive mutant control ligands had no effect.

Figure 16:
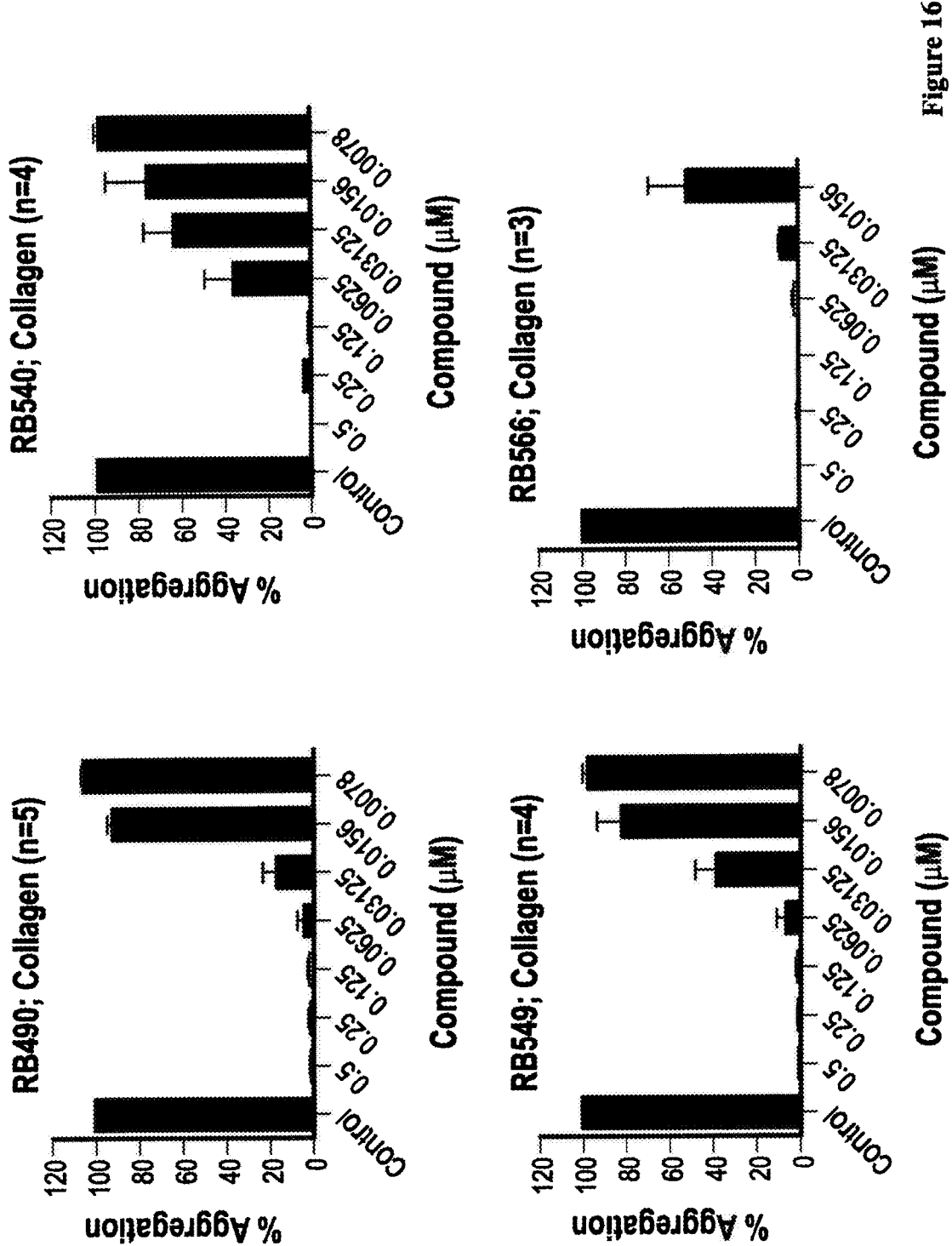
FIG. 16 is a graph of collagen-induced platelet aggregation expressed as percentage of control for varying concentrations of select GPVI nucleic acid ligands

Subsequently, the activity of optimized anti-GPVI ligands RB490, RB540, RB549 and RB566 were evaluated in collagen-induced platelet aggregation in WP preparations (FIG. 16). Optimized ligands each effectively blocked collagen-induced platelet aggregation. The relative potencies' of the anti-GPVI ligands were consistent with their respective affinities for GPVI, with RB540 ($K_d$ for GPVI of ~15 nM) exhibiting an $IC_{50}$ of ~44 nM, RB549 ($K_d$ for GPVI of ~6-7 nM) exhibiting an $IC_{50}$ of ~25 nM, RB490 ($K_d$ for GPVI of ~4-5 nM) exhibiting an $IC_{50}$ of ~23 nM, and RB566 ($K_d$ for GPVI of ~2-3 nM) exhibiting an $IC_{50}$ of ~20 nM.

To further probe the potential mechanism by which the ant-GPVI ligands block GPVI function, ligands RB490, RB549 and RB566 were evaluated for their ability to block CRP-XL induced platelet aggregation in WP preparations (FIG. 17), as described in Example 5. Consistent with their ability to block collagen-induced platelet aggregation, RB490, RB549 and RB566 blocked CRP-induced platelet aggregation in a dose-dependent manner. As with collagen, the relative potency of the ligands was consistent with their respective affinities for GPVI, with $IC_{50}$'s of 38 nM, 79 nM and 98 nM for RB566, RB490 and RB549, respectively. Not surprisingly, the $IC_{50}$'s of the anti-GPVI ligands are higher in CRP-induced platelet aggregation, as the CRP-XL used in these assays is a more potent platelet agonist than collagen. Together, these data are consistent with a mechanism of action in which the anti-GPVI ligands bind GPVI at or near the collagen-binding groove of GPVI, thereby blocking association of collagen or CRP-XL with GPVI on the platelet surface.

Figure 18:
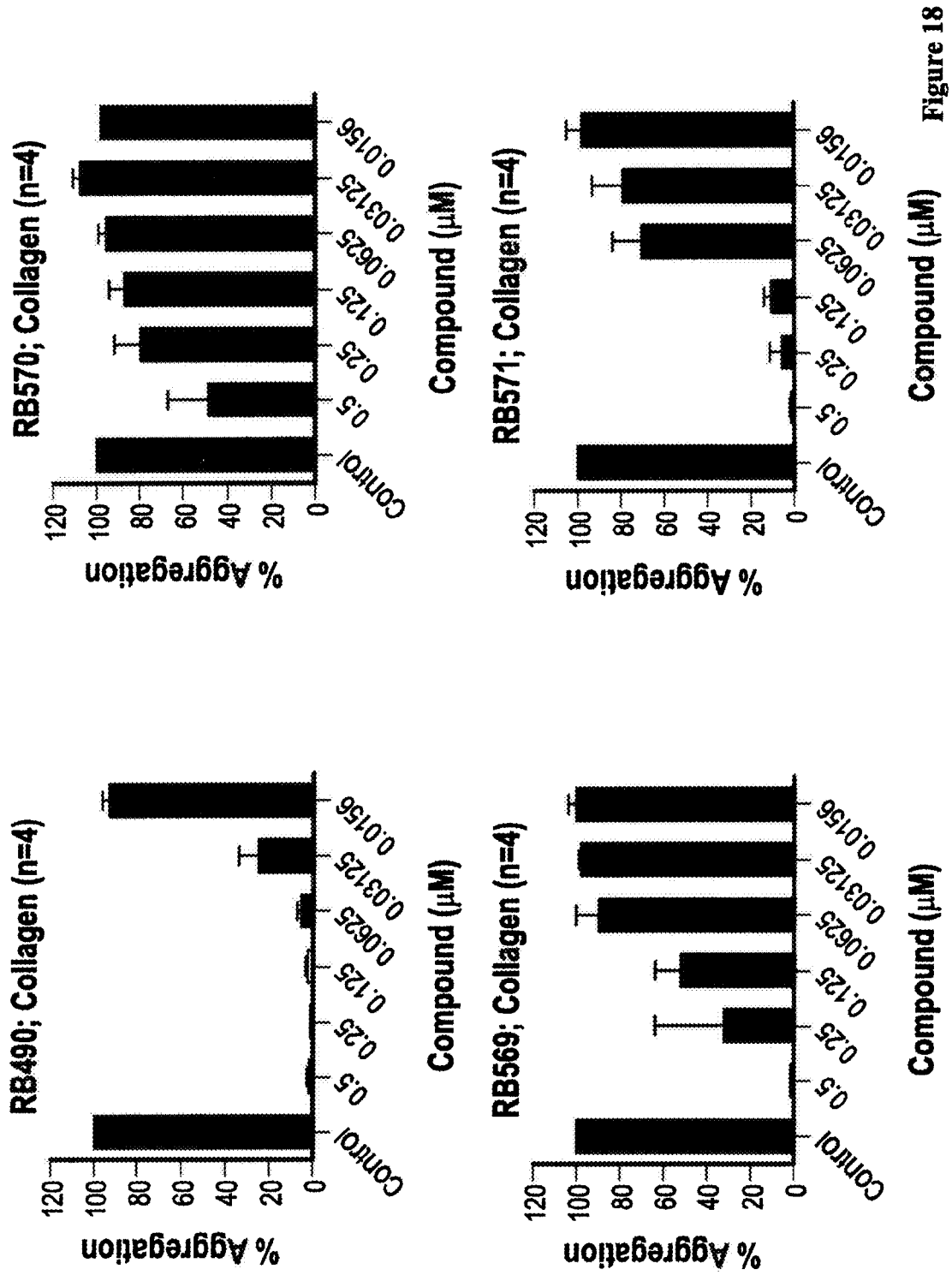
FIG. 18 shows graphs of collagen-induced platelet aggregation expressed as percentage of control for varying concentrations of select GPVI nucleic acid ligands
Figure 19:
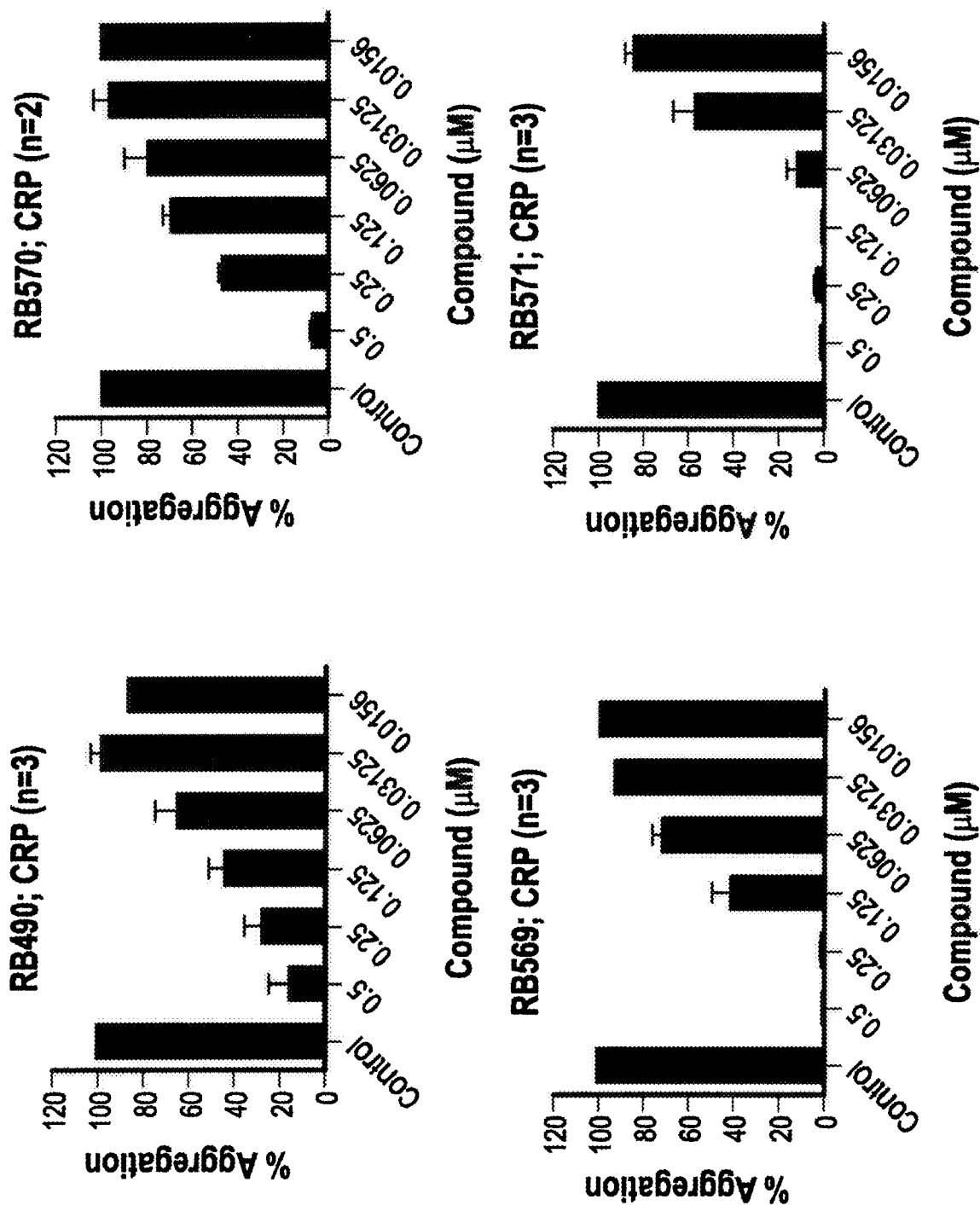
FIG. 19 shows graphs of CRP-induced platelet aggregation expressed as percentage of control for varying concentrations of select GPVI nucleic acid ligands.
Figure 20:
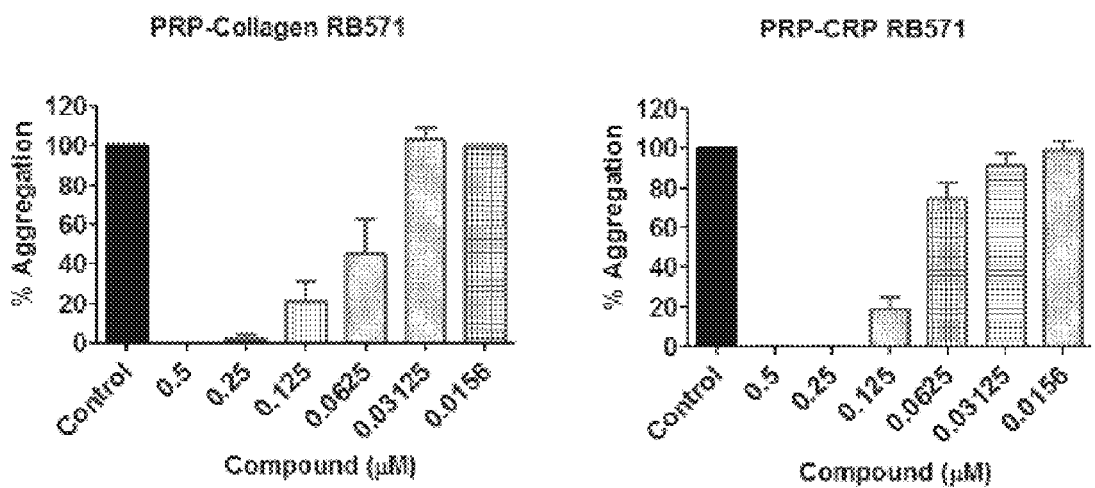
FIG. 20 shows graphs of collagen and CRP-induced platelet aggregation expressed as a percentage of control at varying concentrations of GPVI ligand RB571 in platelet rich plasma.

The anti-GPVI activity of PEGylated ligands RB570, RB569 and RB571 was also compared to RB490 in collagen and CRP-induced platelet aggregation in WP preparations (FIGS. 18-19). As above, the PEGylated ligands exhibited similar dose-dependent inhibition of collagen and CRP-induced platelet aggregation. The addition of PEG to the ligands modestly impacted their activity relative to RB490 in collagen-induced platelet aggregation, but not in CRP-induced platelet aggregation. RB571 exhibited the greatest potency in blocking CRP-induced aggregation in WP preparations, with an $IC_{50}$ of ~33 nM. Likewise, RB571 exhibited potent inhibition of collagen and CRP-induced platelet aggregation in PRP (See FIG. 20; See Example 5 for details).

Figure 21:
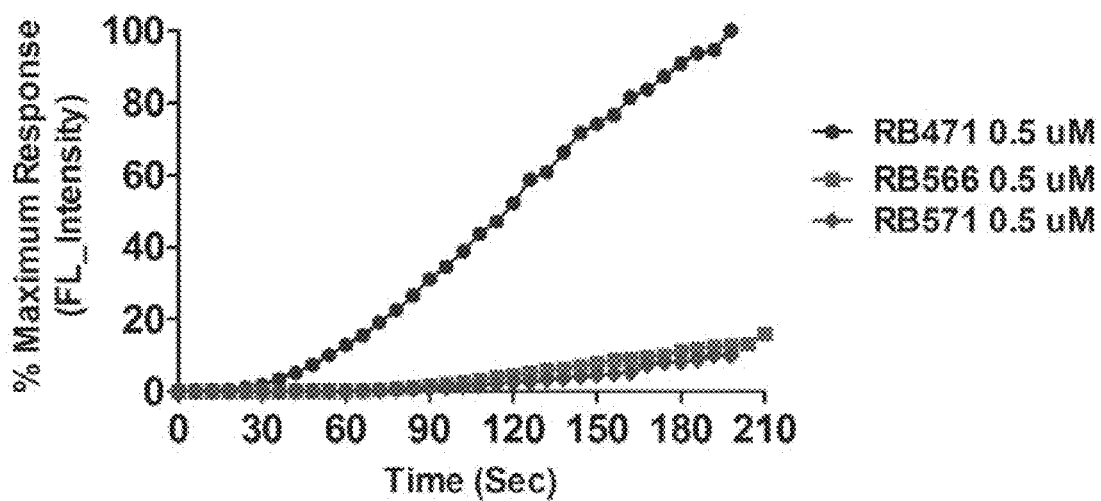
FIG. 21 is a graph showing the effects of GPVI nucleic acid ligands on platelet accumulation on a collagen-coated surface exposed to flowing whole blood expressed as the % maximum response of an inactive control ligand.

Anti-GPVI ligands were also evaluated for their ability to block platelet adhesion, activation and aggregation in response to GPVI interaction with collagen coated surfaces in whole blood under high shear, as described in Example 5. The format of this assay reflects many features of the in vivo function of GPVI, including association of GPVI with surface bound fibrillar collagen in flowing whole blood, as well as recapitulating three critical functions mediated by the GPVI-collagen interaction, namely platelet adhesion, activation and aggregation. RB566 and RB571 greatly reduced platelet adhesion, activation and aggregation (FIG. 21), as compared to the inactive ligand control RB471 (platelet response, in this assay was comparable between RB471 and buffer control).

Thus, anti-GPVI ligands block GPVI function in isolated platelet assays under static conditions and in flowing whole blood, impacting GPVI-mediated platelet adhesion, activation and aggregation. Additionally, consistent with a mechanism in which the anti-GPVI ligands bind at or near to the collagen binding site on GPVI, they exhibit dose-dependent inhibition of both collagen and CRP-induced platelet aggregation with a relative potency consistent with their respective affinities for GPVI.

Example 7

Specificity of Anti-GPVI Ligands for GPVI

Figure 22:
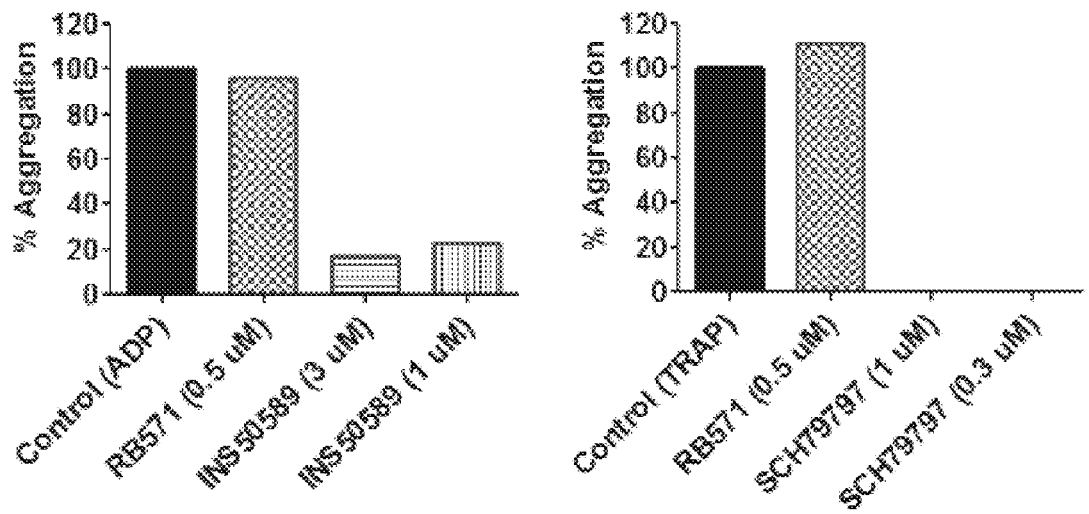
FIG. 22 shows graphs depicting specificity of GPVI ligand RB571 binding to GPVI as compared to platelet receptors $P2Y_1$, $P2Y_{12}$ and PAR-1.
Figure 23:
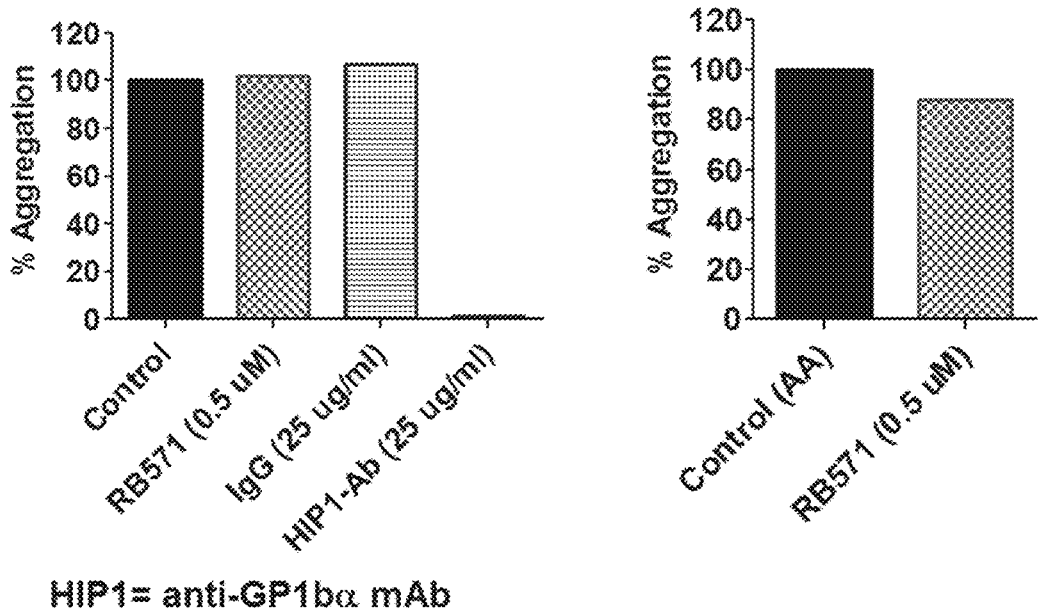
FIG. 23 shows graphs depicting specificity of GPVI ligand RB571 binding to GPVI as compared to the platelet receptor GP1bα-vWF interaction or the platelet thromboxane A2 receptor.

GPVI is one of several platelet receptors via which activation by its cognate ligand stimulates platelet activation and aggregation. Other such receptors include the thromboxane A2 receptor (TXA2), the ADP receptors $P2Y_{12}$ and $P2Y_1$, the thrombin receptor PAR-1, and GP1bα, which is activated by collagen-bound von Willebrands Factor (vWF). To determine the specificity with which the anti-GPVI ligands bind GPVI and block platelet function, the effect of the anti-GPVI ligand RB571 was assessed in ADP, TRAP (PAR-1 agonist), Arachidonic Acid (TXA2 agonist) and Ristocetin (agonist of the vWF-GP1bα interaction) induced platelet aggregation assays, as described in Example 5. As shown in FIGS. 22 and 23, RB571 had no impact on ADP or TRAP-induced platelet aggregation in WP preparations, or on Ristocetin or Arachidonic Acid-induced platelet aggregation in PRP preparations. Thus, as expected based on their high affinity for GPVI and isolation via SELEX, the anti-GPVI ligands are specific for GPVI.

Example 8

Nucleic Acid Modulators of Anti-GPVI Ligands

Figure 24:
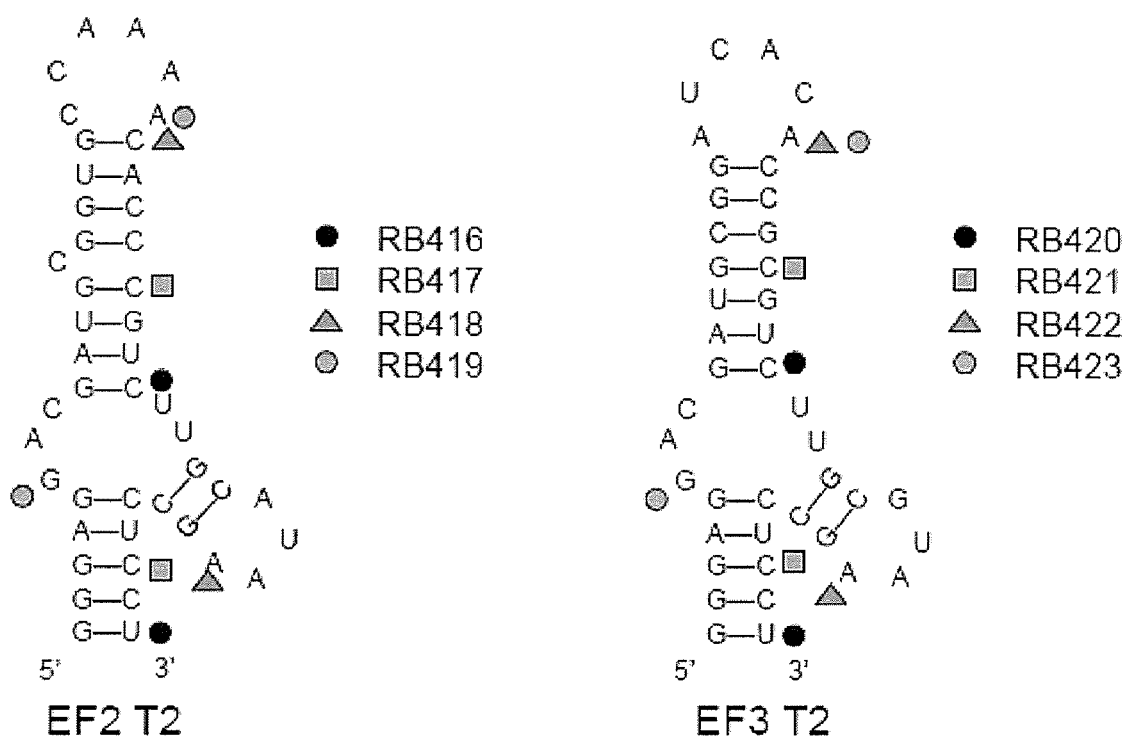
FIG. 24 shows the predicted secondary structure of the truncated sequence GPVI ligands EF2-T2 and EF3-T2 as well as regions of complementarity between the ligands and the GPVI ligand modulators RB416-423.

Ligands encode the information necessary to design nucleic acid modulators, or control agents, for them based upon complementary Watson-Crick basepairing rules. The effectiveness of a given control agent is dependent upon several factors, including accessibility of the targeted region of the ligand for nucleation with the control agent, as well as the absence of or limited internal secondary structure within the control agent, which would require denaturation prior to full-duplex formation with the ligand. To define regions of the anti-GPVI ligands that would be preferred regions for association with nucleic acid modulators, a series of control agents (See Table 7 and FIG. 24) were designed for EF-2 T2 and EF-3 T2.

control agents are expected to exhibit similar potency profiles to any of the described anti-GPVI ligands with which they can form fully-complementary duplexes.

Figure 27:
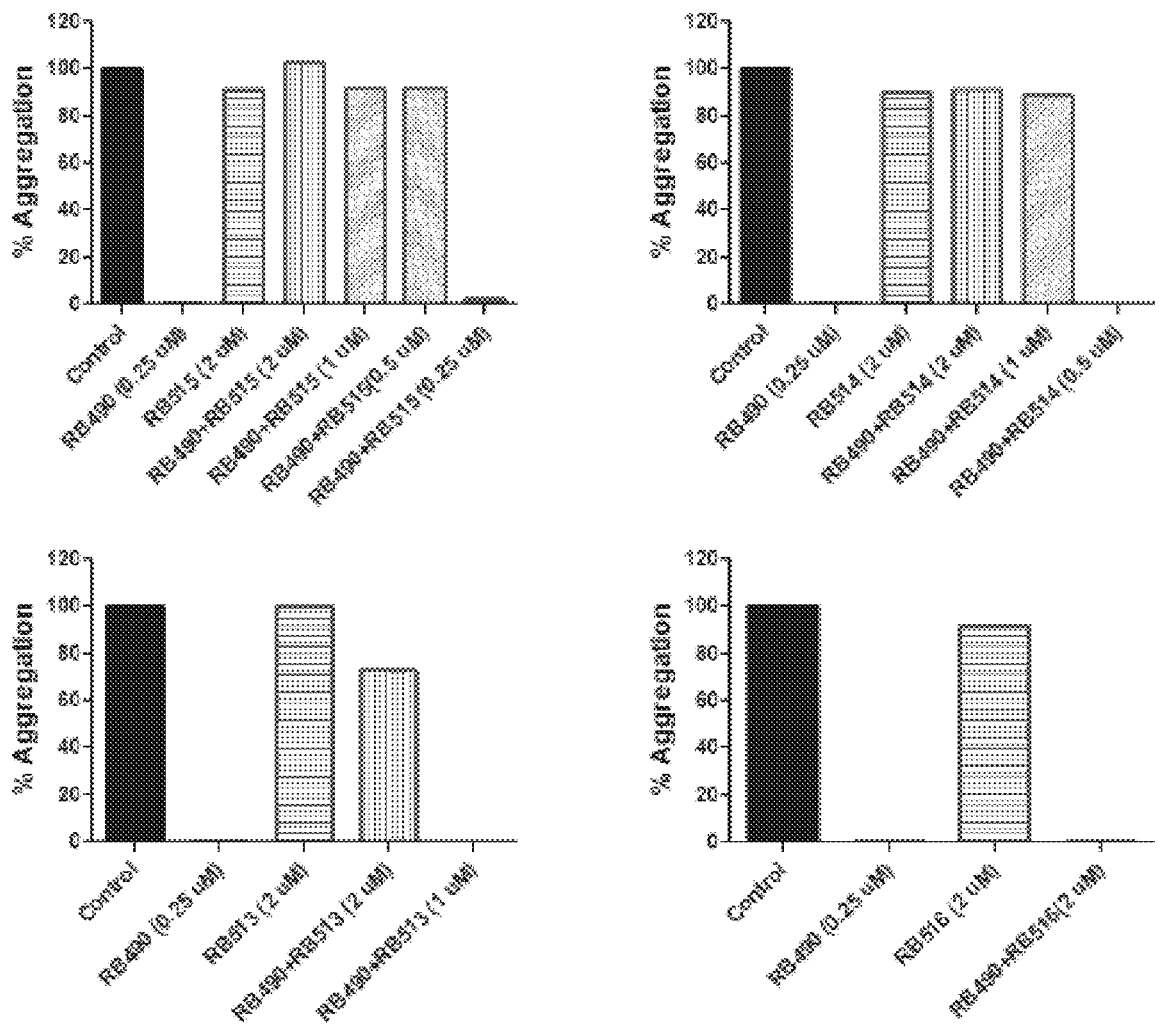
FIG. 27 shows graphs of collagen-induced platelet aggregation expressed as a percentage of control for GPVI ligand RB490 alone or in combination with various concentrations of different GPVI ligand modulators.
Figure 28:
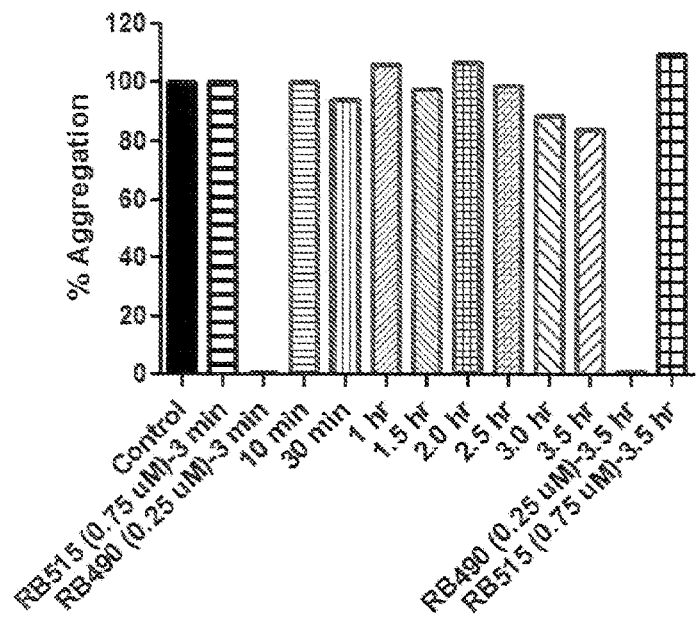
FIG. 28 shows a graph depicting durability of reversal of anti-GPVI activity of a GPVI nucleic acid ligand RB490 with GPVI ligand modulator RB515.

A similar set of potential control agents was designed against RB490 (See Table 7). As shown in FIG. 27, the potency with which these nucleic acid modulators reversed the anti-GPVI activity of RB490 was consistent with the preferred pairing regions as defined for control agents to EF-2T and EF-3T, with RB515 exhibiting the greatest potency. A key feature of a modulator is that once complexed with the ligand, the modulator:ligand complex does not dissociate, and the ligand activity remains durably reversed. To assess the durability of reversal of RB490 by RB515, we measured the durability of reversal of the anti-GPVI activity of RB490 in collagen-induced platelet aggregation, as described in Example 5. RB515 durably reversed RB490 activity for 3.5 hrs (FIG. 28), the duration in which the WP

TABLE 7

Modulators of GPVI Ligands

| Name | SEQ ID NO: | RB ID | Modified Sequence |
|---|---|---|---|
| EF-2 CA1 | 74 | RB416 | mAmGmGmAmGmGmCmUmUmAmUmGmCmAmAmG |
| EF-2 CA2 | 75 | RB417 | mGmAmGmGmCmUmUmAmUmGmCmAmAmGmAmCmG |
| EF-2 CA3 | 76 | RB418 | mUmUmAmUmGmCmAmAmGmAmCmGmGmUmG |
| EF-2 CA4 | 77 | RB419 | mUmUmUmGmGmCmAmCmCmGmCmAmUmCmGmUmC |
| EF-3 CA1 | 78 | RB420 | mAmGmGmAmGmGmCmUmUmAmCmGmCmAmAmG |
| EF-3 CA2 | 79 | RB421 | mGmAmGmGmCmUmUmAmCmGmCmAmAmGmAmCmG |
| EF-3 CA3 | 80 | RB422 | mUmUmAmCmGmCmAmAmGmAmCmGmCmGmGmU |
| EF-3 CA4 | 81 | RB423 | mUmGmUmGmAmUmCmCmGmCmAmUmCmGmUmC |
| RB490 CA 1 | 82 | RB513 | mGmGmGmAmGmGmCmUmUmAmUmGmCmAmGmGmCmG |
| RB490 CA 2 | 83 | RB514 | mGmAmGmGmCmUmUmAmUmGmCmAmGmGmCmG |
| RB490 CA 3 | 84 | RB515 | mUmUmAmUmGmCmAmGmGmCmG |
| RB490 CA 4 | 85 | RB516 | mCmGmCmCmGmUmCmCmUmCmCmC |
| RB538/571 Control Agent 5 (14mer) | 86 | RB543 | mGmCmUmUmAmUmGmCmCmAmGmGmCmG |
| RB538/571 Control Agent 6 (15mer) | 87 | RB544 | mGmGmCmUmUmAmUmGmCmCmAmGmGmCmG |
| RB538/571 Control Agent 7 (16mer) | 88 | RB545 | mAmGmGmCmUmUmAmUmGmCmCmAmGmGmCmG |

SEQ ID NOs. 137-151 correspond to the unmodified versions of the modulators described in the column titled "Modified Sequence."

Figure 25:
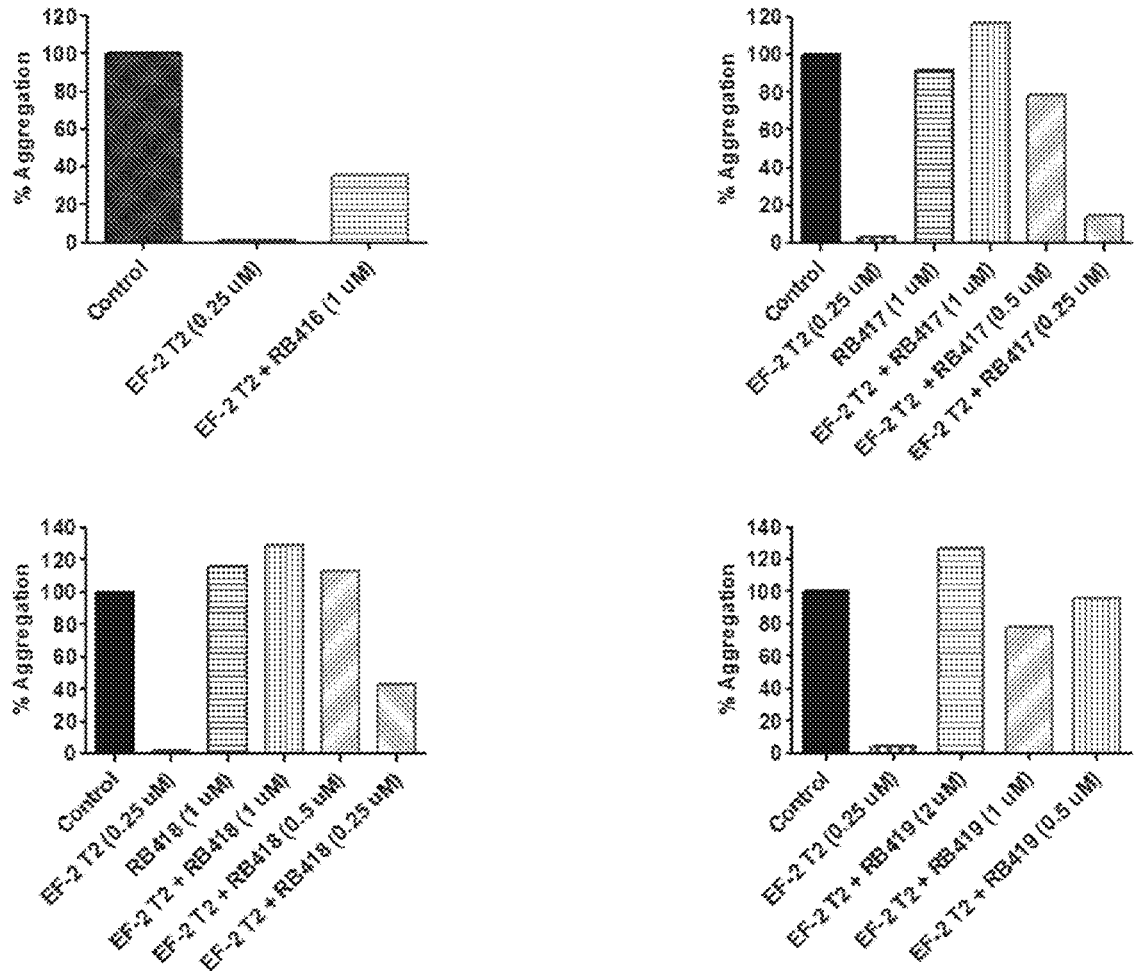
FIG. 25 shows graphs of collagen-induced platelet aggregation expressed as a percentage of control for GPVI ligand EF2-T2 alone or in combination with various concentrations of different GPVI ligand modulators.
Figure 26:
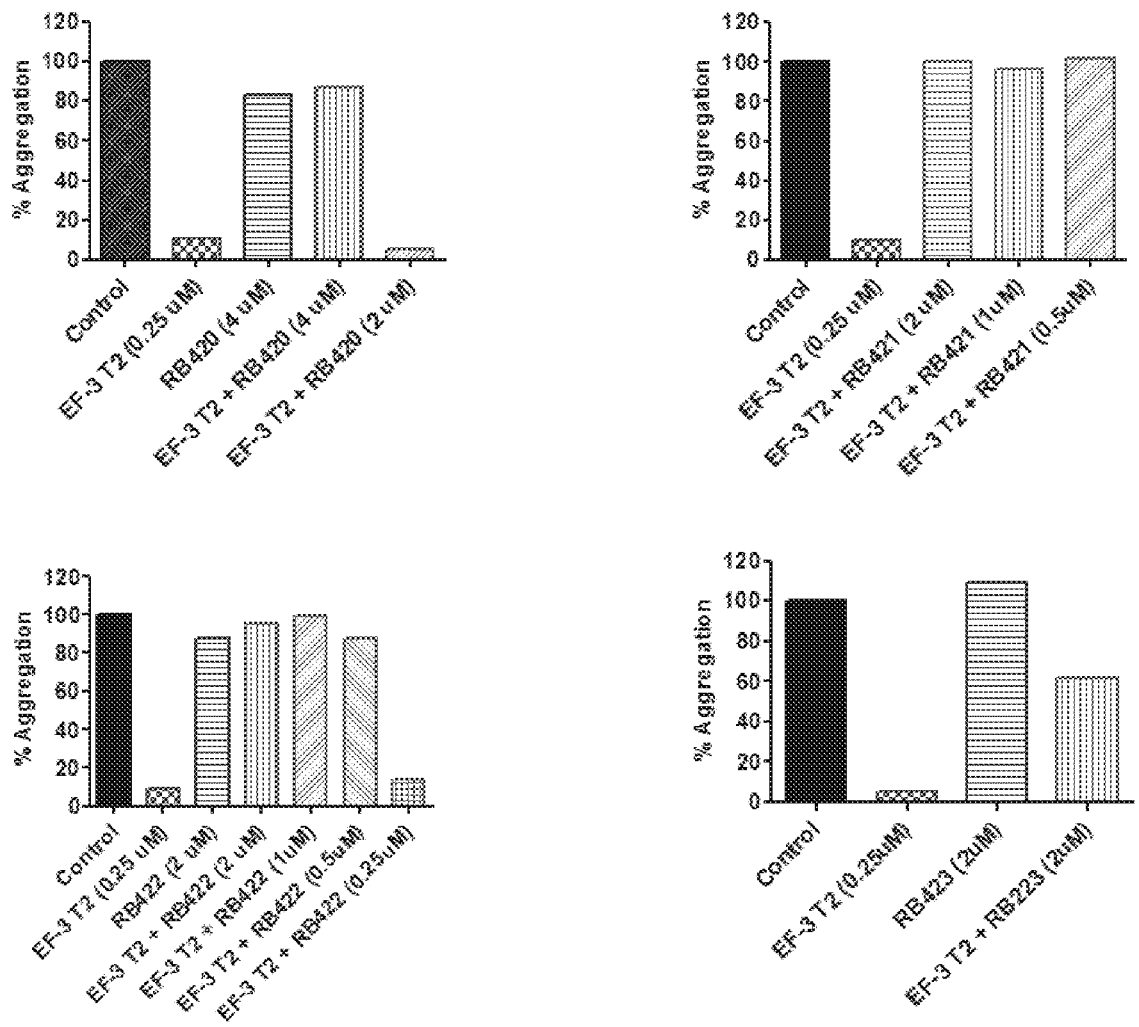
FIG. 26 shows graphs of collagen-induced platelet aggregation expressed as a percentage of control for GPVI ligand EF3-T2 alone or in combination with various concentrations of different GPVI ligand modulators.

The reversal activity of control agents RB416-RB419 for EF-2 T2 and RB420-423 for EF-3 T2 was assessed in platelet aggregation assays, as described in Example 5. As shown in FIGS. 25 and 26, the control agents were capable of reversing anti-GPVI ligand function within 10 minutes at low molar excesses to the GPVI ligand. A consistent potency between the control agents designed for EF-2 T2 and EF-3 T2 was observed with respect to the complementary regions of the control agents on the anti-GPVI ligands. RB418 and RB422, which associate with a similar region of the anti-GPVI ligands consisting of the 3' side of Stem 2, Loop 3, the 5' side of Stem 3 and Loop 4, exhibited the greatest potency. These preparations maintained full aggregation activity in response to collagen. Notably, RB490 in the absence of RB515 continued to fully inhibit collagen-induced platelet aggregation over the course of the 3.5 hr incubation period. The duration of reversal activity of RB515 for the anti-GPVI activity of RB490 is comparable to that determined for reversal of the anticoagulant activity of the anti-FIXa ligand RB006 with control agent RB007 in vitro in human plasma, an ligand: control agent pair which has demonstrated durable reversal in vivo in humans as well as other species.

Figure 29:
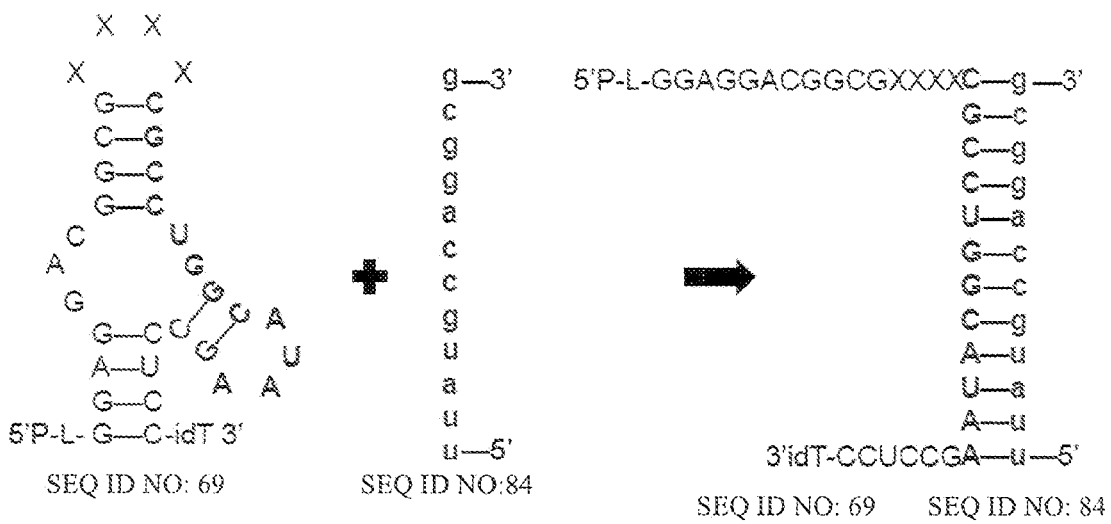
FIG. 29 shows predicted secondary structure of SEQ ID NO:69 (the base sequence of GPVI ligand RB571) and its predicted interaction with SEQ ID NO:84 (the base sequence of GPVI ligand modulator RB515).
Figure 30:
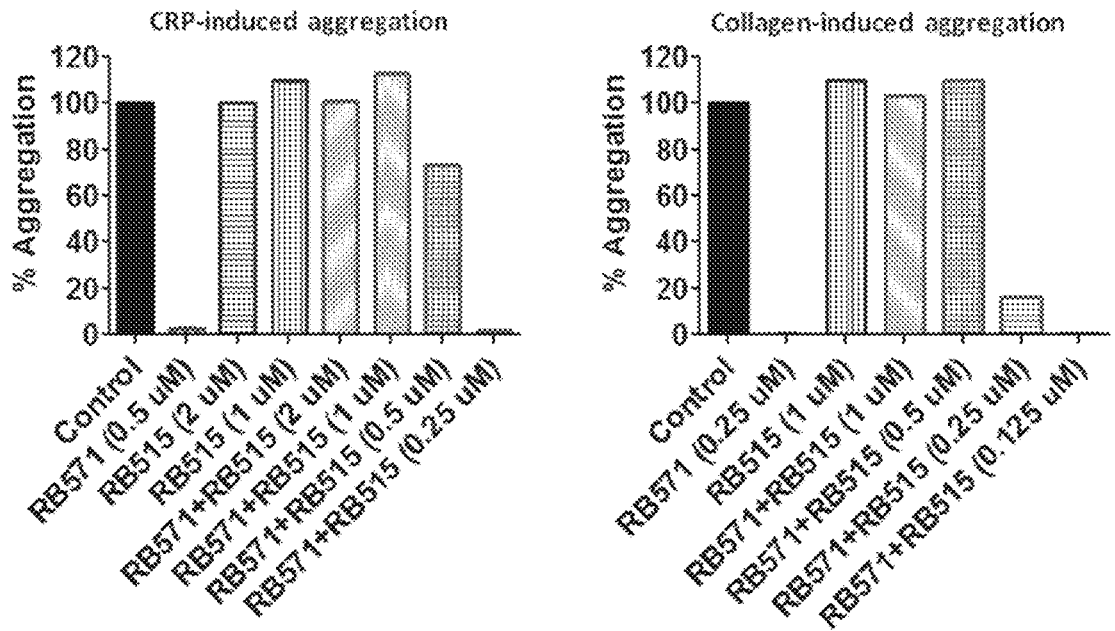
FIG. 30 shows graphs of collagen-induced and CRP-induced platelet aggregation expressed as a percentage of control for GPVI ligand RB571 alone or in combination with various concentrations of GPVI ligand modulator RB515.
Figure 31:
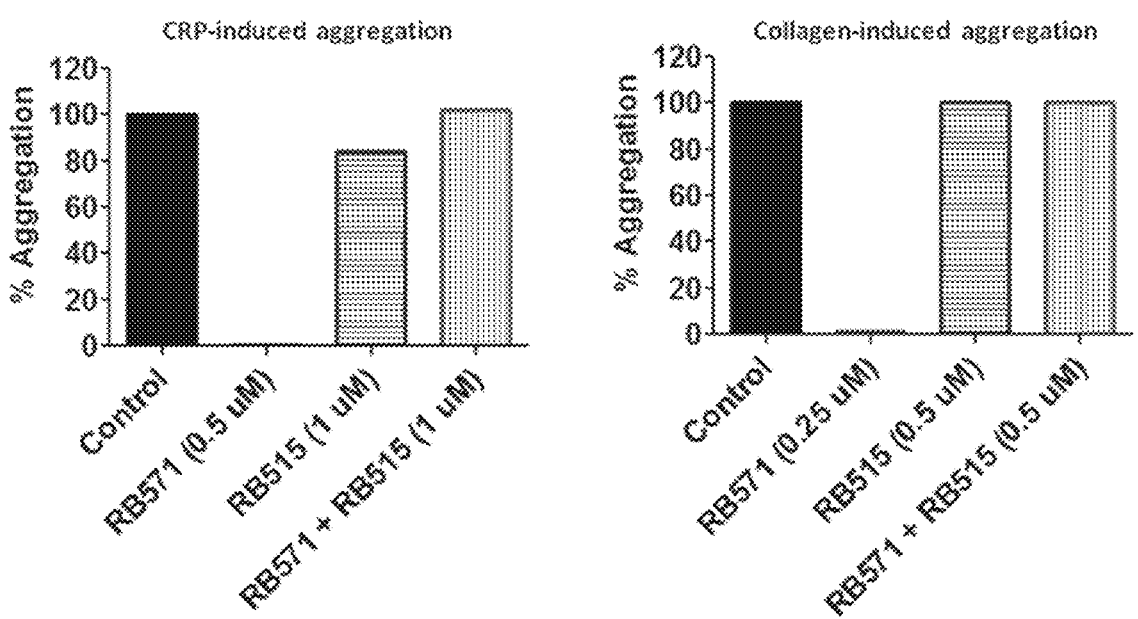
FIG. 31 shows graphs of collagen-induced and CRP-induced platelet aggregation expressed as a percentage of control for GPVI ligand RB571 alone or in combination with GPVI ligand modulator RB515 in platelet rich plasma.

RB571 and RB490 share the same base sequence (SEQ ID NO:69) within the region to which SEQ ID NO:84 (the base sequence of RB515) is complementary, and thus RB515 is a potential control agent for RB571 (See FIG. 29). Therefore, the reversal activity of RB515 for RB571 was assessed in collagen and CRP-induced platelet activation in WP and PRP preparations. RB515, at a low molar excess, effectively reversed the anti-GPVI activity of RB571 in response to both agonists in both matrices (FIGS. 30 and 31). The molar excess required for complete reversal of RB571 activity by RB515 is less than that required for full reversal of RB006 by RB007 in vitro (2:1 or lower molar ratio as compared to 4:1 for RB007 reversal of RB006), indicating a high likelihood of success for reversal of RB571 by RB515 in vivo in humans and other species.

---

The invention claimed is:

1. A GPVI ligand comprising a first isolated nucleic acid sequence, wherein said GPVI ligand binds glycoprotein VI (GPVI) and wherein said GPVI ligand comprises a secondary structure comprising in a 5' to 3' direction a first stem, a first loop, a second stem, a second loop, a third loop, a third stem and a fourth loop; and wherein said fourth loop comprises UAA.

2. A GPVI ligand comprising a first isolated nucleic acid sequence, wherein said GPVI ligand binds glycoprotein VI (GPVI) and wherein said GPVI ligand comprises a secondary structure comprising in a 5' to 3' direction a first stem, a first loop, a second stem, a spacer, a third loop, a third stem and a fourth loop; and wherein said fourth loop comprises UAA.

3. The GPVI ligand of claim 1, wherein the first nucleic acid comprises at least one modified nucleotide.

4. The GPVI ligand of claim 1, conjugated to a carrier.

5. The GPVI ligand of claim 4, wherein the carrier is a hydrophilic moiety.

6. The GPVI ligand of claim 5, wherein the hydrophilic moiety is a polyethylene glycol (PEG) molecule.

7. The GPVI ligand of claim 1, comprising a modified phosphate backbone.

8. The GPVI ligand of claim 2, comprising SEQ ID NO:69, wherein the spacer is incorporated between the 2'O-Methyl G at position 11 and the 2'O-Methyl C at position 12 of SEQ ID NO:69.

9. The GPVI ligand of claim 8, comprising a modified phosphate backbone.

10. The GPVI ligand of claim 2, wherein said GPVI ligand is selected from the group consisting of RB569, RB570, and RB571 as described in Table 6.

11. A pharmaceutical composition comprising the GPVI ligand of claim 1.

12. The GPVI ligand of claim 2, wherein the first nucleic acid comprises at least one modified nucleotide.

13. The GPVI ligand of claim 2, conjugated to a carrier.

14. The GPVI ligand of claim 13, wherein the carrier is a hydrophilic moiety.

15. The GPVI ligand of claim 14, wherein the hydrophilic moiety is a polyethylene glycol (PEG) molecule.

16. The GPVI ligand of claim 2, wherein the spacer is a glycol spacer.

17. The GPVI ligand of claim 2, wherein said GPVI ligand comprises SEQ ID NO:89.

18. The GPVI ligand of claim 2, wherein said GPVI ligand comprises SEQ ID NO:90.

19. The GPVI ligand of claim 2, wherein said GPVI ligand comprises SEQ ID NO:91.

20. The GPVI ligand of claim 2, wherein said GPVI ligand consists of SEQ ID NO:89.

21. The GPVI ligand of claim 2, wherein said GPVI ligand consists of SEQ ID NO:90.

22. The GPVI ligand of claim 2, wherein said GPVI ligand consists of SEQ ID NO:91.

23. A pharmaceutical composition comprising the GPVI ligand of claim 2.

\* \* \* \* \*